(12) United States Patent
Koizumi et al.

(10) Patent No.: US 11,918,630 B2
(45) Date of Patent: Mar. 5, 2024

(54) TREATMENT OF RETINA AND NERVE USING LAMININ

(71) Applicants: KYOTO PREFECTURAL PUBLIC UNIVERSITY CORPORATION, Kyoto (JP); THE DOSHISHA, Kyoto (JP); SENJU PHARMACEUTICAL CO., LTD., Osaka (JP)

(72) Inventors: Noriko Koizumi, Kyotanabe (JP); Naoki Okumura, Kyotanabe (JP); Shigeru Kinoshita, Kyoto (JP)

(73) Assignees: KYOTO PREFECTURAL PUBLIC UNIVERSITY CORPORATION, Kyoto (JP); THE DOSHISHA, Kyoto (JP); SENJU PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 15/523,282

(22) PCT Filed: Oct. 30, 2015

(86) PCT No.: PCT/JP2015/005474
§ 371 (c)(1),
(2) Date: Apr. 28, 2017

(87) PCT Pub. No.: WO2016/067629
PCT Pub. Date: May 6, 2016

(65) Prior Publication Data
US 2017/0319665 A1    Nov. 9, 2017

(30) Foreign Application Priority Data

Oct. 31, 2014 (JP) ................................. 2014-222948

(51) Int. Cl.
| A61K 38/39 | (2006.01) |
| A61K 9/00 | (2006.01) |
| A61K 31/4409 | (2006.01) |
| A61K 35/30 | (2015.01) |
| A61K 45/00 | (2006.01) |
| A61K 45/06 | (2006.01) |
| A61P 27/02 | (2006.01) |

(52) U.S. Cl.
CPC ............ *A61K 38/39* (2013.01); *A61K 9/0048* (2013.01); *A61K 31/4409* (2013.01); *A61K 35/30* (2013.01); *A61K 45/00* (2013.01); *A61K 45/06* (2013.01); *A61P 27/02* (2018.01)

(58) Field of Classification Search
None
See application file for complete search history.

(56) References Cited

U.S. PATENT DOCUMENTS

| 6,153,593 | A | 11/2000 | Burgeson et al. |
| 6,693,169 | B1 | 2/2004 | Brunken et al. |
| 6,933,273 | B2 | 8/2005 | Tryggvason et al. |
| 2002/0142954 | A1* | 10/2002 | Burgeson ............... A61P 27/02 514/17.7 |
| 2004/0106646 | A1 | 6/2004 | Takayama et al. |
| 2005/0214259 | A1 | 9/2005 | Sano et al. |
| 2007/0092550 | A1 | 4/2007 | Lui |
| 2007/0275365 | A1 | 11/2007 | Lui |
| 2008/0131430 | A1 | 6/2008 | Csaky et al. |
| 2009/0306772 | A1 | 12/2009 | Tao et al. |
| 2010/0028407 | A1 | 2/2010 | Del Priore et al. |
| 2010/0209402 | A1 | 8/2010 | Koizumi et al. |
| 2010/0233240 | A1 | 9/2010 | Koizumi et al. |
| 2011/0117062 | A1 | 5/2011 | Klimanskaya et al. |
| 2012/0156254 | A1 | 6/2012 | Tryggvason et al. |
| 2012/0282324 | A1* | 11/2012 | Xing .................. A61K 38/1825 424/450 |
| 2012/0288482 | A1 | 11/2012 | Takahashi et al. |
| 2013/0195806 | A1* | 8/2013 | Gay ........................ A61P 27/00 424/93.7 |
| 2014/0170751 | A1 | 6/2014 | Hayashi et al. |
| 2014/0341864 | A1 | 11/2014 | Nakano et al. |

(Continued)

FOREIGN PATENT DOCUMENTS

| CN | 1893988 A | 1/2007 |
| CN | 102597217 A | 7/2012 |

(Continued)

OTHER PUBLICATIONS

Caissie, R. et al. 2006. In vivo enhancement of sensory perception recovery in a tissue-engineered skin enriched with laminin. Biomaterials 27: 2988-2993. specif. pp. 2988, 2989.*
McMillan, J.R. et al. 2006. Colocalization of multiple laminin isoforms predominantly beneath hemidesmosomes in the upper lamina densa of the epidermal basement membrane. Journal of Histochemistry & Cytochemistry 54(1): 109-118. specif. p. 109.*
Menezes, K. et al. 2010. Polylaminin, a polymeric form of laminin, promotes regeneration after spinal cord injury. FASEB Journal 24: 4513-4522. specif. pp. 4513, 4514, 4515, 4520, 4521.*
Plantman, S. et al. 2008. Integrin-laminin interactions controlling neurite outgrowth from adult DRG neurons in vitro. Molecular and Cellular Neuroscience 39: 50-62, specif. pp. 50, 59.*

(Continued)

*Primary Examiner* — Adam Weidner
*Assistant Examiner* — Sharon M. Papciak
(74) *Attorney, Agent, or Firm* — Leydig, Voit & Mayer, Ltd.

(57) ABSTRACT

The present invention provides a technique for treating retinal epithelium and/or nerves. More specifically, the present invention is an agent for the treatment or prevention of retinal disease or the like and/or a disease, disorder, or ophthalmological state of the nerves, the agent including at least one factor selected from the group consisting of laminin and fragments thereof, wherein the problem is solved by also providing a technique characterized in that this agent is administered together with retinal pigment epithelial cells and/or nerve cells. Specifically, the present invention can include laminin 411 ($\alpha 4\beta 1\gamma 1$), laminin 511 ($\alpha 5\beta 1\gamma 1$), laminin 521 ($\alpha 5\beta 2\gamma 1$), or fragments of these.

3 Claims, 8 Drawing Sheets

Specification includes a Sequence Listing.

(56) References Cited

U.S. PATENT DOCUMENTS

| | | |
|---|---|---|
| 2014/0370007 A1 | 12/2014 | McCabe et al. |
| 2015/0025452 A1 | 1/2015 | Marinkovich et al. |
| 2017/0002318 A1 | 1/2017 | Koizumi et al. |
| 2017/0319693 A1 | 11/2017 | Koizumi et al. |
| 2020/0138868 A1 | 5/2020 | Thon et al. |

FOREIGN PATENT DOCUMENTS

| | | | | |
|---|---|---|---|---|
| CN | 102770136 A | 11/2012 | | |
| CN | 103384679 A | 11/2013 | | |
| CN | 103931608 A | 7/2014 | | |
| CN | 103937738 A | 7/2014 | | |
| EP | 2193806 A1 | 6/2010 | | |
| EP | 2487236 A1 | 8/2012 | | |
| EP | 2733201 A1 | 5/2014 | | |
| JP | 2013-128474 A | 7/2013 | | |
| RU | 2418067 C1 | 5/2011 | | |
| WO | WO 2000/066731 A2 | 11/2000 | | |
| WO | WO 2005/037144 A2 | 4/2005 | | |
| WO | WO-2007091790 A1 * | 8/2007 | ............ | A61K 35/30 |
| WO | WO 2012/173207 A1 | 12/2012 | | |
| WO | WO 2013/012087 A1 | 1/2013 | | |
| WO | WO 2014/087244 A2 | 6/2014 | | |
| WO | WO-2015053375 A1 * | 4/2015 | ........... | C12N 5/0621 |

OTHER PUBLICATIONS

Liebkind, R. et al. 2003. Is the soluble KDI domain of gamma laminin a regeneration factor for the mammalian central nervous system? Journal of Neuroscience Research 73: 637-643. specif. p. 637.*

Deutzmann, R. et al. 1990. Cell adhesion, spreading and neurite stimulation by laminin fragement E8 depends on maintenance of secondary and tertiary structure in its rod and globular domain. European Journal of Biochemistry 191: 513-522. specif. pp. 513, 515.*

Osumi, N. et al. 2008. Concise review: Pax6 transcription factor contributes to both embryonic and adult neurogenesis as a multifunctional regulator. Stem Cells 26: 1663-1672. specif. pp. 1663, 1666.*

Powell, S.K. et al. 1997. Neuronal laminins and their cellular receptors. International Journal of Biochemistry & Cell Biology 29: 401-414. specif. p. 403.*

Bystrom, B. et al. 2006. Distribution of laminins in the developing human eye. Investigative Ophthamology & Visual Science 47: 777-785. specif. pp. 777, 784.*

EngMT.Sawada, M. et al. Method or producing retinal pigment epithelial cell. International Patent Application Publication No. WO 2015/053375 A1; earliest priority date: Oct. 9, 2013. pp. 1-20. specif. pp. 3, 5.*

Edwards, M.M. et al. 2013. Laminins and retinal vascular development. Cell Adhesion & Migration 7(1): 82-89; specif. pp. 82, 84, 88.*

Suzuki, N. et al. 2005. Functional sites in the laminin alpha chains. Connective Tissue Research 46: 142-152; specif. p. 145.*

European Patent Office, Communication Pursuant to Rule 164(1) EPC in European Patent Application No. 15854105.2 (Jun. 11, 2018).

Okamoto et al., "Chapter 3 Strategies Toward Clinical Uses and Front-Line—Toward Drug Discovery and Establishment of Multicellular Bodies", *Experimental Medicine*, 30(10): 1646-1650 (2012).

Sekiguchi et al., "Laminin-511 E8 Fragment as a Culture Substrate for Human Pluripotent Stem Cells Under Feeder-Free/Xeno-Free Conditions", *Clinical Evaluation*, 41(1): 124-127 (2013).

Sekiguchi et al., "Fundamental Technique for the Spread of Regenerative Medicine", *Saishin Igaku*, 69: 685-697 (Mar. 2014).

Japanese Patent Office, International Search Report in International Patent Application No. PCT/JP2015/005474 dated Dec. 8, 2015.

Russian Patent Office, Official Action in Russian Patent Application No. 2017118405 dated May 31, 2019.

Li et al., "Relevance Between Proliferation of Corneal Endothelial Cell and Cytoskeleton Under the Action of Laminin," *Ophthalmic Research*, 23(1): 29 (2005).

Chinese Patent Office, First Office Action in Chinese Patent Application No. 201480065134X dated Feb. 3, 2019.

Chinese Patent Office, Search Report in Chinese Patent Application No. 201480065134X dated Feb. 3, 2019.

Russian Patent Office, Notification of Official Action in Russian Patent Application No. 2016125225 dated Jan. 22, 2019.

Aumailley et al., "A simplified laminin nomenclature," *Matrix Biol.*, 24: 326-332 (2005).

Doi et al., "Recombinant Human Laminin ($\alpha 5\beta 1\gamma 1$)," *J. Biol. Chem.*, 277(15): 12741-12748 (2002).

Engelmann et al., "Isolation and Long-Term Cultivation of Human Corneal Endothelial Cells," *Invest. Opthalmol. Vis. Sci.*, 29(11): 1656-1662 (1988).

Kakutani et al., "The efficiency of laminin-511 and laminin-521 as extracellular matrix for human corneal endothelial cell culture," *Investigative Ophthalmology and Visual Science*, 55: Abstract 2055 (2014) [retrieved on Mar. 19, 2015, from the Internet at URL: http://abstracts.iovs.org/cgi/content/short/55/May 2055].

Koizumi, "Development of New Therapeutic Modalities for Corneal Endothelial Disease Using Somatic Stem Cells", *Journal of Clinical and Experimental Medicine*, 241(10): 765-770 (2012), English translation and Int'l Search Report in PCT/JP2015/005473 dated Dec. 8, 2015.

Miyazaki et al., "Laminin E8 fragments support efficient adhesion and expansion of dissociated human pluripotent stem cells," *Nat. Commun.*, 3: 1236 (2012).

Numata et al., "Usefulness of Laminins 511 and 521 as Culture Substrates for Human Endothelial Cells", *Japan Cornea Conference 2014: 38th Japan Cornea Society and 30th Annual Meeting of Keratoplasty Society of Japan Program Shorokushu*, p. 82, abstract 038 (Jan. 31, 2014), English translation and Int'l Search Report in PCT/JP2015/005473 dated Dec. 8, 2015.

Okumura et al., "Usefulness of Laminins 511 and 521 in Culture of Corneal Endothelial Cells", *Regenerative Medicine*, 13 (Suppl. 2014): 243, abstract O-44-1 (Jan. 27, 2014), English translation and Int'l Search Report in PCT/JP2015/005473 dated Dec. 8, 2015.

Ueno et al., "Realization of Regenerative Medicine for Corneal Endothelium by Transplantation of Cultured Human Corneal Endothelial Cells", *Inflammation and Immunology*, 21(2): 131-135 (2013), English translation and Int'l Search Report in PCT/JP2015/005473 dated Dec. 8, 2015.

Yamaguchi et al., "Adhesion, Migration, and Proliferation of Cultured Human Corneal Endothelial Cells by Laminin-5," *Investigative Ophthalmology and Visual Science*, 52(2): 679-684 (2011).

European Patent Office, Communication pursuant to Article 94(3) EPC in European Patent Application No. 14831100.4 dated May 12, 2017.

European Patent Office, Communication Pursuant to Article 94(3) EPC in European Patent Application No. 14831100.4 dated Mar. 28, 2018.

European Patent Office, Communication Pursuant to Article 94(3) EPC in European Patent Application No. 14831100.4 dated Dec. 18, 2018.

European Patent Office, Extended European Search Report in European Patent Application No. 15854129.2 dated May 4, 2018.

Japanese Patent Office, International Search Report in International Patent Application No. PCT/JP2014/081917 dated Apr. 1, 2015.

Japanese Patent Office, International Search Report in International Patent Application No. PCT/JP2015/005473 dated Dec. 8, 2015.

Japanese Patent Office, Official Action in Japanese Patent Application No. 2016-535065 dated Aug. 27, 2018.

Russian Patent Office, Official Action in Russian Patent Application No. 2016125225 dated May 28, 2018.

Russian Patent Office, Search Report in Russian Patent Application No. 2016125225 dated May 28, 2018.

Russian Patent Office, Official Action in Russian Patent Application No. 2016125225 dated Sep. 5, 2018.

Colby et al., "Medical Treatment of Fuchs' Dystrophy in our Lifetime?" *Invest. Ophthalmol. Vis. Sci.*, 54(4): 2503 (2013).

(56) References Cited

OTHER PUBLICATIONS

Davis et al., "Regulation of Tissue Injury Responses by the Exposure of Matricryptic Sites within Extracellular Matrix Molecules," *Am. J. Pathol.*, 156(5): 1489-1498 (2000).
Kaufman, "The corneal endothelium in intraocular surgery," *J. R. Soc. Med.*, 73(3): 165-171 (1980).
Kerafast, "Human Laminin 332," Catalog No. EUV102 and EUV103 (2019).
Medline, "Fuchs' dystrophy," *MedlinePlus Medical Encyclopedia* (2015) [obtained at http://www.nlm.nih.gov/medlineplus/ency/article/007295.htm on Oct. 18, 2019].
Japanese Patent Office, Office Action in Japanese Patent Application No. 2016-556373 dated Aug. 2, 2019.
Japanese Patent Office, Office Action in Japanese Patent Application No. 2016-556374 dated Aug. 2, 2019.
Europen Patent Office, Communication Pursuant to Article 94(3) EPC in European Patent Application No. 15854105.2 dated Oct. 14, 2019.
Mexican Patent Office, Office Action in Mexican Patent Application No. MX/a/2016/006915 dated Jun. 20, 2019.
Chinese Patent Office, Second Office Action in Chinese Patent Application No. 201480065134.X dated Jul. 3, 2019.
Okumura et al., "Laminin-511 and -521 Enable Efficient In Vitro Expansion of Human Corneal Endothelial Cells," *Invest. Ophthalmol. Vis. Sci.*, 56(5): 2933-2942 (2015).
Japanese Patent Office, Notice of Reasons for Refusal in Japanese Patent Application No. 2016-556374 dated Mar. 3, 2020.
Brazilian Patent Office, Office Action in Brazilian Patent Application No. BR112016011096-0 dated Nov. 4, 2019.
Taniguchi et al., "The C-terminal Region of Laminin B Chains Modulates the Integrin Binding Affinities of Laminins," *J. Biol. Chem.*, 284(12): 7820-7831 (2009).
China National Intellectual Property Administration, First Office Action and Search Report in Chinese Patent Application No. 201580059642.1 dated Feb. 3, 2020.
European Patent Office, Communication Pursuant to Article 94(3) EPC in European Patent Application No. 15854129.2 dated Jan. 28, 2020.
Japanese Patent Office, Final Office Action in Japanese Patent Application No. 2016-556373 dated Mar. 3, 2020.
Huang et al., "A Hierarchy of Endothelial Colony-Forming Cell Activity Displayed by Bovine Corneal Endothelial Cells," *Investigative Ophthalmology & Visual Science*, 51(8): 3943-3949 (2010).
Miner et al., "Laminin Functions in Tissue Morphogenesis," *Annu. Rev. Cell Dev. Biol.*, 20: 255-284 (2004).
European Patent Office, Communication Pursuant to Article 94(3) EPC in European Patent Application No. 15854105.2 dated May 12, 2020.
Brazilian Patent Office, Preliminary Office Action in Brazilian Patent Application No. BR112017008805-3 dated Aug. 13, 2020.
China National Intellectual Property Administration, Second Office Action in Chinese Patent Application No. 201580059642.1 dated Sep. 2, 2020.
Mexican Patent Office, Office Action in Mexican Patent Application No. MX/a/2017/005522 dated Sep. 17, 2020.
Yan et al., "III. Repair of Corneal endothelial Wound," Ocular Physiology, 46-47 (Dec. 31, 2001), partial English translation and Office Action In CN 201580059642.1 dated Jan. 4, 2021.
Zheng, "VI. Research progress of corneal endothelial transplantation," *Ophthalmological Clinical Theory and Practice*, 87-88 (Oct. 31, 1998), English translation and Office Action in CN 201580059642.1 dated Jan. 4, 2021.
China National Intellectual Property Administration, Third Office Action in Chinese Patent Application No. 201580059642.1 dated Jan. 4, 2021.
Japanese Patent Office, Inquiry in Appeal No. 2020-7637 for Japanese Patent Application No. 2016-556373 dated Apr. 9, 2021.
Japanese Patent Office, Notice of Reasons for Rejection in Appeal No. 2020-7637 for Japanese Patent Application No. 2016-556373 dated Apr. 9, 2021.
European Patent Office, Communication Pursuant to Article 94(3) EPC in European Patent Application No. 15854129.2 dated Mar. 9, 2021.
Farina et al., "Temporal proteomic profiling of embryonic stem cell secretome during cardiac and neural differentiation," *Proteomics*, 11(20): 3972-3982 (2011).
Gospodarowicz et al., "The Production and Localization of Laminin in Cultured Vascular and Corneal Endothelial Cells," *J. Cell. Phys.*, 107(2): 171-183 (1981).
Canadian Patent Office, Examination Report and Search Report in Canadian Patent Application No. 2,965,770 dated Oct. 20, 2021.
Japanese Patent Office, Notice of Reasons for Refusal in Japanese Patent Application No. 2020-097055 dated Oct. 6, 2021.
China National Intellectual Property Administration, Decision of Rejection in Chinese Patent Application No. 201580059642.1 dated Apr. 21, 2021.
Mexican Patent Office, Office Action in Mexican Patent Application No. MX/a/2017/005522 dated Apr. 15, 2021.
Novus Biologicals, "Laminin Antibody," Catalog Entry NB300-144 (2022).
Takizawa et al., "Mechanistic basis for the recognition of laminin-511 by α6β1 integrin," *Sci. Adv.*, 3(9): e170497 (2017).
Japanese Patent Office, Decision of Refusal in Japanese Patent Application No. 2020-097055 dated Feb. 15, 2022.
U.S. Appl. No. 15/100,147, filed May 27, 2016.
U.S. Appl. No. 15/523,231, filed Apr. 28, 2017.
Thoughtco, "Suspension Definition in Chemistry" [accessed on Aug. 26, 2022 at https://www.thoughtco.com/definition-of-suspension-605714] (2022).
Okumura et al., "Enhancement on Primate Corneal Endothelial Cell Survival In Vitro by a ROCK Inhibitor," *Invest. Ophthalmol. Vis. Sci.*, 50(8): 3680-3687 (2009).
Canadian Intellectual Property Office, Examiner Requisition in Canadian Patent Application No. 2,965,770 dated Nov. 2, 2022.

\* cited by examiner

Transplantation of cultured retinal pigment epithelial cell under rabbit retina with concomitant use of E8

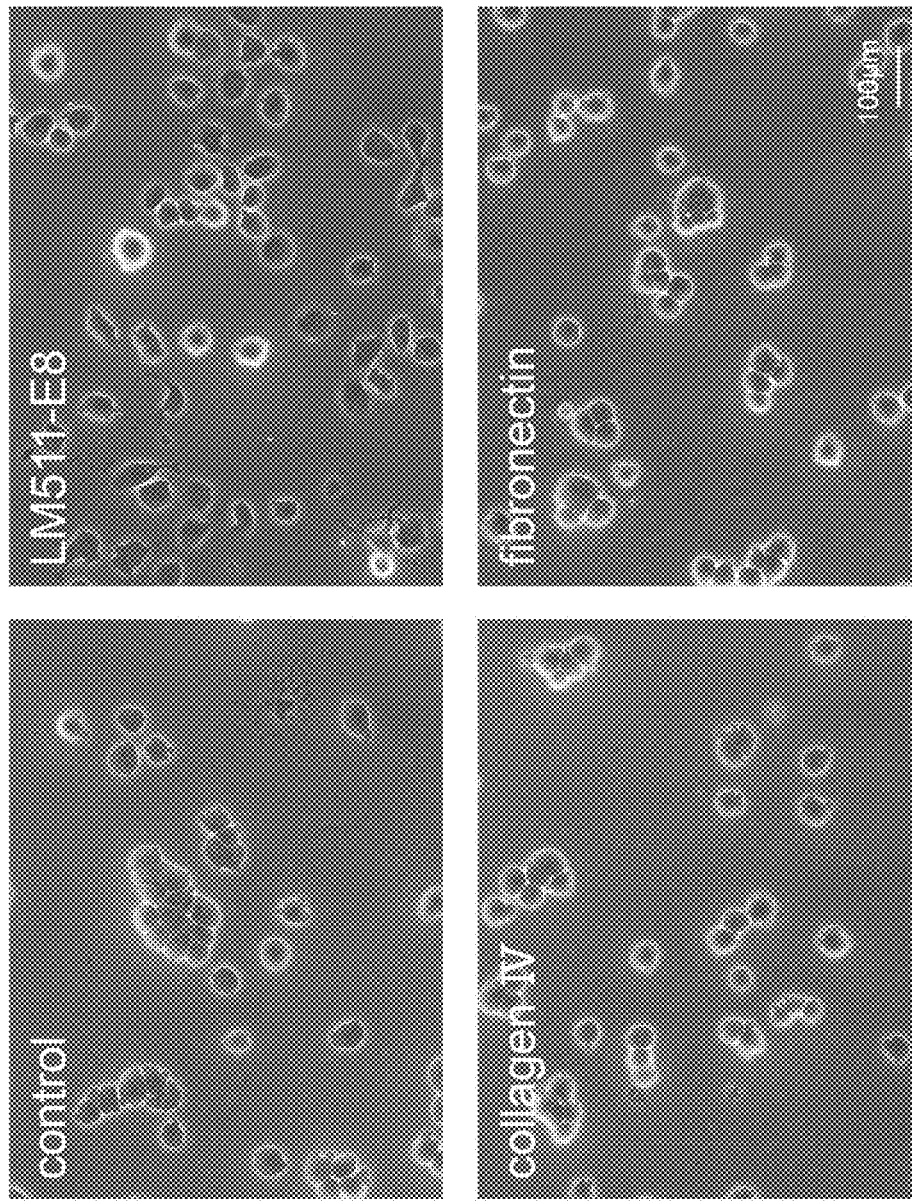
Fig. 5 Pictures of nerve cells (N2a) upon adding laminin to medium from phase contrast microscope

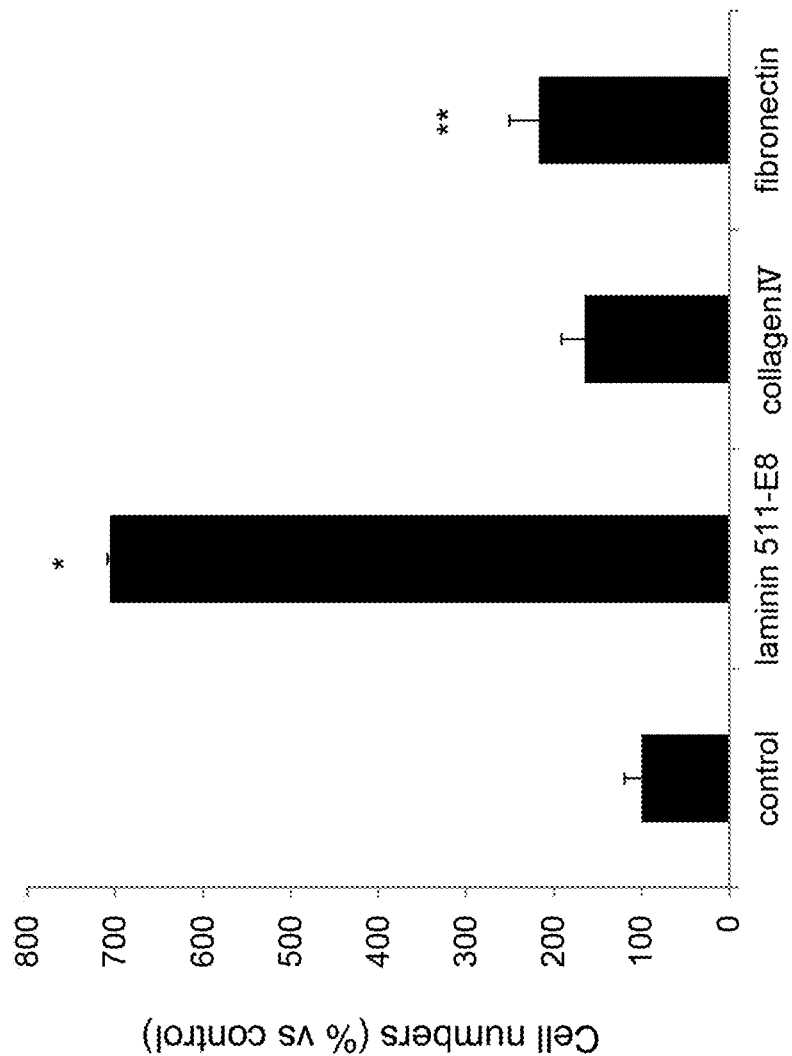
Fig. 6 Effect of adding laminin to medium on adhesion of nerve cells (N2a)

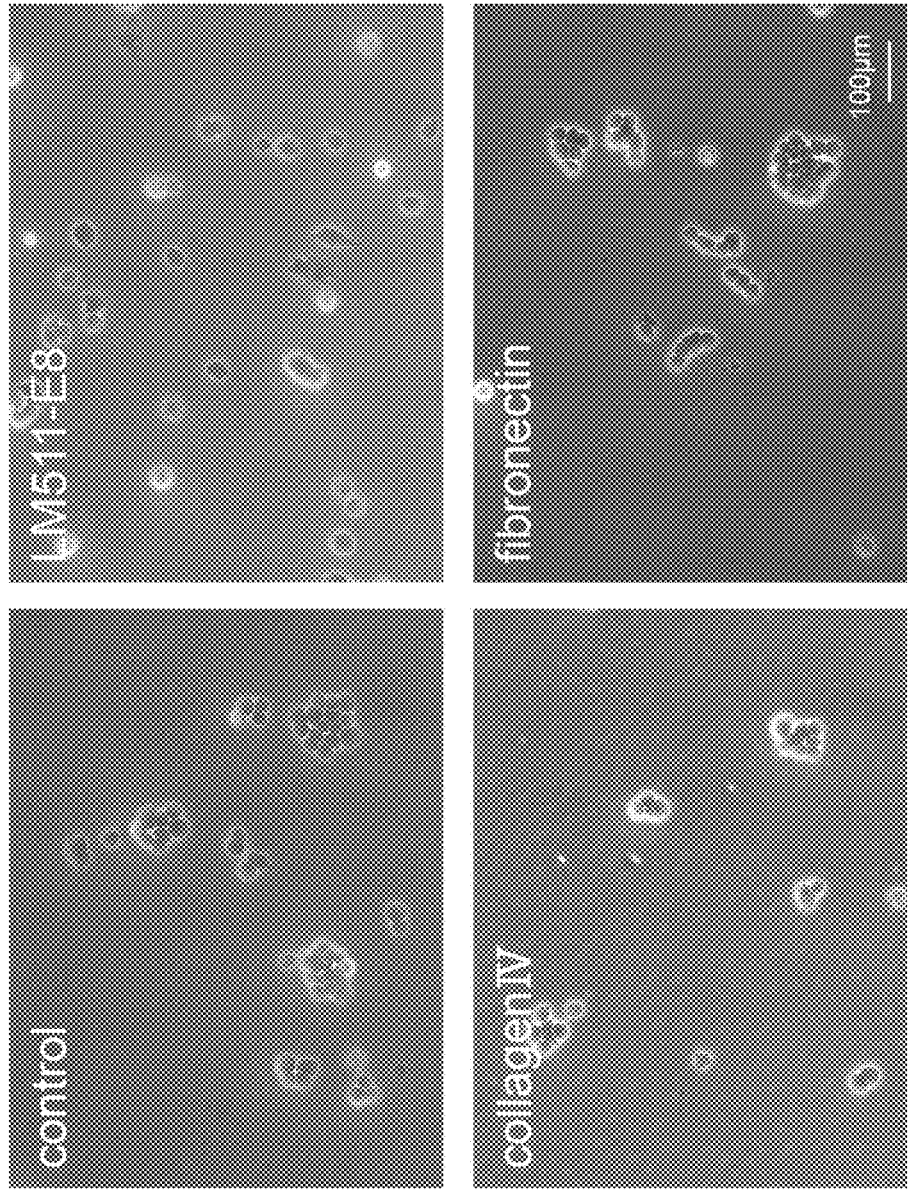
Fig. 7 Pictures of nerve cells (H-SY5Y) upon adding laminin to medium from phase contrast microscope

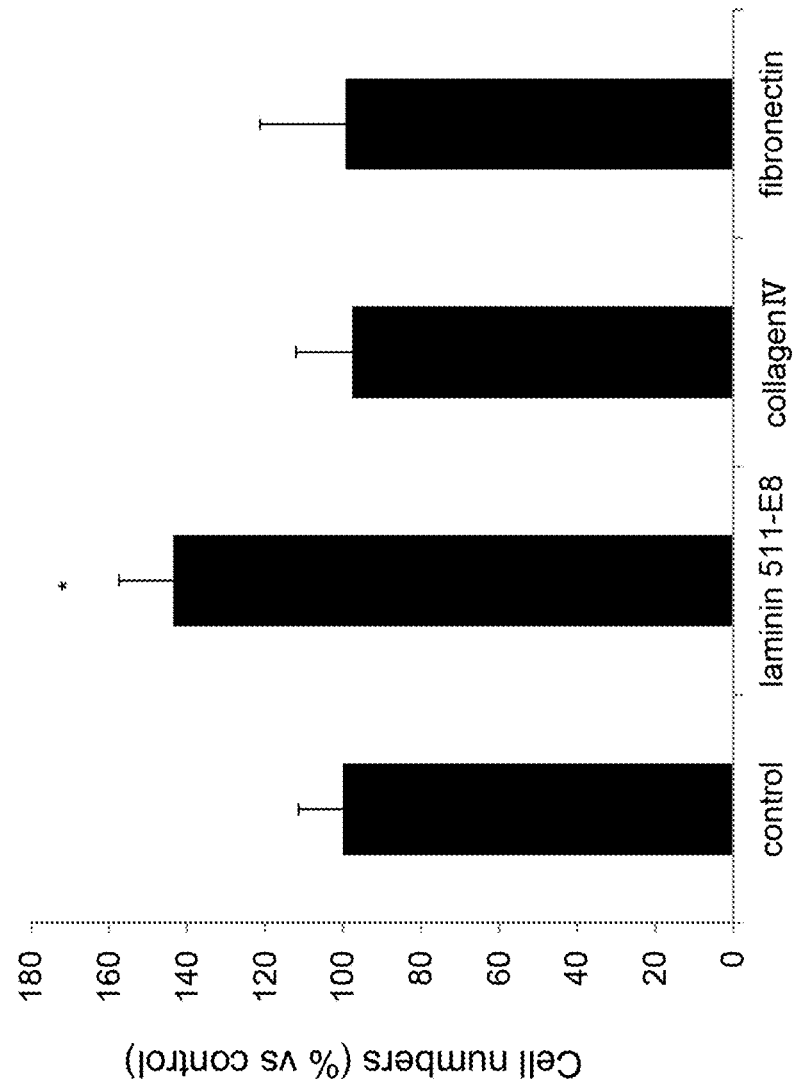

TREATMENT OF RETINA AND NERVE USING LAMININ

CROSS-REFERENCE TO RELATED APPLICATIONS

This patent application is the U.S. national phase of International Patent Application No. PCT/JP2015/005474, filed Oct. 30, 2015, which claims the benefit of Japanese Patent Application No. 2014-222948, filed on Oct. 31, 2014, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 119,030 bytes ASCII (Text) file named "728062Sequence-Listing.txt," created Apr. 28, 2016.

TECHNICAL FIELD

The present invention relates to a novel therapy using a laminin. More specifically, the present invention relates to ophthalmic therapy using a laminin and still more specifically relates to therapy and prophylaxis of retinal pigment epithelia and nerves.

BACKGROUND ART

A retina is an important part of an ophthalmic region. Development of a therapeutic method using transplantation of cultured human retinal pigment epithelial cells is awaited for visual impairment due to a retinal disorder at the macula or the like, such as age-related macular degeneration, retinitis pigmentosa, or retinal pigment epitheliopathy.

Patent Literatures 1 and 2 are known with regard to the relationship between laminins and ophthalmology.

A nerve is important for normal daily life. Development of a therapeutic method using transplantation of cultured nerve cells is awaited.

Non-Patent Literatures 1 to 4 are known with regard to the relationship between laminins and nerves.

CITATION LIST

Patent Literature

[PTL 1] Japanese National Phase PCT Laid-open Publication No.
[PTL 2] Japanese National Phase PCT Laid-open Publication No.

Non Patent Literature

[NPL 1] Gonzalez-Perez F, Udina E, Navarro X. Int Rev Neurobiol. 2013; 108: 257-275
[NPL 2] Plantman S. Biomed Res Int. 2013; 2013: 981695
[NPL 3] Wu H, Xiong W C, Mei L. Development. 2010
[NPL 4] Fusaoka-Nishioka B. et al., Neuroscience Res. 71, 2011,

SUMMARY OF INVENTION

Solution to Problem

The inventors have discovered that specific laminins are useful especially in therapy of retinal pigment epithelia and/or nerves, on which the present invention is based. In particular, the inventors' discovery that specific laminins promote adhesion of especially retinal pigment epithelial and/or nerve cells has led to the discovery that a disease, a disorder, or a condition associated with cell adhesion can be improved. Thus, the present invention representatively provides the following.

<Retina Related Therapy>

(1) A therapeutic or prophylactic agent for a disease, a disorder, or a condition of a retinal pigment epithelium, comprising at least one agent selected from the group consisting of laminins and fragments thereof, wherein the laminins comprise a γ1 chain.

(2) The therapeutic or prophylactic agent of item 1, wherein the laminins further comprise an α5 chain.

(3) The therapeutic or prophylactic agent of item 1 or 2, wherein the laminins comprise laminin 511 (α5β1γ1) and laminin 521 (α5β2γ1).

(4) The therapeutic or prophylactic agent of any one of items 1 to 3, wherein the fragments have cell adhesion capability of a retinal pigment epithelial cell.

(5) The therapeutic or prophylactic agent of any one of items 1 to 4, wherein the agent is laminin 511, laminin 521, or a laminin 511-E8 fragment.

(6) The therapeutic or prophylactic agent of any one of items 1 to 5, wherein the retinal pigment epithelium is from a primate.

(7) The therapeutic or prophylactic agent of any one of items 1 to 6, wherein the disease, disorder, or condition of the retinal pigment epithelium is selected from the group consisting of exudative and atrophic age-related macular degeneration, retinitis pigmentosa, retinal pigment epitheliopathy (central serous chorioretinopathy), and other diseases resulting in diminished visual acuity and diminished visual function due to a retinal disorder especially at the macula or the like.

(8) The therapeutic or prophylactic agent of any one of items 1 to 7, further comprising a retinal pigment epithelial cell.

(9) The therapeutic or prophylactic agent of any one of items 1 to 8, further comprising a ROCK inhibitor.

(10) The therapeutic or prophylactic agent of item 9, wherein the ROCK inhibitor is selected from the group consisting of Y-27632 ((R)-(+)-trans-(4-pyridyl)-4-(1-aminoethyl) cyclohexanecarboxamide dihydrochloride monohydrate) and a pharmaceutically acceptable salt thereof.

(11) The therapeutic or prophylactic agent of any one of items 1 to 10, further comprising a retinal pigment epithelial cell and a ROCK inhibitor.

(12) The therapeutic or prophylactic agent of any one of items 1 to 11, wherein the agent is injected under a retina thereby being contacted with cells and/or tissue constituting the retina.

(13) The therapeutic or prophylactic agent of any one of items 1 to 12, wherein the agent is present at about 21 nM or greater.

(14) The therapeutic or prophylactic agent of any one of items 1 to 13, wherein a retinal pigment epithelial cell is further administered.

(15) The therapeutic or prophylactic agent of any one of items 1 to 14, wherein the agent is provided while being mixed with a retinal pigment epithelial cell, and at least one agent selected from the group consisting of laminins and fragments thereof is injected under a retina thereby being contacted with cells and/or tissue constituting the retina.

(16) The therapeutic or prophylactic agent of any one of items 1 to 15, further comprising a ROCK inhibitor.

(17) The therapeutic or prophylactic agent of item 16, wherein the ROCK inhibitor is selected from the group consisting of Y-27632 ((R)-(+)-trans (4-pyridyl)-4-(1-aminoethyl) cyclohexanecarboxamide dihydrochloride monohydrate) and a pharmaceutically acceptable salt thereof.
(18) The therapeutic or prophylactic agent of any one of items 15-17, wherein the agent mixed with a cell is about 2.1 nM or greater, and the agent to be injected is about 21 nM or greater.
(19) At least one agent selected from the group consisting of laminins and fragments thereof for therapy or prophylaxis of a disease, a disorder, or a condition of a retinal pigment epithelium, wherein the laminins comprise a γ1 chain.
(20) The agent of item 19, further comprising a feature described in one or more of items 2 to 18.
(21) A method for therapy or prophylaxis of a disease, a disorder, or a condition of a retinal pigment epithelium, the method comprising administering an effective amount of at least one agent selected from the group consisting of laminins and fragments thereof to a subject in need of the therapy or prophylaxis, wherein the laminins comprise a γ1 chain.
(22) The method of item 21, further comprising a feature described in one or more of items 2 to 7.
(23) The method of item 21 or 22, further comprising administering a retinal pigment epithelial cell to the subject.
(24) The method of any one of items 21 to 23, further comprising administering a ROCK inhibitor to the subject.
(25) The method of item 24, wherein the ROCK inhibitor is selected from the group consisting of Y-27632 ((R)-(+)-trans-(4-pyridyl)-4-(1-aminoethyl) cyclohexanecarboxamide dihydrochloride monohydrate) and a pharmaceutically acceptable salt thereof.
(26) The method of any one of items 21 to 25, further comprising administering a retinal pigment epithelial cell and a ROCK inhibitor to the subject.
(27) The method of any one of items 21 to 26, wherein the agent is injected under a retina thereby being contacted with cells and/or tissue constituting the retina.
(28) The method of any one of items 21 to 27, wherein the agent is present at about 21 nM or greater.
(29) The method of any one of items 21 to 28, further comprising administering a retinal pigment epithelial cell separately from the agent.
(30) The method of any one of items 21 to 29, wherein the agent is provided while being mixed with a retinal pigment epithelial cell, and at least one agent selected from the group consisting of laminins and fragments thereof is injected under a retina thereby being contacted with cells and/or tissue constituting the retina.
(31) The method of any one of items 21 to 30, further comprising administering a ROCK inhibitor separately from the agent.
(32) The method of item 31, wherein the ROCK inhibitor is selected from the group consisting of Y-27632 ((R)-(+)-trans-(4-pyridyl)-4-(1-aminoethyl)-cyclohexanecarboxamide dihydrochloride monohydrate) and a pharmaceutically acceptable salt thereof.
(33) The method of any one of items 21 to 33, wherein the agent mixed with a cell is about 2.1 nM or greater, and the agent to be injected is about 21 nM or greater.
(34) Use of at least one agent selected from the group consisting of laminins and fragments thereof in the manufacture of a medicament for therapy or prophylaxis of a disease, a disorder, or a condition of a retinal pigment epithelium, wherein the laminins comprise a γ1 chain.
(35) Use of item 34, further comprising the feature of one or more of items 2 to 18.
(36) Use of at least one agent selected from the group consisting of laminins and fragments thereof for therapy or prophylaxis of a disease, a disorder, or a condition of a retinal pigment epithelium, wherein the laminins comprise a γ1 chain.
(37) Use of item 36, further comprising a feature described in one or more of items 2 to 18.

<Nerves>

(A1) A therapeutic or prophylactic agent for a disease, a disorder, or a condition of a nerve requiring cell transplantation, comprising at least one agent selected from the group consisting of laminin 511 and fragments thereof.
(A2) The therapeutic or prophylactic agent of item A1, wherein the fragments have cell adhesion capability of a nerve cell.
(A3) The therapeutic or prophylactic agent of item A1 or A2, wherein the agent is laminin 511 or a laminin 511-E8 fragment.
(A4) The therapeutic or prophylactic agent of any one of items A1 to A3, wherein the nerve is from a primate.
(A5) The therapeutic or prophylactic agent of any one of items A1 to A4, wherein the disease, disorder, or condition of the nerve requiring cell adhesion is selected from the group consisting of retinitis pigmentosa, macular degeneration, Stargardt disease, glaucoma, optic neuropathy, spinal cord injury, peripheral neuropathy, Parkinson's disease, Huntington's disease, and diseases resulting in a cerebral disorder.
(A6) The therapeutic or prophylactic agent of any one of items A1 to A5, further comprising a nerve cell.
(A7) The therapeutic or prophylactic agent of any one of items A1 to A6, further comprising a ROCK inhibitor.
(A8) The therapeutic or prophylactic agent of item A7, wherein the ROCK inhibitor is selected from the group consisting of Y-27632 ((R)-(+)-trans-(4-pyridyl)-4-(1-aminoethyl) cyclohexanecarboxamide dihydrochloride monohydrate) and a pharmaceutically acceptable salt thereof.
(A9) The therapeutic or prophylactic agent of any one of items A1 to A8, further comprising a nerve cell and a ROCK inhibitor.
(A10) The therapeutic or prophylactic agent of any one of items A1 to A9, wherein the agent is injected into a site on the nerve thereby being contacted with cells and/or tissue constituting the nerve.
(A11) The therapeutic or prophylactic agent of any one of items A1 to A10, wherein the agent is present at about 21 nM or greater.
(A12) The therapeutic or prophylactic agent of any one of items A1 to A11, wherein a nerve cell is further administered.
(A13) The therapeutic or prophylactic agent of any one of items A1 to A12, wherein the agent is provided while being mixed with a nerve cell, and at least one agent selected from the group consisting of laminins and fragments thereof is injected into a site on the nerve thereby being contacted with cells and/or tissue constituting the nerve.
(A14) The therapeutic or prophylactic agent of any one of items A1 to A13, further comprising a ROCK inhibitor.
(A15) The therapeutic or prophylactic agent of item A14, wherein the ROCK inhibitor is selected from the group consisting of Y-27632 ((R) (+)-trans (4-pyridyl)-4-(1-aminoethyl)-cyclohexanecarboxamide dihydrochloride monohydrate) and a pharmaceutically acceptable salt thereof.
(A16) The therapeutic or prophylactic agent of any one of items A1 to A15, wherein the agent mixed with a cell is about 2.1 nM or greater, and the agent to be injected is about 21 nM or greater.

(A17) At least one agent selected from the group consisting of laminin 511 and fragments thereof for therapy or prophylaxis of a disease, a disorder, or a condition of a nerve requiring cell transplantation.

(A18) The agent of item A17, further comprising a feature described in one or more of items A2 to A16.

(A19) A method for therapy or prophylaxis of a disease, a disorder, or a condition of a nerve requiring cell transplantation, the method comprising administering an effective amount of at least one agent selected from the group consisting of laminin 511 and fragments thereof to a subject in need of the therapy or prophylaxis.

(A20) The method of item A19, further comprising a feature described in one or more of items A2 to A5.

(A21) The method of item A19 to A20, further comprising administering a nerve cell to the subject.

(A22) The method of any one of items A19 to A21, further comprising administering a ROCK inhibitor to the subject.

(A23) The method of item A22, wherein the ROCK inhibitor is selected from the group consisting of Y-27632 ((R)-(+)-trans-(4-pyridyl)-4-(1-aminoethyl)-cyclohexanecarboxamide dihydrochloride monohydrate) and a pharmaceutically acceptable salt thereof.

(A24) The method of any one of items A19 to A23, further comprising administering a nerve cell and a ROCK inhibitor to the subject.

(A25) The method of any one of items A19 to A24, wherein the agent is injected into a site on the nerve thereby being contacted with cells and/or tissue constituting the nerve.

(A26) The method of any one of items A19 to A25, wherein the agent is present at about 21 nM or greater.

(A27) The method of any one of items A19 to A26, wherein a nerve cell is further administered.

(A28) The method of any one of items A19 to A27, wherein the agent is provided while being mixed with a nerve cell, and at least one agent selected from the group consisting of laminins and fragments thereof is injected into a site on the nerve thereby being contacted with cells and/or tissue constituting the nerve.

(A29) The method of any one of items A19 to A28, further comprising administering a ROCK inhibitor separately from the agent.

(A30) The method of item A29, wherein the ROCK inhibitor is selected from the group consisting of Y-27632 ((R)-(+)-trans(4-pyridyl)-4-(1-aminoethyl)-cyclohexanecarboxamide dihydrochloride monohydrate) and a pharmaceutically acceptable salt thereof.

(A31) The method of any one of items A19 to A30, wherein the agent mixed with a cell is about 2.1 nM or greater, and the agent to be injected is about 21 nM or greater.

It is understood that one or more of the aforementioned features can further be provided as a combination in addition to the explicitly shown combinations in the present invention. Additional embodiments and advantages of the present invention are recognized by those skilled in the art who read and understand the following detailed description as needed.

Advantageous Effects of Invention

The present invention allows novel ophthalmic therapies, especially novel therapies of retinal pigment epithelial cells (especially human retinal pigment epithelial cells) and/or nerves. In particular, the present invention provides a novel therapeutic approach for retinal disorders such as age-related macular degeneration and/or neuropathy. A significant effect is achieved in that the present invention can be applied to a form of regenerative medicine, i.e., cell transplantation, for a nerve related cell, tissue, or organ. For example, as another embodiment, this can be applied in transplantation which uses cells formed in the shape of an organ or a sheet. Thus, the present invention is recognized as achieving an effect on nerves, which was not expected from the effect on cell growth.

BRIEF DESCRIPTION OF DRAWINGS

FIG. 1 shows, from the left, control, laminin α1β1γ1, laminin α2β1γ1, laminin α4β1γ1, laminin α5β1γ1 laminin α5β2γ1, laminin α3β3γ2, FNC Coating Mix® (Athena Environmental Sciences, Inc., Baltimore, MD), laminin α5β1γ1 E8 fragment, and collagen. * indicates $p<0.01$. Dunnett's test was used as the test with n=6. The coating conditions were the following. After laminin 511, laminin 521, and laminin 211 (Biolamina) coating had been applied for 2 hours in a culture dish at 20 μg/ml and laminin 511-E8 (Nippi) coating had been applied for 3 hours in a culture dish at 5 μg/ml, monkey retinal pigment epithelial cells were seeded at a density of 5000 cells/cm$^2$, and the adhering cell count was measured with CellTiter-Glo® Luminescent Cell Viability Assay (Promega Corporation, Madison, WI) after 24 hours.

FIG. 2 shows, from the left, control, laminin α5β1γ1, and a laminin α5β1γ1-E8 fragment (herein, also referred to as "E8"). The bar indicates 100 μm.

FIG. 5 shows pictures of nerve cells (N2a) upon adding a laminin to a medium from a phase contrast microscope. The top left picture shows the result for a control, the top right pictures shows the result for a laminin 511-E8 fragment, the bottom left picture shows the result for collagen type IV, and the bottom right picture shows the result for fibronectin. The bar indicates 100 μm. The pictures were taken three hours after adding a laminin. The cells were seeded at 5000 cells/96-well plate. The laminin was added so that the final concentration was 2.1 nM in the medium.

FIG. 6 shows the effect of adding a laminin to a medium on adhesion of nerve cells (N2a). Cell adhesion was measured using an approach of counting cells that adhered. The cells were seeded at 5000 cells/96-well plate after adding E8 fragments, collagen type IV, and fibronectin with a final concentration of 2.1 nM in the medium. The adhering cell count was measured with CellTiter-Glo®) Luminescent Cell Viability Assay (Promega Corporation, Madison, WI) after 3 hours. Dunnett s test was used for statistical processing. * indicates p<0.01 and ** indicates p<0.05.

FIG. 7 shows pictures of nerve cells (SH-SY5Y) upon adding a laminin to a medium from a phase contrast microscope. The top left picture shows the result for a control, the top right picture shows the result for a laminin 511-E8 fragment, the bottom left picture shows the result for collagen type IV, and the bottom right picture shows the result for fibronectin. The bar indicates 100 μm. The pictures were taken 3 hours after adding laminin 511-E8 fragments, collagen type IV, and fibronectin at 2.1 nM and seeding. The cells were seeded at 5000 cells/96-well plate.

FIG. 8 shows an effect of adding a laminin to a medium on adhesion of nerve cells (SH-SY5Y). Cell adhesion was measured using an approach of counting cells that adhered. The cells were seeded at 5000 cells/96-well plate after adding ES fragments, collagen type IV, and fibronectin with a final concentration of 2.1 nM in the medium. The adhering cell count was measured with CellTiter-Glo® Luminescent Cell Viability Assay (Promega Corporation, Madison, WI) after 3 hours. FIG. 8 shows the result for, from the left, control, laminin 511-E8 fragment, collagen type IV, and fibronectin. The pictures are from 3 hours after adding a laminin. The cells were seeded at 5000 cells/96-well plate, and the laminin concentration used was 2.1 nM. Dunnett's test was used for statistical processing. * indicates p<0.01 and ** indicates p<0.05.

DESCRIPTION OF EMBODIMENTS

Figure 1:
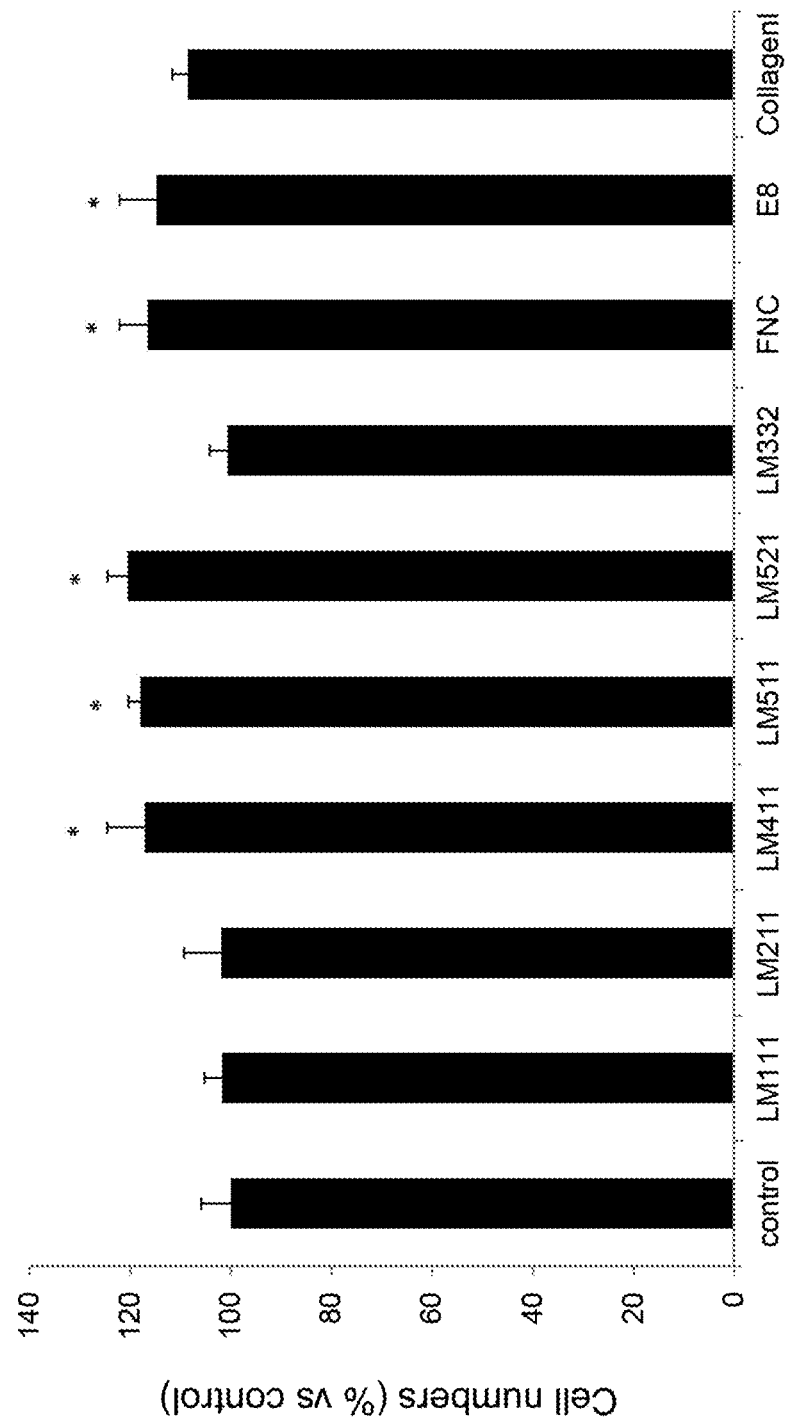
FIG. 1 shows results of studying the effect of laminin coating on cell adhesion of a retinal pigment epithelium (RPE).

The present invention is explained hereinafter. Throughout the entire specification, a singular expression should be understood as encompassing the concept thereof in the plural form unless specifically noted otherwise. Thus, singular articles (e.g., "a", "an" "the" and the like in case of English) should also be understood as encompassing the concept thereof in the plural form unless specifically noted otherwise. Further, the terms used herein should be understood as being used in the meaning that is commonly used in the art, unless specifically noted otherwise. Thus, unless defined otherwise, all terminologies and scientific technical terms that are used herein have the same meaning as the terms commonly understood by those skilled in the art to which the present invention pertains. In case of a contradiction, the present specification (including the definitions) takes precedence.

Definitions

As used herein, "retinal pigment epithelial cell" (also referred to as an RPE cell) is an epithelial cell that is present between the retina and the choroid of an eye. A retinal pigment epithelial cell has a function of forming the blood-retinal barrier, phagocytosis of the outer segment of a photoreceptor cell, visual pigment regeneration, and the like. A retina is the inner-most layer of the wall of an eye ball. A retina has photoreceptor cells and an optic nerve and senses light stimulation. It is understood that the patient's own cells collected by biopsy, cells collected from others, cultured retinal pigment epithelial cells, and cells differentiated from stem cells such as differentiated cells induced from iPS cells, ES cells or the like can be used as the retinal pigment epithelial cells used in the present invention.

As used herein, "nerve cell" is used in the meaning that is commonly used in the art and refers to any cell of a nerve. Examples of typical nerve cells include, but are not limited to, cell lines such as N2a and H-SY5Y. N2a and SH-SYSY are used in the art as exemplary nerve cells. It is understood that the patient's own cells collected by biopsy, cells collected from others, cultured nerve cells, and cells differentiated from stem cells such as differentiated cells induced from iPS cells, ES cells or the like can be used as the nerve cells used in the present invention.

As used herein, "isolated" refers to a state where a substance that naturally accompanies an entity under normal circumstances is at least reduced, and preferably a state where the entity is substantially free of such a substance. Thus, isolated cells, tissue and the like refer to cells, tissue and the like that are substantially free of other substances which accompany them (e.g., other cells, proteins, nucleic acids or the like) in a natural environment.

<Laminin>

As used herein, "laminin" is a constituent protein of a basement membrane of an extracellular matrix. Laminins promote multicellularity/tissue construct and maintenance thereof, cell adhesion, cell migration, and cell growth and have a close relationship with cancer cells. A laminin is considered to be expressed at the early stage (two-cell stage) of blastogenesis. A laminin is a heterotrimer consisting of one of each of an α chain, a β chain and a γ chain. For the naming of laminins, the nomenclature in the order of discovery (laminin-1, laminin-2, etc.) is known. However, correspondence to subunits is not considered, so that a newer naming method, in which the name of the subclass α, β, or γ (a three digit number, the digit of one hundred indicates a, the digit of ten indicates p, and the digit of one indicates γ) is described together, is employed herein. In case of α1, β1, and γ1, such a laminin is called laminin 111. For laminins, five types of a chains, 3 types of β chains and three types of γ chains have been discovered. Thus, the theoretic maximum number of combinations is 5×3×3=45, so that 45 types of laminin molecules are possible. However, it is believed that not all of the combinations exist in nature. Each subunit, for instance, is called LAMA1, LAMA2, LAMA3, LAMA4, or LAMA5 for an α chain, LAMB1, LAMB2, or LAMB3 for a β chain, and LAMC1, LAMC2, or LAMC3 for a γ chain. Laminin proteins used in the present invention may be naturally-occurring laminin proteins or those with a modified form where one or more amino acid residues are modified while retaining the biological activity thereof, especially the cell adhesion promoting activity. Further, the laminin proteins in the present invention are not limited in terms of the origin, production method thereof or the like, as long as the laminin protein has the features described herein. Thus, the laminin proteins used in the present invention may be any of naturally occurring proteins, proteins expressed from a recombinant DNA by a genetic engineering approach, or chemically synthesized proteins. The origin of the laminin proteins used in the present invention is not particularly limited, but is preferably derived from a human. When culturing a human cell for the purpose of obtaining a medical material, it is preferable, but is not limited to, using a laminin derived from a human in order to avoid the use of a material derived from another animal.

Binding molecules of a laminin are known α1β1, α2β1, α2β2, α3β1, α6β1, α6β4, α7β1, α9β1, αvβ3, αvβ5, and αvβ8 are integrins known as a laminin receptor.

The following Table describes representative laminins and the explanation thereof.

TABLE 1

| Trimer composition (name) | Main expression site | Integrin binding specificity |
| --- | --- | --- |
| α1β1γ1 (laminin-1) | Fetal tissue | α6β1 |
| α1β2γ1 (laminin-3) | | |
| α2β1γ1 (laminin-2) | Muscles, nerves (Schwann cell) | α7β1, α6β1, α3β1 |
| α2β2γ1 (laminin-4) | | |
| α2β1γ3 (laminin-12) | | |
| α3β3γ2 (laminin-5) | Skin, lung, and other epithelial tissue | α3β1, α6β4 |
| α3β1γ1 (laminin-6) | | |
| α3β2γ1 (laminin-7) | | |
| α4β1γ1 (laminin-8) | Blood vessel | α6β1, α3β1 |
| α4β2γ1 (laminin-9) | | |
| α5β1γ1 (laminin-10) | Blood vessel, liver, lung, and other epithelial tissue | α3β1, α6β1 |
| α5β2γ1 (laminin-11) | | |

As used herein, "α1 chain" (LAMA1) is a subunit of a laminin•protein of a cell adhesion molecule in an extracellular matrix, and is called LAMA1, LAMA, S-LAM-alpha, or the like. For human LAMA1, the sequences of the gene and protein are registered as NCBI registration numbers NM_005559 and NP_005550, respectively. OMIM is identified with an accession number 150320. When used for the purpose herein, it is understood that "α1 chain" or "LAMA1" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "α2 chain" (LAMA2) is a subunit of a laminin•protein of a cell adhesion molecule in an extracellular matrix, and is called LAMA2, LAMM, or the like. For human LAMA2, the sequences of the gene and protein are registered as NCBI registration numbers NM_000426 and NP_000417, respectively. OMIM is identified with an accession number 156225. When used for the purpose herein, it is understood that "α2 chain" or "LAMA2" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "α3 chain" (LAMA3) is a subunit of a laminin•protein of a cell adhesion molecule in an extracellular matrix, and is called LAMA3, BM600, E170, LAMNA, LOCS, lama3a, or the like. For human LAMA3, the sequences of the gene and protein are registered as NCBI registration numbers NM_000227 and NP_000218, respectively. OMIM is identified with an accession number 600805. When used for the purpose herein, it is understood that "α3 chain" or "LAMA3" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "α4 chain" (LAMA4) is a subunit of a laminin•protein of a cell adhesion molecule in an extracellular matrix, and is called LAMA4, LAMA3, LAMA4*-1, CMD1JJ or the like. For human LAMA4, the sequences of the gene and protein are registered as NCBI registration numbers NM_001105206 and Np_001098676, respectively. OMIM is identified with an accession number 600133. When used for the purpose herein, it is understood that "α4 chain" or "LAMA4" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used, herein, "α5 chain" (LAMA5) is a subunit of a laminin•protein of a cell adhesion molecule in an extracellular matrix, and is called LAMA5, KIAA1907, or the like. For human LAMA5, the sequences of the gene and protein are registered as NCBI registration numbers NM_005560 and NP_005551, respectively. OMIM is identified with an accession number 601033. When used for the purpose herein, it is understood that "α5 chain" or "LAMA5" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "β1 chain" (LAMB1) is a subunit of a laminin•protein of a cell adhesion molecule in an extracellular matrix, and is called LAMB1, CLM, LIS5, or the like. For human LAMB1, the sequences of the gene and protein are registered as NCBI registration numbers NM_002291 and NP_002282, respectively. OMIM is identified with an accession number 150240. When used for the purpose herein, it is understood that "β1 chain" or "LAMB1" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "β2 chain" (LAMB2) (laminin S) is a subunit of a laminin•protein of a cell adhesion molecule in an extracellular matrix, and is called LAMB2, LAMS, NPHS5, or the like. For human LAMB2, the sequences of the gene and protein are registered as NCBI registration numbers NM_002292 and NP_002283, respectively. OMIM is identified with an accession number 150325. When used for the purpose herein, it is understood that "β2 chain" or "LAMB2" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "β3 chain" (LAMB3) is a subunit of a laminin•protein of a cell adhesion molecule in an extracellular matrix, and is called LAMB3, BM600-125KDA, LAM5, LAMNB1, or the like. For human LAMB3, the sequences of the gene and protein are registered as NCBI registration numbers NM 000228 and NP_000219, respectively. OMIM is identified with an accession number 150310. When used for the purpose herein, it is understood that "β3 chain" or "LAMB3" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "γ1 chain" (LAMC1) is a subunit of a laminin•protein of a cell adhesion molecule in an extracellular matrix, and is called LAMC1, LAMB2, or the like. For human LAMC1, the sequences of the gene and protein are registered as NCBI registration numbers NM_002293 and NP_002284, respectively. OMIM is identified with an accession number 150290. When used for the purpose herein, it is understood that "γ1 chain" or "LAMC1" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "γ2 chain" (LAMC2) is a subunit of a laminin•protein of a cell adhesion molecule in an extracellular matrix, and is called LAMC2, B2T, BM600, CSF, EBR2, EBR2A, LAMB2T, LAMNB2, or the like. For human LAMC2, the sequences of the gene and protein are registered as NCBI registration numbers NM_005562 and NP_005553, respectively. OMIM is identified with an accession number 150292. When used for the purpose herein, it is understood that "γ2 chain" or "LAMC2" means not only a protein having an amino acid sequence set forth in a specific sequence number or accession (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "γ3 chain" (LAMC3) is a subunit of a laminin•protein of a cell adhesion molecule in an extracellular matrix, and is called LAMC3, OCCM, or the like. For human LAMC3, the sequences of the gene and protein are registered as NCBI registration numbers NM_006059 and NP_006050, respectively. OMIM is identified with an accession number 604349. When used for the purpose herein, it is understood that "γ3 chain" or "LAMC3" means not only a protein having an amino acid sequence set forth in a specific sequence number or accession number (or a nucleic acid encoding the protein), but also a functionally active derivative, a functionally active fragment, or a homologue thereof, or a mutant encoded by a nucleic acid that hybridizes to a nucleic acid encoding the protein under a high or low stringency condition.

As used herein, "expression" of a gene, polynucleotide, polypeptide or the like refers to the gene or the like being subjected to a certain effect in vivo to be in another form. Preferably, the expression refers to a gene, polynucleotide or the like being transcribed and translated to be in a form of a polypeptide, but transcription resulting in mRNA can also be one form of expression. More preferably, such a polypeptide form can be those subjected to post-translation processing (referred to as a derivative herein). For example, the expression level of each laminin chain can be determined by any method. Specifically, the expression level of each laminin chain can be found by evaluating the amount of mRNA of each laminin chain, amount of protein of each laminin chain, or biological activity of the protein of each laminin chain. The amount of mRNA or protein of each laminin chain can be determined by a method as described herein.

As used herein, "functional equivalent" refers to anything that has the same function of interest but a different structure with respect to the original entity. Thus, it is understood that "a laminin or each laminin chain, or a functional equivalent thereof" or a "group consisting of a laminin, each laminin chain, and a functional equivalent thereof" encompasses a laminin or each laminin chain itself, as well as fragments, mutants, or variants of the laminin or each laminin chain (e.g., amino acid sequence variant or the like) having one or more of cell adhesion capability, differentiation controlling and/or growth promoting action on an eye cell or the like, and substances that can change into a laminin or each laminin chain itself, or a fragment mutant, or variant of the laminin or each laminin chain at the time of action (including, for example, nucleic acids encoding a laminin or each laminin chain itself or a fragment, mutant, or variant of the laminin or each laminin chain, vectors and cells comprising such a nucleic acid, and the like). Typical examples of "a laminin or each laminin chain, or a functional equivalent thereof" or a "group consisting of a laminin, each laminin chain, and a functional equivalent thereof" include at least one agent selected from the group consisting of laminins and fragments thereof. In the present invention, it is understood that a functional equivalent of a laminin or each laminin chain can be used in the same manner as the laminin or each laminin chain without any specific mention thereof.

As used herein, "fragment" refers to a polypeptide or a polynucleotide with a sequence length of 1 to n-1 with respect to the full length polypeptide or polynucleotide (with length n). The length of a fragment can be appropriately changed in accordance with the objective. For a polypeptide, examples of the lower limit of the length thereof include 3, 4, 5, 6, 7, 8, 9, 10, 15, 20, 25, 30, 40, 50 and more amino acids. Lengths represented by an integer that is not specifically listed herein (e.g. 11 and the like) can also be appropriate as the lower limit. For a polynucleotide, examples of the lower limit of the length thereof include 5, 6, 7, 8, 9, 10, 15, 20, 25, 30, 40, 50, 75, 100 and more nucleotides. Lengths represented by an integer that is not specifically listed herein (e.g. 11 and the like) can also be appropriate as the lower limit. It is understood herein that fragments themselves of such a laminin chain, when functioning as a factor of activity thereof, e.g., growth promotion or maintenance, are within the scope of the present invention. According to the present invention, the term "activity" as used herein refers to a function of a molecule in the broadest meaning. Activity generally encompasses, but is not intended to be limited to, biological function, biochemical function, physical function, and chemical function of a molecule. Examples of activity include enzymatic activity, ability to interact with another molecule, ability to activate, promote, stabilize, inhibit, suppress, or destabilize a function of another molecule, stability, and ability to localize at a specific position in a cell. When applicable, the term is also directed to a function of a protein complex in the broadest sense. As used herein, "biological function", with regard to a gene or a nucleic acid or polypeptide related thereto, refers to a specific function that the gene, nucleic acid or polypeptide can have in a living body. Examples thereof include, but are not limited to, production of a specific antibody, enzymatic activity, impartation of resistance, and the like. As used herein, biological function can be exerted by "biological activity". As used herein, "biological activity" refers to activity that a certain agent (e.g., polynucleotide, protein, or the like) can have in a living body, including activity exerting a variety of functions (e.g., transcription promoting activity) such as the activity of activating or deactivating a molecule from interaction with another molecule. When two agents interact, the biological activity thereof can be thought of as the bond between the two molecules and the biological change resulting therefrom, e.g., the two molecules are bound when precipitation of one of the molecules with an antibody results in co-precipitation of the other molecule. Thus, one method of determination includes observing such co-precipitation. When an agent is for instance an enzyme, the biological activity thereof encompasses the enzymatic activity thereof. Another example includes binding of a ligand to a corresponding receptor when an agent is a ligand. Such biological activity can be measured by a well-known technique in the art. Thus, "activity" refers to various measurable indicators that indicate or reveal the bond (either directly or indirectly) or affects a response (i.e., having a measurable effect in response to some exposure or stimulation). Examples thereof include the affinity of a compound that directly binds to the polypeptide or polynucleotide of the present invention, the amount of proteins upstream or downstream after some exposure or stimulation, and a dimension of another similar function.

"Functionally active" as used herein refers to a polypeptide, a fragment, or a derivative having a structural function, controlling function, or biochemical function of a protein such as biological activity in accordance with the embodiment associated with the polypeptide, fragment or derivative of the invention.

As used herein, a "fragment" of a laminin refers to any fragment of a laminin. As an agent used in the present invention, it is understood that not only the full length laminin, but also a fragment of the laminin can be used, as long as the fragment has the function of the full length laminin, particularly the cell adhesion capability of an endothelial cell. Thus, a fragment of a laminin used in the present invention generally has at least one function of the laminin. Such a function can encompass cell adhesion capability of an endothelial cell in particular.

The sequence of a laminin found to be expressed in retinal pigment epithelial cells and/or nerves in the present invention will be explained. It is understood that these laminins are preferred representative examples of the present invention and the present invention is not limited to these specific laminin subtypes.

A typical nucleotide sequence of a laminin α5 chain can be:
(a) a polynucleotide having the base sequence set forth in SEQ ID NO: 1 or a fragment sequence thereof;
(b) a polynucleotide encoding a polypeptide consisting of the amino acid sequence set forth in SEQ ID NO: 2 or a fragment thereof;
(c) a polynucleotide encoding a variant polypeptide or a fragment thereof having one or more amino acids with a mutation selected from the group consisting of a substitution, an addition, and a deletion in the amino acid sequence set forth in SEQ ID NO: 2, wherein the variant polypeptide has biological activity;
(d) a polynucleotide which is an allele or a splice mutant of the base sequence set forth in SEQ ID NO: 1 or a fragment thereof;
(e) a polynucleotide encoding a species homolog of a polypeptide consisting of the amino acid sequence set forth in SEQ ID NO: 2 or a fragment thereof;
(f) a polynucleotide encoding a polypeptide having biological activity and hybridizing with a polynucleotide of one of (a) to (e) under a stringent condition; or
(g) a polynucleotide encoding a polypeptide having biological activity and consisting of a base sequence with identity of at least about 70%, at least about 80%, at least about 90%, at least about 95%, at least about 96%, at least about 97%, at least about 98%, or at least about 99% to a polynucleotide of one of (a) to (e) or a complementary sequence thereof. In this regard, biological activity typically refers to activity of a laminin α5 chain. Doi M et al., J. Biol. Chem. 277(15), 12741-12748, 2002 and U.S. Pat. No. 6,933,273 can be referenced with regard to α5 chains.

An amino acid sequence of a laminin α5 chain can be:
(a) a polypeptide consisting of the amino acid sequence set forth in SEQ ID NO: 2 or a fragment thereof;
(b) a polypeptide having biological activity and one or more amino acids with a mutation selected from the group consisting of a substitution, an addition and a deletion in the amino acid sequence set forth in SEQ ID NO: 2;
(c) a polypeptide encoded by an allele or a splice mutant of the base sequence set forth in SEQ ID NO: 1;
(d) a polypeptide which is a species homolog of the amino acid sequence set forth in SEQ ID NO: 2; or
(e) a polypeptide having biological activity and an amino acid sequence with identity of at least about 70%, at least about 80%, at least about 90%, at least about 95%, at least about 96%, at least about 97%, at least about 98%, or at least about 99% to a polypeptide of one of (a) to (d). In this regard, biological activity typically refers to the activity of a laminin α5 chain. Doi M et al., J. Biol. Chem. 277 (15), 12741-12748, 2002 and U.S. Pat. No. 6,933,273 can be referenced with regard to α5 chains.

A typical nucleotide sequence of a laminin 4 chain can be:
(a) a polynucleotide having the base sequence set forth in SEQ ID NO: 3 or a fragment sequence thereof;
(b) a polynucleotide encoding a polypeptide consisting of the amino acid sequence set forth in SEQ ID NO: 4 or a fragment thereof;
(c) a polynucleotide encoding a variant polypeptide or a fragment thereof having one or more amino acids with a mutation selected from the group consisting of a substitution, an addition, and a deletion in the amino acid sequence set forth in SEQ ID NO: 4, wherein the variant polypeptide has biological activity;
(d) a polynucleotide which is an allele or a splice mutant of the base sequence set forth in SEQ ID NO: 3 or a fragment thereof;
(e) a polynucleotide encoding a species homolog of a polypeptide consisting of the amino acid sequence set forth in SEQ ID NO: 4 or a fragment thereof;
(f) a polynucleotide encoding a polypeptide having biological activity and hybridizing with a polynucleotide of one of (a) to (e) under a stringent condition; or
(g) a polynucleotide encoding a polypeptide having biological activity and consisting of a base sequence with identity of at least about 70%, at least about 80%, at least about 90%, at least about 95%, at least about 96%, at least about 97%, at least about 98%, or at least about 99% to a polynucleotide of one of (a) to (e) or a complementary sequence thereof. In this regard, biological activity typically refers to activity of a laminin β1 chain. Pillarainen et al., J. Biol. Chem. 262 (22), 10454-10462, 1987 and U.S. Pat. No. 6,933,273 can be referenced with regard to β1 chains.

An amino acid sequence of a laminin β1 chain can be:
(a) a polypeptide consisting of the amino acid sequence set forth in SEQ ID NO: 4 or a fragment thereof;

(b) a polypeptide having biological activity and one or more amino acids with a mutation selected from the group consisting of a substitution, an addition, and a deletion in the amino acid sequence set forth in SEQ ID NO: 4;
(c) a polypeptide encoded by an allele or a splice mutant of the base sequence set forth in SEQ ID NO: 3;
(d) a polypeptide which is a species homolog of the amino acid sequence set forth in SEQ ID NO: 4; or
(e) a polypeptide having biological activity and an amino acid sequence with identity of at least about 70%, at least about 80%, at least about 90%, at least about 95%, at least about 96%, at least about 97%, at least about 98%, or at least about 99% to a polypeptide of one of (a) to (d). In this regard, biological activity typically refers to activity of a laminin β1 chain. Pillarainen et al., J. Biol. Chem. 262 (22), 10454-10462, 1987 and U.S. Pat. No. 6,933,273 can be referenced with regard to β1 chains.

A typical nucleotide sequence of a laminin β2 chain can be:
(a) a polynucleotide having the base sequence set forth in SEQ ID NO: 5 or a fragment sequence thereof;
(b) a polynucleotide encoding a polypeptide consisting of the amino acid sequence set forth in SEQ ID NO: 6 or a fragment thereof;
(c) a polynucleotide encoding a variant polypeptide or a fragment thereof having one or more amino acids with a mutation selected from the group consisting of a substitution, an addition, and a deletion in the amino acid sequence set forth in SEQ ID NO: 6, wherein the variant polypeptide has biological activity;
(d) a polynucleotide which is an allele or a splice mutant of the base sequence set forth in SEQ ID NO: 5 or a fragment thereof;
(e) a polynucleotide encoding a species homolog of a polypeptide consisting of the amino acid sequence set forth in SEQ ID NO: 6 or a fragment thereof;
(f) a polynucleotide encoding a polypeptide having biological activity and hybridizing with a polynucleotide of one of (a) to (e) under a stringent condition; or
(g) a polynucleotide encoding a polypeptide having biological activity and consisting of a base sequence with identity of at least about 70%, at least about 80%, at least about 90%, at least about 95%, at least about 96%, at least about 97%, at least about 98%, or at least about 99% to a polynucleotide of one of (a) to (e) or a complementary sequence thereof. In this regard, biological activity typically refers to the activity of a laminin β2 chain. Wewer U M et al., Genomics. Nov. 15, 1994; 24(2): 243-52., 1987 and U.S. Pat. No. 6,933,273 can be referenced with regard to β2 chains.

An amino acid sequence of a laminin β2 chain can be:
(a) a polypeptide consisting of the amino acid sequence set forth in SEQ ID NO: 6 or a fragment thereof;
(b) a polypeptide having biological activity and one or more amino acids with a mutation selected from the group consisting of a substitution, an addition, and a deletion in the amino acid sequence set forth in SEQ ID NO: 6;
(c) a polypeptide encoded by an allele or a splice mutant of the base sequence set forth in SEQ ID NO: 5;
(d) a polypeptide which is a species homolog of the amino acid sequence set forth in SEQ ID NO: 6; or
(e) a polypeptide having biological activity and an amino acid sequence with identity of at least about 70%, at least about 80%, at least about 90%, at least about 95%, at least about 96%, at least about 97%, at least about 98%, or at least about 99% to a polypeptide of one of (a) to (d). In this regard, biological activity typically refers to the activity of a laminin β2 chain. Wewer U M et al., Genomics. Nov. 15, 1994; 24(2): 243-52., 1987 and U.S. Pat. No. 6,933,273 can be referenced with regard to β2 chains.

A typical nucleotide sequence of a laminin γ1 chain can be:
(a) a polynucleotide having the base sequence set forth in SEQ ID NO: 7 or a fragment sequence thereof;
(b) a polynucleotide encoding a polypeptide consisting of the amino acid sequence set forth in SEQ ID NO: 8 or a fragment thereof;
(c) a polynucleotide encoding a variant polypeptide or a fragment thereof having one or more amino acids with a mutation selected from the group consisting of a substitution, an addition, and a deletion in the amino acid sequence set forth in SEQ ID NO: 8, wherein the variant polypeptide has biological activity;
(d) a polynucleotide which is an allele or a splice mutant of the base sequence set forth in SEQ ID NO: 7 or a fragment thereof;
(e) a polynucleotide encoding a species homolog of a polypeptide consisting of the amino acid sequence set forth in SEQ ID NO: 8 or a fragment thereof;
(f) a polynucleotide encoding a polypeptide having biological activity and hybridizing with a polynucleotide of one of (a) to (e) under a stringent condition; or
(g) a polynucleotide encoding a polypeptide having biological activity and consisting of a base sequence with identity of at least about 70%, at least about 80%, at least about 90%, at least about 95%, at least about 96%, at least about 97%, at least about 98%, or at least about 99% to a polynucleotide of one of (a) to (e) or a complementary sequence thereof. In this regard, biological activity typically refers to activity of a laminin γ1 chain. Pillarainen et al., J. Biol. Chem. 263 (14), 6751-6758, 1988 and U.S. Pat. No. 6,933,273 can be referenced for γ1 chains.

An amino acid sequence of a laminin γ1 chain can be:
(a) a polypeptide consisting of the amino acid sequence set forth in SEQ ID NO: 8 or a fragment thereof;
(b) a polypeptide having biological activity and one or more amino acids with a mutation selected from the group consisting of a substitution, an addition, and a deletion in the amino acid sequence set forth in SEQ ID NO: 8;
(c) a polypeptide encoded by an allele or a splice mutant of the base sequence set forth in SEQ ID NO: 7;
(d) a polypeptide which is a species homolog of the amino acid sequence set forth in SEQ ID NO: 8; or
(e) a polypeptide having biological activity and an amino acid sequence with identity of at least about 70%, at least about 80%, at least about 90%, at least about 95%, at least about 96%, at least about 97%, at least about 98%, or at least about 99% to a polypeptide of one of (a) to (d). In this regard, biological activity typically refers to the activity of a laminin γ1 chain. Pillarainen et al., J. Biol. Chem. 263 (14), 6751-6758, 1988 and U.S. Pat. No. 6,933,273 can be referenced with regard to γ1 chains.

A typical nucleotide sequence of a laminin all chain can be:
(a) a polynucleotide having the base sequence set forth in SEQ ID NO: 9 or a fragment sequence thereof;
(b) a polynucleotide encoding a polypeptide consisting of the amino acid sequence set forth in SEQ ID NO: 10 or a fragment thereof;
(c) a polynucleotide encoding a variant polypeptide or a fragment thereof having one or more amino acids with a mutation selected from the group consisting of a substitution, an addition, and a deletion in the amino acid sequence set forth in SEQ ID NO: 10, wherein the variant polypeptide has biological activity;

(d) a polynucleotide which is an allele or a splice mutant of the base sequence set forth in SEQ ID NO: 9 or a fragment thereof;
(e) a polynucleotide encoding a species homolog of a polypeptide consisting of the amino acid sequence set forth in SEQ ID NO: 10 or a fragment thereof;
(f) a polynucleotide encoding a polypeptide having biological activity and hybridizing with a polynucleotide of one of (a) to (e) under a stringent condition; or
(g) a polynucleotide encoding a polypeptide having biological activity and consisting of a base sequence with identity of at least about 70%, at least about 80%, at least about 90%, at least about 95%, at least about 96%, at least about 97%, at least about 98%, or at least about 99% to a polynucleotide of one of (a) to (e) or a complementary sequence thereof. In this regard, biological activity typically refers to activity of a laminin α4 chain. For α4 chains, typical examples thereof include adhesion promoting activity of retinal pigment epithelial cells when combining a β1 chain and a γ1 chain and the like.

An amino acid sequence of a laminin α4 chain can be:
(a) a polypeptide consisting of the amino acid sequence set forth in SEQ ID NO: 10 or a fragment thereof;
(b) a polypeptide having biological activity and one or more amino acids with a mutation selected from the group consisting of a substitution, an addition, and a deletion in the amino acid sequence set forth in SEQ ID NO: 10;
(c) a polypeptide encoded by an allele or a splice mutant of the base sequence set forth in SEQ ID NO: 9;
(d) a polypeptide which is a species homolog of the amino acid sequence set forth in SEQ ID NO: 10; or
(e) a polypeptide having biological activity and an amino acid sequence with identity of at least about 70%, at least about 80%, at least about 90%, at least about 95%, at least about 96%, at least about 97%, at least about 98%, or at least about 99% to a polypeptide of one of (a) to (d). In this regard, biological activity typically refers to the activity of a laminin α4 chain. For α4 chains, typical examples thereof include adhesion promoting activity of retinal pigment epithelial cells when combining a η1 chain and a γ1 chain and the like.

As used herein, "protein", "polypeptide", "oligopeptide" and "peptide" are interchangeably used in the same meaning, referring to a polymer of amino acids of any length. Such a polymer may be a linear chain, a branched chain, or a cyclic chain. Amino acids may be naturally-occurring, non-naturally occurring, or altered amino acids. This term may also encompass those assembled into a complex of multiple polypeptide chains. This term also encompasses naturally or artificially-altered amino acid polymers. Examples of such an alteration include disulfide bond formation, glycosylation, lipidation, acetylation, phosphorylation, and any other operation or alteration (e.g., conjugation with a label component). This definition also encompasses, for example, polypeptides comprising one or more analogs of amino acids (e.g., including non-naturally-occurring amino acids and the like), peptide-like compounds (e.g., peptoid), and other alterations known in the art. For the protein of the invention (e.g., each laminin chain), a DNA encoding each chain gene of interest can be incorporated into an appropriate vector and introduced into a eukaryotic or prokaryotic cell using an expression vector which can be expressed in the respective host, and respective chains are expressed to obtain a desired protein. Host cells that can be used to express a laminin are not particularly limited. Examples thereof include prokaryotic host cells, such as *E. coli* and *Bacillus subtilis*, and eukaryotic host cells such as yeast, fungi, insect cells, plants and plant cells, and mammalian cells. Vectors constructed to express a laminin chain of interest or the like can be introduced into the aforementioned host cells, using transformation, transfection, conjugation, protoplast fusion, electroporation, particle gun technique, calcium phosphate precipitation, Agrobacterium method, direct microinjection or the like. Cells comprising a vector are grown in an appropriate culture medium to produce a laminin chain or the like used in the present invention, then the laminin chain is purified from the cells or culture medium to obtain the laminin chain or the like. The purification can be performed using size exclusion chromatography, HPLC, ion exchange chromatography, immunoaffinity chromatography, or the like.

As used herein, "amino acid" may be naturally occurring or non-naturally occurring, as long as the objective of the present invention is met.

As used herein, "polynucleotide", "oligonucleotide", and "nucleic acid" are interchangeably used in the same meaning, referring to a polymer of nucleotides of any length. These terms also encompass "oligonucleotide derivative" and "polynucleotide derivative". The "oligonucleotide derivative" and "polynucleotide derivative" are interchangeably used and refer to an oligonucleotide or polynucleotide which comprises a derivative of a nucleotide or an oligonucleotide or polynucleotide with a bond between nucleotides that is different from normal bonds. Specific examples of such oligonucleotides include: 2'-O-methyl-ribonucleotide; oligonucleotide derivatives with a phosphodiester bond in an oligonucleotide converted into phosphorothioate bond; oligonucleotide derivatives with a phosphodiester bond in an oligonucleotide converted into an N3'-P5' phosphoramidate bond; oligonucleotide derivatives with a ribose and a phosphodiester bond in an oligonucleotide converted into a peptide nucleic acid bond; oligonucleotide derivatives with a uracil in an oligonucleotide substituted with a C-5 propynyl uracil; oligonucleotide derivatives with uracil in an oligonucleotide substituted with a C-5 thiazole uracil; oligonucleotide derivatives with a cytosine in an oligonucleotide substituted with a C-5 propynyl cytosine; oligonucleotide derivatives with a cytosine in an oligonucleotide substituted with a phenoxazine-modified cytosine; oligonucleotide derivatives with a ribose in DNA substituted with a 2'-O-propylribose; oligonucleotide derivatives with a ribose in an oligonucleotide substituted with a 2'-methoxyethoxy ribose, and the like. Unless noted otherwise, specific nucleic acid sequences are intended to encompass sequences that are explicitly set forth, as well as their conservatively altered variants (e.g., degenerate codon substitutes) and complementary sequences. Specifically, a degenerate codon substitute can be achieved by making a sequence in which the third position of one or more selected (or all the) codons is substituted with a mixed base and/or deoxyinosine residue (Batzer et al., Nucleic Acid Res. 19: 5081 (1991); Ohtsuka et al., J. Biol. Chem. 260: 2605-2608 (1985); Rossolini et al., Mol. Cell. Probes 8: 91-98 (1994)). As used herein, "nucleic acid" is interchangeably used with gene, cDNA, mRNA, oligonucleotide, and polynucleotide. As used herein, "nucleotide" may be naturally occurring or non-naturally-occurring.

As used herein, "gene" refers to an agent that defines a genetic trait. Normally, a gene is sequenced in a given order on a chromosome. A gene that defines the primary structure of a protein is referred to as a structural gene, and a gene that affects the expression thereof is referred to as a regulator gene. Herein, "gene" may refer to a "polynucleotide", "oligonucleotide", and "nucleic acid".

Amino acids may be mentioned herein by either their commonly known three letter symbol or their one letter symbol recommended by the IUPAC-IUB Biochemical Nomenclature Commission. Similarly, nucleotides may be mentioned by their commonly recognized one letter code. Similarity, identity, and homology of an amino acid sequence and a base sequence is compared herein by calculation using a default parameter with a sequence analysis tool, BLAST. For example, identity can be searched using BLAST 2.2.26 (published on Oct. 30, 2011) of the NCBI. Herein, values for identity generally refer to a value when aligned under the default condition using the aforementioned BLAST. However, when a higher value is obtained by changing a parameter, the highest value is considered the value of identity. When identity is evaluated in multiple regions, the highest value thereamong is considered the value of identity. Similarity is a value calculated by taking into consideration a similar amino acid in addition to identity.

As used herein, "polynucleotide that hybridizes under a stringent condition" refers to well-known conditions commonly used in the art. It is understood that laminins encoded by a "polynucleotide that hybridizes under a stringent condition" to nucleic acid sequences of each specifically-disclosed laminin may also be used as the laminins used in the present invention. Such a polynucleotide can be obtained using colony hybridization, plaque hybridization, southern blot hybridization, or the like, with a polynucleotide selected from the polynucleotides of the present invention used as a probe. Specifically, this refers to a polynucleotide that can be identified by performing hybridization at 65° C. in the presence of 0.7 to 1.0M of NaCl using a filter to which a colony or plaque-derived DNA is immobilized, and then washing the filter under the condition of 65° C. with a SSC (saline-sodium citrate) solution of 0.1 to 2 fold concentration (wherein the composition of the SSC solution of one fold concentration is 150 mM sodium chloride and 15 mM sodium citrate). Hybridization can be performed according to methods described in experimental documents such as Molecular Cloning 2nd ed., Current Protocols in Molecular Biology, Supplement 1-38, DNA Cloning 1: Core Techniques, A Practical Approach, Second Edition, Oxford University Press (1995). In this regard, sequences comprising only an A sequence or a T sequence are preferably excluded from sequences that hybridize under a stringent condition. Thus, the polypeptides (e.g., transthyretin) used in the present invention also encompass polypeptides encoded by a nucleic acid molecule that hybridizes under a stringent condition to a nucleic acid molecule encoding the polypeptide specifically described in the present invention. These low stringency conditions include: performing hybridization for 18 to 20 hours at 40° C. in a buffer comprising 35% formamide, 5×SSC, 50 mM Tris-HCl (pH 7.5), 5 mM EDTA, 0.02% PVP, 0.02% BSA, 100 µg/ml denatured salmon sperm DNA, and 10% (weight/volume) dextran sulfate; washing 1 to 5 hours at 55° C. in a buffer consisting of 2×SSC, 25 mM Tris-HCl (pH 7.4), 5 mM EDTA, and 0.1% SDS; and washing for 1.5 hours at 60° C. in a buffer consisting of 2×SSC, 25 mM Tris-HCl (pH 7.4), 5 mM EDTA, and 0.1% SDS.

Functional equivalents with one or more amino acid insertions, substitutions, or deletions, or additions to one or both ends in an amino acid sequence can be used as the functional equivalents of the invention. Herein, "one or more amino acid insertions, substitutions, or deletions, or additions to one or both ends in an amino acid sequence" mean that an alteration is made with multiple amino acid substitutions or the like that could occur naturally by a well-known technical method such as site-directed mutagenesis or a naturally-occurring mutation.

Altered amino acid sequences of each laminin chain or the like used in the present invention can be those with, for example, about 1 to 30, preferably about 1 to 20, more preferably about 1 to 9, still more preferably about 1 to 5, particularly preferably about 1 to 2 amino acid insertions, substitutions, or deletions, or additions to one or both ends. Altered amino acid sequences may be amino acid sequences having one or more (preferably, 1 or several, or 1, 2, 3, or 4) conservative substitutions in an amino acid sequence of each laminin chain or the like. Herein, "conservative substitution" means a substitution of one or more amino acid residues with other chemically similar amino acid residues which does not substantially alter the functions of a protein. Examples thereof include substitutions of a given hydrophobic residue with another hydrophobic residue, substitutions of a given polar residue with another polar residue having the same electric charge. Functionally similar amino acids that can be used for such a substitution are known in the art for each amino acid. Specific examples of non-polar (hydrophobic) amino acids include alanine, valine, isoleucine, leucine, proline, tryptophan, phenylalanine, methionine, and the like. Specific examples of polar (neutral) amino acids include glycine, serine, threonine, tyrosine, glutamine, asparagine, cysteine, and the like. Specific examples of (basic) amino acids having a positive electric charge include arginine, histidine, lysine and the like. Further, examples of (acidic) amino acids having a negative electric charge include aspartic acid, glutamic acid and the like.

The "agent" as used herein, in a broad sense, may be any substance or other elements (e.g., light, radiation, heat, electricity, and other forms of energy) as long as the intended objective can be achieved. Examples of such a substance include, but are not limited to, proteins, polypeptides, oligopeptides, peptides, polynucleotides, oligonucleotides, nucleotides, nucleic acids (including, for example, DNAs such as cDNA and genomic DNA and RNAs such as mRNA), polysaccharides, oligosaccharides, lipids, organic small molecules (e.g., hormones, ligands, information transmitting substances, organic small molecules, molecules synthesized by combinatorial chemistry, small molecules that can be used as a medicament (e.g., small molecule ligands and the like)) and complex molecules thereof. Typical examples of an agent specific to a polynucleotide include, but are not limited to, polynucleotides having complementarity with a certain sequence homology (e.g., 70% or greater sequence identity) to a sequence of the polynucleotide, polypeptides such as a transcription factor that bind to a promoter region, and the like. Typical examples of an agent specific to a polypeptide include, but are not limited to, antibodies directed specifically to the polypeptide or a derivative or analog thereof (e.g., single chain antibodies), specific ligands or receptors when the polypeptide is a receptor or ligand, substrates when the polypeptide is an enzyme, and the like.

For the ability to adapt to retina transplantation, testing of transplanting cultured cells can be conducted for experimental animals such as mice, rats, rabbits, and monkeys. When the ability to adapt to transplantation into humans is evaluated, adaptability is ideally evaluated in primates such as cynomolgus monkeys after, for example, at least one month, preferably at least two months, more preferably at least three months, still more preferably at least six months, and further still more preferably at least twelve months. Confirmation of the ability to adapt to transplantation in primates, such as monkeys, is important, particularly in human applications.

For the ability to adapt to nerve transplantation, testing of transplanting cultured cells can be conducted on experimental animals such as mice, rats, rabbits, and monkeys. For instance, cultured nerve cells can be transplanted into the retina, peripheral nerve, spinal cord, brain, or the like to observe engraftment thereof.

(General Techniques)

Molecular biological approaches, biochemical approaches, and microbiological approaches used herein are well known and conventional approaches in the art that are described in, for example, Sambrook J. et al. (1989). Molecular Cloning: A Laboratory Manual, Cold Spring Harbor and its 3rd Ed. (2001); Ausubel, F. M. (1987). Current Protocols in Molecular Biology, Greene Pub. Associates and Wiley-Interscience; Ausubel, F. M. (1989). Short Protocols in Molecular Biology: A Compendium of Methods from Current Protocols in Molecular Biology, Greene Pub. Associates and Wiley-Interscience; Innis, M. A. (1990). PCR Protocols: A Guide to Methods and Applications, Academic Press; Ausubel, F. M. (1992). Short Protocols in Molecular Biology: A Compendium of Methods from Current Protocols in Molecular Biology, Greene Pub. Associates; Ausubel, F. M. (1995). Short Protocols in Molecular Biology: A Compendium of Methods from Current Protocols in Molecular Biology, Greene Pub. Associates; Innis, M. A. et al. (1995). PCR Strategies, Academic Press; Ausubel, F. M. (1999). Short Protocols in Molecular Biology: A Compendium of Methods from Current Protocols in Molecular Biology, Wiley, and annual updates; Sninsky, J. J. et al. (1999). PCR Applications: Protocols for Functional Genomics, Academic Press, Gait, M. J. (1985). Oligonucleotide Synthesis: A Practical Approach, IRL Press; Gait, M. J. (1990). Oligonucleotide Synthesis: A Practical Approach, IRL Press; Eckstein, F. (1991). Oligonucleotides and Analogues: A Practical Approach, IRL Press; Adams, R. L. et al. (1992). The Biochemistry of the Nucleic Acids, Chapman & Hall; Shabarova, Z. et al. (1994). Advanced Organic Chemistry of Nucleic Acids, Weinheim; Blackburn, G. M. et al. (1996). Nucleic Acids in Chemistry and Biology, Oxford University Press; Hermanson, G. T. (1996). Bioconjugate Techniques, Academic Press, Bessatsu Jikken Igaku [Experimental Medicine, Supplemental Volume], Idenshi Donyu Oyobi Hatsugen Kaiseki Jikken Ho [Experimental Methods for Transgenesis & Expression Analysis], Yodosha, 1997 and the like. For retinal cells, Japanese National Phase PCT Laid-open Publication No. 2013-502234, the techniques cited therein, and the like can be referred to, but the approaches are not limited thereto. For nerve cells, Shinkei Saibo Baiyoho (Nyuro Saiensu Labo Manuaru) [Nerve cell culturing method (neuroscience lab manual)] book-1997, No/Shinkei Kenkyu Purotokoru-Saibo Baiyo kara Kino Kaiseki he (Baio Manuaru U P Shirizu) [Brain/nerve research protocol-From cell culture to function analysis (Biomanual UP series)] book-1995, the techniques cited therein, and the like can be referred to, but the approaches are not limited thereto. The relevant portions (which can be the entire document) of the above documents are incorporated herein by reference.

Preferred Embodiments

Preferred embodiments are described hereinafter. It is understood that the embodiments are examples of the present invention, and the scope of the present invention should not be limited to such preferred embodiments. It is also understood that those skilled in the art can readily make alterations or modifications within the scope of the present invention by referring to the following preferred embodiments. It is further understood that any embodiments can be combined.

<Therapy or Prophylaxis>

In one aspect, the present invention provides a therapeutic or prophylactic agent for a disease, a disorder, or a condition of a retina such as a retinal pigment epithelium and/or a nerve, comprising at least one agent selected from the group consisting of laminins and fragments thereof. In this aspect, the present invention also provides at least one agent selected from the group consisting of laminins and fragments thereof for therapy or prophylaxis of a disease, a disorder, or a condition of a retina such as a retinal pigment epithelium and/or a nerve cell, wherein the laminins comprise a γ1 chain. In this aspect, the present invention further provides a method for therapy or prophylaxis of a disease, a disorder, or a condition of a retina such as a retinal pigment epithelium and/or a nerve cell, the method comprising administering an effective amount of at least one agent selected from the group consisting of laminins and fragments thereof to a subject in need of the therapy or prophylaxis, wherein the laminins comprise a γ1 chain. A disease, a disorder, or a condition subjected to the therapy or prophylaxis of the invention in this aspect can be any disease, disorder, or condition requiring cell transplantation. Although not wishing to be bound by any theory, the present invention is useful in one form of regenerative medicine, cell transplantation. As another embodiment, this can be applied in transplantation that uses cells formed in the shape of an organ or a sheet. Thus, a completely different effect from the effect on cell growth is achieved, such that application in regenerative medicine or the like is expected.

In a specific embodiment, the present invention provides a therapeutic or prophylactic agent for a disease, a disorder, or a condition of a retinal pigment epithelium and/or a nerve, comprising at least one agent selected from the group consisting of laminins and fragments thereof.

In one embodiment, the agent or laminin used in the present invention comprises an RGD sequence. Although not wishing to be bound by any theory, an RGD sequence is considered to be associated with cell adhesion. It is understood that a laminin with a prominent ability for cell adhesion can be used for therapy or prophylaxis of a disease, a disorder, or a condition of a retina such as a retinal pigment epithelium and/or a nerve, or for improvement thereof.

In another embodiment, the agent or laminin used in the present invention comprises an α4 chain or an α5 chain. Although not wishing to be bound by any theory, this is because types of laminin comprising an α5 chain are demonstrated by the results shown in the Examples and the like to be capable of therapy or prophylaxis of a disease, a disorder, or a condition of a retina such as a retinal pigment epithelium and/or a nerve, or improvement thereof, and β and γ chains are considered to have a certain degree of flexibility as long as an α4 chain or α5 chain is present.

In another embodiment, the agent or laminin used in the present invention comprises a γ1 chain. Although not wishing to be bound by any theory, this is because types of laminin comprising a γ1 chain are demonstrated by the results shown in the Examples and the like as being capable of therapy or prophylaxis of a disease, a disorder, or a condition of a retina such as a retinal pigment epithelium and/or a nerve, or improvement thereof, and α and β chains are considered to have a certain degree of flexibility as long as a γ1 chain is present.

In yet another embodiment the agent or laminin used in the present invention comprises an α4 chain or an α5 chain, and/or a γ1 chain. Although not wishing to be bound by any theory, this is because types of laminin comprising an α4 chain or an α5 chain and/or a γ1 chain are demonstrated by the results shown in the Examples and the like as being capable of therapy or prophylaxis of a disease, a disorder, or a condition of a retina such as a retinal pigment epithelium and/or a nerve, or improvement thereof, and the effects of laminin 411, laminin 511, and laminin 521 are demonstrated such that β is shown to have a certain degree of flexibility as long as an α4 chain or an α5 chain and/or a γ1 chain is determined.

In one preferred embodiment, the laminin comprises laminin 411, laminin 511, and laminin 521. Thus, the agent of the invention may be laminin 411, laminin 511, laminin 521, or a fragment thereof in this embodiment. Any fragment may be used as the fragment of laminin 411, laminin 511, or laminin 521, of the invention, as long as the fragment is capable of therapy or prophylaxis of a disease, a disorder, or a condition of a retina such as a retinal pigment epithelium and/or a nerve, or improvement thereof. Specific examples of such fragments include, but are not limited to, a laminin 511-E8 fragment and a laminin 521 fragment (SEQ ID NOs: 9 and 10 (nucleic acid sequence and amino acid sequence) and SEQ ID NOs: 11 and 12 (nucleic acid sequence and amino acid sequence), respectively) (see Taniguchi Y, Ido H, Sanzen N, Hayashi M, Sato-Nishiuchi R, Futaki S, Sekiguchi K. The C-terminal region of laminin beta chains modulates the integrin binding affinities of laminins. J Biol Chem. 284: 7820-7831, 2009; available from Nippi. Inc.) A laminin 511-E8 fragment and laminin 521 fragment are fragments obtained by elastase treatment and are comprised of three LG domains (LG1 to LG3) in the a chain C-terminal region and a portion of a coiled-coil domain of a heterotrimer. An E8 fragment is regarded as corresponding to an integrin binding site of a heterotrimer molecule in which an α chain, a β chain and a γ chain of a laminin assemble with one another via a coiled-coil domain. Thus, a fragment of a full length laminin in which an integrin binding site is substantially retained can be used as a preferred fragment. It is understood that such a fragment can be made by an appropriate alteration based on information on laminin 511-E8 and laminin 521 fragments. Fragments of laminin 411 can also be made by the same production approach for laminin 511-E8 fragments or the like.

In this regard, an E8 fragment of a human laminin α5β1γ1 (herein, also referred to as "human laminin 511-E8") means a fragment of human laminin α5β1γ1 (hereinafter, also referred to as "human laminin 511") corresponding to the E8 fragment of mouse laminin α1β1β1 (hereinafter, also referred to as "mouse laminin 111-E8"). As used herein, the term "laminin 511-E8 fragment" is also denoted as "Laminin 511-E8 fragment", "Laminin 511 E8", or "Laminin 511-E8". The E8 fragment of a laminin has been identified as a fragment with strong cell adhesion activity among fragments that can be obtained by digesting murine laminin α1β1γ1 (hereinafter, referred to as "mouse laminin 111") with elastase (Edgar D., Timpl R., Thoenen H. The heparin-binding domain of lamininis responsible for its effects on neurite outgrowth and neuronal survival. EMBOJ., 3: 1463-1468, 1984., Goodman S L., Deutzmann R., von der Mark K. Two distinct cell-binding domains in laminin can independently promote nonneuronal cell adhesion and spreading. J. Cell Biol., 105: 589-598, 1987). For human laminin 511 and human laminin 332, the presence of a fragment corresponding to the mouse laminin 111-E8 is assumed upon digestion with elastase. The human laminin 511-E8 fragment used in the present invention only needs to be a fragment of human laminin 511 with the same cell adhesion activity, structure, and approximate molecular weight as mouse laminin 111-E8, and it is not required to be an elastase digestion product of human laminin 511. A method of manufacturing a human laminin 511-E8 fragment is not particularly limited. Examples of such a method include a method of digesting a full length human laminin 511 with a proteolytic enzyme such as elastase in order to fractionate and purify a fragment of interest a method of manufacture as a recombinant protein, and the like. Manufacturing as a recombinant protein is preferred from the viewpoint of manufacturing quantity, quality consistency, manufacturing cost, or the like. A recombinant human laminin 511-E8 fragment can be manufactured by appropriately using a known genetic engineering technique. A method of manufacturing a recombinant human laminin 511-E8 fragment can manufacture, for example, by obtaining DNA encoding a protein of each of α chain, β chain, and γ chain of a human laminin 511-E8 fragment, inserting each obtained DNA into an expression vector, expressing the resulting three kinds of expression vectors by cotransfection into an appropriate host cell, and purifying a protein forming a trimer with a known method (for example, see Hiroyuki Ido, et al, "The requirement of the glutamic acid residue at the third position from the carboxyl termini of the laminin γ chains in integrin binding by laminins" The Journal of Biological Chemistry, 282, 11144-11154, 2007). Japanese Patent Application No. 2011-78370 can be referred to for a specific production method. Similar fragments can also be produced using human laminin 521. This is called a laminin 521-E8 fragment. It is understood that such a fragment can be made in the same manner as a laminin 511-E8 fragment and retains the same activity as a laminin 511-E8 fragment. In the present invention, it is understood that an E8 fragment can be similarly manufactured for any laminin comprising an α4 chain, an α5 chain, and/or a γ1 chain. It is also understood that such an E8 fragment can be used similarly to a full length laminin in the present invention.

In a preferred embodiment, the laminin comprises laminin 411 (α4β1γ1), laminin 511 (α5β1γ1), and laminin 521 (α5β2γ1), or the agent is laminin 411, laminin 511, laminin 521, a laminin 511-E8 fragment, or a laminin 521-E8 fragment.

In another embodiment, the fragment used in the present invention has cell adhesion capability of a retina, such as a retinal pigment epithelial cell and/or a nerve.

In one embodiment, concentration of the agent used (e.g., laminin or a fragment thereof) can be any concentration (also referred to as an effective concentration, or therapeutically effective concentration for therapy, or prophylactically effective concentration for prophylaxis) as long as there is a therapeutic or prophylactic effect. Examples thereof include, but are not limited to, about 0.1 nM or greater, about 0.2 nM or greater, about 0.3 nM or greater, about 0.4 nM or greater, about 0.5 nM or greater, about 0.6 nM or greater, about 0.7 nM or greater, about 0.8 nM or greater, about 0.9 nM or greater, about 1 nM or greater, about 2 nM or greater, about 2.1 nM or greater, about 3 nM or greater, about 4 nM or greater, about 5 nM or greater, about 6 nM or greater, about 7 nM or greater, about 8 nM or greater, about 9 nM or greater, about 10 nM or greater, about 15 nM or greater, about 20 nM or greater, about 21 nM or greater, about 25 nM or greater, about 30 nM or greater, about 40 nM or greater, about 50 nM or greater, about 60 nM or greater, about 70 nM or greater, about 80 nM or greater, about 90 nM or greater, about 100 nM or greater, and the like.

In one embodiment, the site targeted by the present invention includes a retina and/or a nerve. Thus, the diseases, disorders, or conditions targeted by the present invention include, but are not limited to, a disease, a disorder, or a condition of a retinal (pigment) epithelium and/or a nerve targeted by the present invention.

In one embodiment, the site is from a primate. In another embodiment, the ophthalmic site (e.g., retina) and/or a nerve is from a human.

In one embodiment, the cell of the eye (e.g., retinal pigment epithelial cell) and/or a nerve cell is from a primate. In another embodiment, the cell of the eye (e.g., retinal pigment epithelium) and/or a nerve cell is from a human.

In one embodiment, the retinal pigment epithelium or the like and/or the nerve is from a primate. In another embodiment, the retinal pigment epithelium and/or the nerve is from a human.

In one embodiment, the retinal pigment epithelial cell and/or the nerve cell is from a primate. In another embodiment, the retinal pigment epithelial cell and/or the nerve cell is from a human. Although not wishing to be bound by any theory, since the therapeutic or prophylactic effect with a laminin in a retinal epithelium model is demonstrated in rabbits in the Examples of the present specification, it is the understanding of those skilled in the art that a similar therapeutic or prophylactic effect is achieved on a disease, a disorder, or a condition associated with the retina in any mammal.

Examples of diseases, disorders, or conditions of a retinal pigment epithelium targeted by the present invention include diseases which require transplantation of a retinal pigment epithelium. Typical examples thereof include exudative and atrophic age-related macular degeneration, retinitis pigmentosa, retinal pigment epitheliopathy (central serous chorioretinopathy), and other diseases resulting in diminished visual acuity and diminished visual function due to a retinal disorder at especially the macula or the liker. Specific examples thereof include, but are not limited to, retinitis pigmentosa (e.g., (regular) retinitis pigmentosa, achromatic retinitis pigmentosa, (peri)central retinitis pigmentosa, sector retinitis pigmentosa, and unilateral retinitis pigmentosa), retinal pigment epitheliopathy (central serous chorioretinopathy), hereditary retinal degeneration (rod-cone dystrophy), cone (-rod) dystrophy, pigmented paravenous retinochoroidal atrophy, retinitis punctata albescens, Oguchi disease, fundus albipunctatus, congenital stationary night blindness, fundus flavimaculatus, and juvenile retinoschisis), hereditary retinochoroidal degeneration (retinochoroidal dystrophy such as macular fundus, retinitis punctata albescens, Leber congenital blindness, mitochondrial retinopathy, choroidal dystrophy, rod dystrophy, and the like), age-related macular degeneration (including exudative and atrophic forms (also referred to as wet and dry forms) and the like), hereditary macular degeneration/macular dystrophy (e.g. cone dystrophy, cone-rod dystrophy, egg-shaped macular dystrophy (egg yolk-like macular degeneration, and Best disease), Stargardt disease (fundus flavimaculatus), congenital retinoschisis/foveoschisis, pattern dystrophy, occult macular dystrophy, other diseases resulting in diminished visual acuity and diminished visual function due to the above, and the like.

In another embodiment, examples of the disease, disorder, or condition of a nerve targeted by the present invention include diseases, disorders, or conditions of a nerve requiring cell transplantation. Typical examples thereof include, but are not limited to, retinitis pigmentosa, macular degeneration, Stargardt disease, glaucoma, optic neuropathy, spinal cord injury, peripheral neuropathy, Parkinson's disease, Huntington's disease, diseases resulting in a cerebral disorder, other diseases resulting in diminished nervous function due to the above, and the like. These diseases are typical of a disease, a disorder, or a condition of a nerve requiring cell transplantation. A qualitatively and quantitatively significant effect is achieved, which cannot be accomplished with conventional therapy or prophylaxis that does not use cell transplantation.

Examples of subjects of therapy or prophylaxis of a disease, a disorder, or a condition of a retinal pigment epithelium and/or a nerve of the invention include mammals (e.g., humans, mice, rats, hamsters, rabbits, cats, dogs, cows, sheep, monkeys, and the like), and are preferably primates (e.g., humans).

<Combined Therapy>

In another aspect, the present invention provides a therapeutic or prophylactic agent for a disease, a disorder, or a condition of a retina such as a retinal pigment epithelium and/or a nerve, using at least one agent selected from the group consisting of laminins and fragments thereof and a retinal cell such as a retinal pigment epithelial cell and/or a nerve cell. Thus, in this aspect, the present invention provides a method for therapy or prophylaxis of a disease, a disorder, or a condition of a retina such as a retinal pigment epithelium and/or a nerve cell, the method comprising administering an effective amount of at least one agent selected from the group consisting of laminins and fragments thereof to a subject in need of the therapy or prophylaxis, and administering a retina such as a retinal pigment epithelial cell and/or a nerve cell and/or a ROCK inhibitor to the subject, wherein the laminins comprise a γ1 chain. In this regard, the agent and retinal cell, such as a retinal pigment epithelial cell and/or the nerve cell of the invention, may be used as a mixture or administered independently. It is understood that the agent (laminin, fragment thereof, or the like), the cell, the ROCK inhibitor and the like used in the method of the present invention can be used in any form explained herein.

Although not wishing to be bound by any theory, since engraftment to subretinal tissue is demonstrated, it is understood by those skilled in the art that the same effect is achieved for retinal pigment epithelia. Although not wishing to be bound by any theory, since the same tendency (cell behavior and cell adhesion) is observed in the retina as in nerves, it is understood that the same transplantation effect is achieved.

In another aspect, the present invention provides a therapeutic or prophylactic agent for a disease, a disorder, or a condition of a retinal pigment epithelium or the like and/or a nerve, using at least one agent selected from the group consisting of laminins and fragments thereof and a ROCK inhibitor (this term is synonymous with "Rho kinase inhibitor"). In this regard, the agent and the ROCK inhibitor of the invention may be used as a mixture or administered independently. It is understood that the agent (laminin, fragment thereof, or the like) used in the method of the invention can be used in any form explained herein.

In the present invention, "Rho kinase" refers to serine/threonine kinase which is activated with activation of Rho. Examples thereof include ROKα (ROCK-II: Leung, T. et al., J. Biol. Chem., 270, 29051-29054, 1995), p160ROCK (ROKβ, ROCK-I: Ishizaki, T. et al., The EMBO J., 15(8), 1885-1893, 1996), and other proteins having serine/threonine kinase activity.

Examples of ROCK inhibitors include compounds disclosed in the following documents: U.S. Pat. No. 4,678,783, Japanese Patent No. 3421217, International Publication No. WO 95/28387, International Publication No. WO 99/20620, International Publication No. WO 99/61403, International Publication No. WO 02/076976, International Publication No. WO 02/076977, International Publication No. WO 2002/083175, International Publication No. WO 02/100833, International Publication No. WO 03/059913, International Publication No. WO 03/062227, International Publication No. WO 2004/009555, International Publication No. WO 2004/022541, International Publication No. WO 2004/108724, International Publication No. WO 2005/003101, International Publication No. WO 2005/039564, International Publication No. WO 2005/034866, International Publication No. WO 2005/037197, International Publication No. WO 2005/037198, International Publication No. WO 2005/035501, International Publication No. WO 2005/035503, International Publication No. WO 2005/035506, International Publication No. WO 2005/080394, International Publication No. WO 2005/103050, International Publication No. WO 2006/057270, International Publication No. WO 2007/026664, and the like. Such compounds can be manufactured by the methods described in the respective documents where the compounds are disclosed. The specific examples thereof include 1-(5-isoquinolinesulfonyl) homopiperazine or a salt thereof (e.g., fasudil (1-(5-isoquinolinesulfonyl) homopiperazine)), (+)-trans-4-(1-aminoethyl)-1-(4-pyridylcarbamoyl)cyclohexane e((R)-(+)-trans-(4-pyridyl)-4-(1-aminoethyl)-cyclohexanecar boxamide) or a salt thereof (e.g., Y-27632 ((R)-(+)-trans-(4-pyridyl)-4-(1-aminoethyl)-cyclohexanecarboxamide dehydrochloride monohydrate) and the like), and the like. For these compounds, a commercially available product (Wako Pure Chemical Industries, Ltd, Asahi Kasei Pharma Corporation, or the like) can also suitably be used.

In a preferred embodiment, examples of the ROCK inhibitor (Rho kinase inhibitor) used in the present invention include, but are not limited to, Y-27632 ((R)-(+)-trans-(4-pyridyl)-4-(1-aminoethyl)-cyclohexanecarboxamide dehydrochloride monohydrate), and the like.

Any retinal pigment epithelial cell can be used as the "retinal pigment epithelial cell" used herein. The retinal pigment epithelial cell may be isolated or cultured. Retinal pigment epithelial cells may be cultured by any approach. For instance, retinal pigment epithelial cells cultured by the approach described in Hatanaka H, Koizumi N, Okumura N, Kay E P, Mizuhara E, Hamuro J, Kinoshita S: Epithelial-Mesenchymal Transition-Like Phenotypic Changes of Retinal Pigment Epithelium Induced by TGFβ are Prevented by PPARγ Agonists. Invest Ophthalmol Vis Sci, 5; 53(11): 6955-63, 2012., Induction of retinal pigment epithelial cells from monkey iPS cells. Okamoto S, Takahashi M. Invest Ophthalmol Vis Sci. 2011 Nov. 11; 52(12): 8785-90. can be used. Alternatively, retinal pigment epithelial cells may be mechanically separated and cultured with DMEM/F12, 10% FBS, 50 U/mL penicillin, and 50 μg/mL streptomycin.

Any nerve cell can be used as the "nerve cell" used herein. The nerve cell may be isolated or cultured. Nerve cells may be cultured by any approach. For instance, nerve cells cultured by the approach described in Shinkei Saibo Baiyoho (Nyuro Saiensu Labo Manuaru) [Nerve cell culturing method (neuroscience lab manual)] book-1997 and No/Shinkei Kenkyu Purotokoru-Saibo Baiyo kara Kino Kaiseki he (Baio Manuaru U P Shirizu) [Brain/nerve research protocol-From cell culture to function analysis (Biomanual UP series)] book-1995 can be used. Alternatively, nerve cells may be mechanically separated and cultured with DMEM/F12, 10% FBS, 50 U/mL penicillin, and 50 μg/mL streptomycin.

The medium to be used may be a medium component that has been sold and used or a component developed separately for retinal pigment epithelia and/or nerves. Examples of such a medium component include, but are not limited to, OptiMEM, DMEM, M199, MEM, and the like (which are available from INVITROGEN and the like). Typical examples include, for humans, Opti-MEM I Reduced-Serum Medium, Liquid (INVITROGEN catalog No.: 31985-070)+ 8% FBS (BIOWEST, catalog No.: S1820-500)+200 mg/ml $CaCl_2 \cdot 2H_2O$ (SIGMA catalog No.: C7902-500G)+0.08% chondroitin sulfate (SIGMA catalog No.: C9819-5G)+20 μg/ml ascorbic acid (SIGMA catalog No.: A4544-25G)+50 μg/ml gentamicin (INVITROGEN catalog No.: 15710-064)+5 ng/ml EGF (INVITROGEN catalog No.: PHG0311) acclimated for a 3T3 feeder cell as the basal medium and SB431542 (1 μmol/l), and SB203580 (1 μmol/l).

<1> Harvesting and Culturing Retinal Pigment Epithelial cells and nerve cells in a test tube, or retinal pigment epithelial cells and nerve cells induced from stem cells (e.g., pluripotent stem cells such as iPS cells or ES cells)

Retinal pigment epithelial cells and/or nerve cells are harvested from the retina and/or nerve tissue of a recipient or an appropriate donor using a conventional method. Considering the transplantation conditions in the present invention, retinal pigment epithelial cells and/or nerve cells derived from the same species may be prepared. For example, retinal tissue and/or nerve tissue may be separated and then transferred to a culture dish and treated with Dispase or the like. After the separation, the retinal pigment epithelial cells and/or nerve cells are cultured in the culture liquid of the invention. For example, FBS (fetal bovine serum) (e.g., BIOWEST, catalog number: 51820-500), b-FGF (basic fibroblast growth factor) (e.g., INVITROGEN, catalog number: 13256-029), and an antibiotic substance, such as penicillin or streptomycin, may be appropriately added to commercially available DMEM (Dulbecco's Modified Eagle's Medium) (e.g., INVITROGEN, catalog number: 12320 or the like) as a medium or culture liquid. Coating of the agent of the invention for culturing promotes the adhesion of retinal pigment epithelial cells and/or nerve cells to the surface of a culture container, resulting in excellent growth. When culturing by adding a laminin to the culture liquid, it is preferable to use a culture dish with a surface coated with type I collagen, type IV collagen, fibronectin, laminin, extracellular matrix of bovine retinal pigment epithelial cells, or the like. Alternatively, it is possible to use a common culture container which is treated with a commercially available coating agent such as FNC coating mix® (50 ml (AES-0407), ATHENA, catalog number: 0407). The temperature conditions for culturing retinal pigment epithelial cells and/or nerve cells are not particularly limited, as long as the retinal pigment epithelial cells and/or nerve cells can grow. For example, the temperature is about 25° C. to about 45° C., and is preferably about 30° C. to about 40° C. considering the growth efficiency, and more preferably about 37° C. The culturing method is performed in an environment of about 5 to 10% $CO_2$ concentration under humidification in a normal cell culturing incubator.

The approach for retinal pigment epithelial cells and nerve cells induced from stem cells (e.g., pluripotent stem cells such as iPS cells and ES cells) is the following: in one example of retinal pigment epithelial cell differentiation, a colony of human iPS cells or ES cells are detached. The cells are seeded on a plate by light pipetting until a mass of about 5 to 10 cells is formed. Dkk-1 and Lefty-A are added as differentiation inducing agents. Culturing is performed for 4 days each in 20% KSR and 15% KSR differentiation media and floating culture is performed for 10 days (day 20) in 10% KSR differentiation medium to induce retinal pigment epithelial cells. Serum-free Floating culture of Embryoid Body-like aggregates with quick reaggregation is known as an example of nerve cell differentiation. iPS cells, ES cells, or the like can be differentiated into cells of the central nervous system by dispersing the cells with an enzyme, and allowing reaggregated cellular aggregation mass to float in a special culture liquid that is free of components, with an effect inhibiting nerve differentiation such as serum or transcription factor, and culturing the cells for several days. Please refer to the following references: Satoshi Okamoto, et al. Takahashi Induction of Retinal Pigment Epithelial cell, Invest Ophthalmol Vis Sci. 52(12) 8785-90, 2011, Daisuke Doi, et al. "Isolation of Human Induced Pluripotent Stem Cell-derived Dopaminergic Progenitors by Cell Sorting for Successful Transplantation, Stem Cell Reports, 6; 2(3): 337-50, 2014, Wataya T et al. Minimization of exogenous signals in ES cell culture induces rostral hypothalamic differentiation. Proc Natl Acad Sci 2008 19; 105(33): 11796-801.

<2> Subculturing

After the growth of retinal pigment epithelial cells and/or nerve cells subjected to culturing, the cells may be subcultured. Preferably, subculturing is performed upon sub-confluence or confluence. Subculturing may be performed as follows. First, cells are treated with trypsin-EDTA or the like to detach the cells from the surface of a culture container. The cells are then collected. The culture normalizer or medium of the invention is added to the collected cells to obtain a cell suspension. It is preferable to subject the cells to centrifugation when the cells are collected or after collection.

The centrifugation enables preparation of a high density cell suspension. Preferred cell density is about 1 to $2 \times 10^6$ cells/mL. Examples of centrifugation conditions include, but are not limited to, about 500 rpm (30 g) to about 1000 rpm (70 g), for about 1 to about 10 minutes.

The cell suspension is seeded onto a culture container and subjected to culture in the same manner as in the aforementioned primary culture. While the dilution factor upon subculturing varies depending on the state of the cells, it is about 1:2 to 1:4 and is preferably about 1:3. Subculturing may be conducted under culture conditions similar to those of the aforementioned primary culture. The incubation time varies depending on the status of cells to be used or the like. Examples thereof include about 7 to 30 days. The aforementioned subculturing may be performed multiple times as needed.

In another aspect, the present invention provides a therapeutic or prophylactic agent for an ophthalmic (e.g., especially retinal pigment epithelial) and/or nervous disease, disorder, or condition, using at least one agent selected from the group consisting of laminins and fragments thereof, an ocular (e.g., especially retinal pigment epithelial) cell and/or a nerve cell, and a ROCK inhibitor. In this regard, the agent, the ocular (e.g., especially retinal pigment epithelial) cell and/or the nerve cell, and the ROCK inhibitor of the invention may be used as a mixture of two or more thereof, or may be administered separately. It is understood that the agent (laminin, fragment thereof, or the like), the ROCK inhibitor, and the ocular (e.g., especially retinal pigment epithelial) cells and/or nerve cells used in the method of the invention in this aspect can be used in any form explained herein.

<Coating>

In one aspect, the present invention provides a therapeutic or prophylactic agent for a disease, a disorder, or a condition of a retina such as a retinal pigment epithelium and/or a nerve, comprising at least one agent selected from the group consisting of laminins and fragments thereof, wherein the agent is injected into an eye thereby being contacted with tissue in the eye and/or tissue of a nerve. Thus in this aspect, the present invention also provides a method for therapy or prophylaxis of a disease, a disorder, or a condition of a retina such as a retinal pigment epithelium and/or a nerve, the method comprising administering an effective amount of at least one agent selected from the group consisting of laminins and fragments thereof to a subject, wherein the agent is injected into an eye thereby being contacted with tissue in the eye and/or tissue of a nerve. It is understood that the agent (laminin, fragment thereof, or the like) used in the method of the invention in this aspect can be used in any form explained herein. In this regard, it is understood that the agent is injected into an eye thereby being contacted with tissue in the eye or is injected into a site on a nerve thereby being contacted with tissue of the nerve, resulting in the formation of a coating (also referred to as a laminin coating herein) of at least one agent selected from the group consisting of laminins and fragments thereof in the eye or the nerve to promote ophthalmic healing, especially healing of a retina or the like, and/or the nerve.

In one embodiment, the concentration of the agent used upon coating may be any concentration, as long as there is a therapeutic or prophylactic effect (also referred to as an effective concentration; also referred to as effective coating concentration for coating). Examples thereof include, but are not limited to, about 0.1 nM or greater, about 0.2 nM or greater, about 0.3 nM or greater, about 0.4 nM or greater, about 0.5 nM or greater, about 0.6 nM or greater, about 0.7 nM or greater, about 0.8 nM or greater, about 0.9 nM or greater, about 1 nM or greater, about 2 nM or greater, about 2.1 nM or greater, about 3 nM or greater, about 4 nM or greater, about 5 nM or greater, about 6 nM or greater, about 7 nM or greater, about 8 nM or greater, about 9 nM or greater, about 10 nM or greater, about 15 nM or greater, about 20 nM or greater, about 21 nM or greater, about 25 nM or greater, about 30 nM or greater, about 40 nM or greater, about 50 nM or greater, about 60 nM or greater, about 70 nM or greater, about 80 nM or greater, about 90 nM or greater, about 100 nM or greater, and the like.

In one preferred embodiment, retinal cells or the like such as retinal pigment epithelial cells and/or nerve cells may be further administered after, simultaneously with, or before the agent is injected into a site in an eye (e.g. under a retina) and/or in nerve tissue, and contacted with tissue in the eye (cell or tissue constituting the retina) and/or nerve tissue. Thus, retinal cells or the like such as retinal pigment epithelial cells and/or nerve cells may be administered independently from the agent in the present invention. The timing of administering a retinal cell or the like, such as a retinal pigment epithelial cell and/or a nerve cell, is preferably after or simultaneously with the injection of the agent into an eye and contact with tissue in the eye (coating), and more preferably after the agent is injected into an eye and contacted with tissue in the eye. It was revealed that engraftment of a retinal cell, such as a retinal pigment epithelial cell and/or a nerve cell, administered in such a manner onto a cell or tissue constituting a retina and/or a nerve is promoted by the presence of a coating to significantly promote the therapeutic effect.

In another aspect, the present invention is a therapeutic or prophylactic agent for a disease, a disorder, or a condition of a retinal pigment epithelium and/or a nerve, comprising a mixture of at least one agent selected from the group consisting of laminins and fragments thereof and a retinal cell or the like, such as a retinal pigment epithelial cell and/or a nerve cell, wherein at least one agent selected from the group consisting of laminins and fragments thereof, which differs from at least one agent selected from the group consisting of laminins and fragments thereof, is injected into an eye and/or a nerve thereby being contacted with tissue in the eye and/or the nerve, preferably with a portion of tissue subjected to therapy or prophylaxis (e.g., the retinal pigment epithelium or the like and/or the nerve). Thus, in this aspect, the present invention provides a method for therapy or prophylaxis of a disease, a disorder, or a condition of a retina such as a retinal pigment epithelium and/or a nerve cell, the method comprising administering an effective amount of at least one agent selected from the group consisting of laminins and fragments thereof to a subject in need of the therapy or prophylaxis, wherein the agent is injected under a retina thereby being contacted with cells and/or tissue constituting the retina, wherein the laminins comprise a γ1 chain. The aforementioned mixture may be administered before, simultaneously with, or after at least one agent selected from the group consisting of laminins and fragments thereof is injected into an eye and/or a nerve thereby being contacted with tissue in the eye and/or the nerve (coating). The timing of administering a mixture is preferably after or simultaneously with the injection of the agent into an eye and contact with tissue in the eye and/or the nerve, and more preferably after the agent is injected into the eye and/or the nerve, and contacted with tissue in the eye and/or nerve. Although not wishing to be bound by any theory, it is understood that such a coating provides an environment where establishment of a mixture of the aforementioned agent and a retinal cell or the like such as a retinal pigment epithelial cell and/or a nerve cell is promoted such that healing of the retina or the like and/or the nerve is promoted. It is understood that a retinal cell or the like such as a retinal pigment epithelial cell and a nerve cell can be used in any form explained herein or in any known form.

In a preferred embodiment, the therapeutic or prophylactic agent of the invention, in a form of coating, further comprises a ROCK inhibitor (also referred to as a Rho kinase inhibitor). A ROCK inhibitor and the agent may be concomitantly, sequentially, or independently administered. A ROCK inhibitor (Rho kinase inhibitor) may be in any form explained separately herein and is preferably Y-27632 ((R)-(+)-trans-(4-pyridyl)-4-(1-aminoethyl)-cyclohexanecarboxamide dihydrochloride monohydrate) or the like.

In one embodiment in the present invention, an agent mixed with a retinal cell or the like such as the retinal pigment epithelial cell and/or a nerve cell is about 2.1 nM or greater, and the agent to be injected is about 21 nM or greater.

(Use)

In another aspect, the present invention provides use of at least one agent selected from the group consisting of laminins and fragments thereof in manufacture of a medicament for therapy or prophylaxis of a disease, a disorder, or a condition of a retina such as a retinal pigment epithelium and/or a nerve, wherein the laminins comprise a γ1 chain. Alternatively in this aspect, the present invention provides use of at least one agent selected from the group consisting of laminins and fragments thereof for therapy or prophylaxis of a disease, a disorder, or a condition of a retina such as a retinal pigment epithelium and/or a nerve, wherein the laminins comprise a γ1 chain. It is understood that the agent (laminin, fragment thereof, or the like) used in the use of the invention in this aspect can be used in any form explained herein.

Reference literatures such as scientific literatures, patents, and patent applications cited herein are incorporated herein by reference to the same extent that the entirety of each document is specifically described. As used herein, "or" is used when "at least one or more" matters listed in the sentence can be used. When it is explicitly described as "within the range of two values" herein, the two values themselves are also included in the range. The description "about" as used herein indicates, unless specifically noted otherwise, the numerical value rounded up or down to an effective number, or for a specific value, the value thereof ±10%.

As described above, the present invention has been explained while showing preferred embodiments to facilitate understanding. The present invention is explained hereinafter based on the Examples. The aforementioned explanation and the following Examples are not provided to limit the present invention, but for the sole purpose of exemplification. Thus, the scope of the present invention is not limited to the embodiments and Examples specifically described herein and is limited only by the scope of claims.

EXAMPLES

The Examples of the present invention are disclosed hereinafter. Biological samples and the like, when applicable, were handled in accordance with standards specified by the Ministry of Health, Labour and Welfare, Ministry of Education, Culture, Sports, Science and Technology, or the like.

(Experimental Approach: Preparation of Cultured Retinal Pigment Epithelial Cell)
(Approach)*(Culture)

Eye balls extracted from a cynomolgus monkey that was euthanized for another purpose were purchased (Nissei Bilis Co. Ltd. Otsu, Japan). The retinal pigment epithelial cells were mechanically separated and were cultured with DMEM/F12, 10% FBS, 50 U/mL penicillin, and 50 µg/mL streptomycin.

(Experimental Approach: Preparation of Nerve Cell)
(Approach)*(Culture)
*N2a (Available from JCRB Cell Bank (National Institute of Biomedical Innovation))
*SH-SY5Y (available from ECACC, EC94030304-F0)

The medium was removed from a culture dish during culture. PBS (−) preheated to 37° C. was added in order to wash nerve cells. This was repeated twice. After removing the PBS (−), 0.05% Trypsin-EDTA was added. The mixture was incubated for 3 minutes at 37° C. (5% $CO_2$). The cells were then suspended in DMEM (Wako Pure Chemical Industries, 044-29765)+10% FBS+1% P/S and centrifuged for 3 minutes at 1200 rpm to collect the cells. The cells were seeded at a seeding density of 1:10 for both N2a and H-SY5Y.

(Statistical Analysis)

A statistically significant difference (p value) in mean values comparing two samples was determined using Student's t test. A statistically significant difference in comparing multiple sample sets was analyzed using Dunnett's multiple comparison test. The values shown in the graph represent mean±SE.

Example 1: Effect of Laminin Coating on Cell Adhesion of Retinal Pigment Epithelium In this Example, the effect of laminin coating on cell adhesion of a retinal pigment epithelium was studied.
(Materials and Methods)
*The control was not coated.
Laminin 111 (Biolamina, BLA-LN111-02)
Laminin 211 (Biolamina, BLA-LN211-02)
Laminin 411 (Biolamina, BLA-LN411-02)
Laminin 511 (Biolamina, BLA-LN511-02)
Laminin 521 (Biolamina, BLA-LN521-02)
Laminin 322 (ReproCELL, RCHEOT004)
*Laminin 511-E8 fragment (Nippi. Inc., 382-02413)
*FNC coating mix (50 ml (AES-0407) (ATHENA, catalog number: 0407))
*Collagen (type I) (Nitta Gelatin Inc., KP-4020)
Laminins (full length) were used at 20 µg/ml, and the fragments were used at 5 µg/ml. Type I collagen was used at 150 µg/ml.
*Laminin 111, laminin 211, laminin 411, laminin 511, laminin 521, or laminin 332 was diluted with PBS (−) to 20 µg/ml. The diluted laminin was added to a culture plate for coating at 37° C. (5% $CO_2$) for 2 hours. Laminin 511-E8 fragments were diluted with PBS (−) to 5 µg/ml. The diluted laminin was added to a culture plate for coating at ambient temperature for 3 hours. Type I collage was used for coating at ambient temperature for 1 hour. Retinal pigment epithelial cells were seeded at a ratio of 5000 cells/well in a 96-well plate onto a pre-coated culture dish and were incubated for 24 hours at 37° C. (5% $CO_2$). After 24 hours, the medium was removed and the cells were washed twice with PBS (−). After washing, the cells were added at a ratio of 1:1 with respect to a medium. The mixture was shaken for 2 minutes away from light and was left standing for 10 minutes. Measurements were taken thereafter. Measurements used CellTiter-Glo® Luminescent Cell Viability Assay (Promega Corporation, Madison, WI).
(Results)
The results are shown in FIG. 1. As shown, laminin 411, laminin 511, laminin 521, and laminin 511-E8 fragments (and FNC coating mix® (50 ml (AES-0407)) were demonstrated to significantly promote cell adhesion of the retinal pigment epithelium. It is understood that these laminins can be useful in the present invention. Meanwhile, significant promotion of cell adhesion of a retinal pigment epithelium was not observed for laminin 111, laminin 211, and laminin 332.

Example 2: Behavior of Retinal Pigment Epithelium Upon Addition of Laminin

Figure 2:
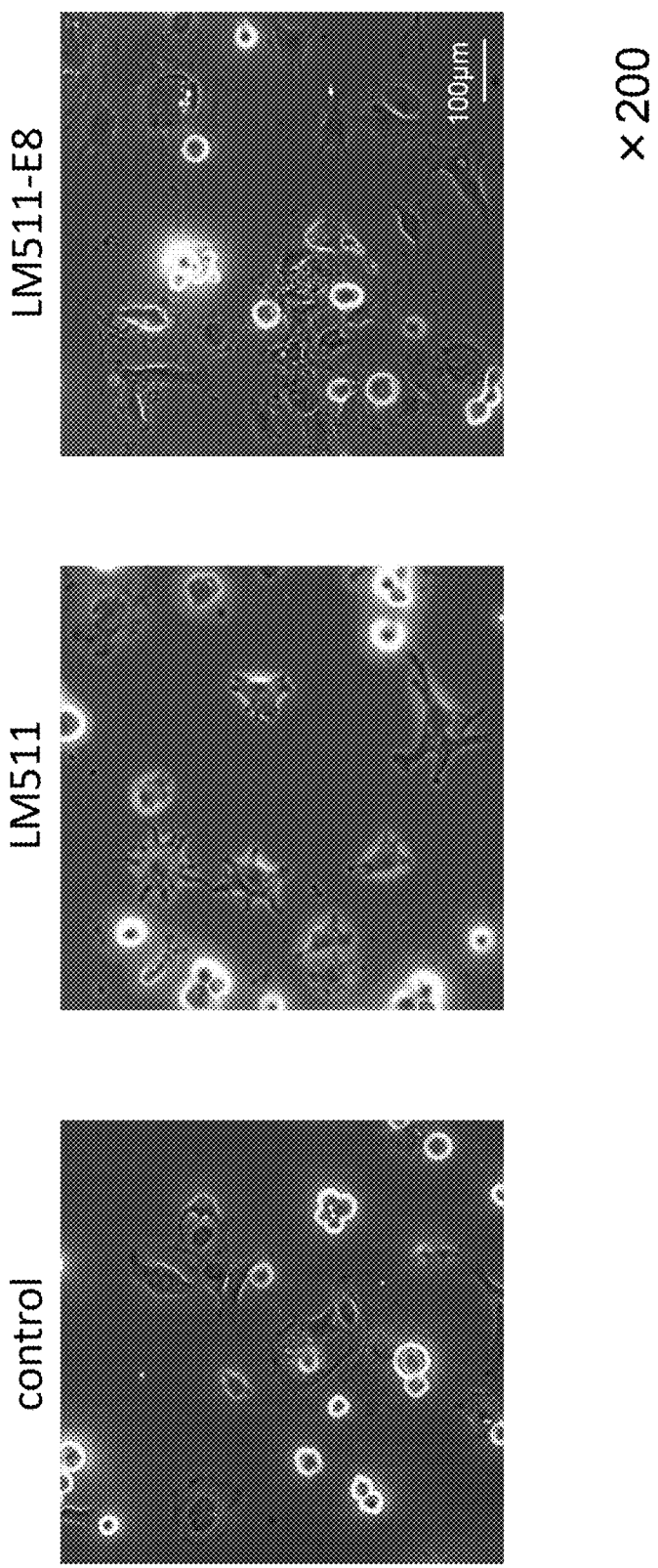
FIG. 2 shows pictures of a retinal pigment epithelium upon addition of a laminin to a medium from a phase contrast microscope.
Figure 3:
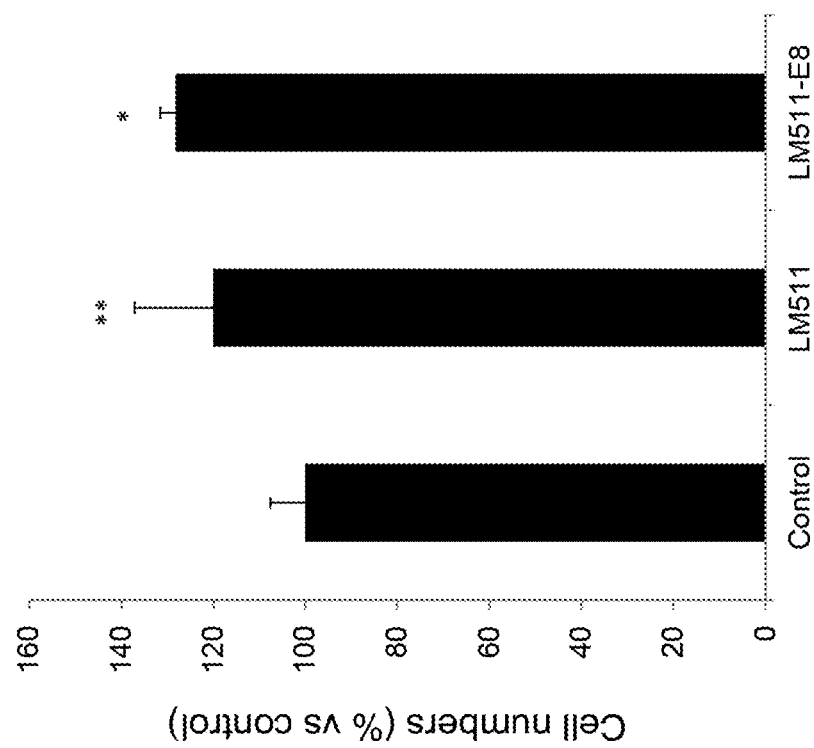
FIG. 3 shows the effect of adding a laminin to a medium on cell adhesion of a retinal pigment epithelium. * indicates $p<0.01$, and ** indicates $p<0.05$. Dunnett's test was used as the test with n=6. For the medium, DMEM/F12 was used as the basal medium, and laminin 511 or E8 was added to 10% fetal bovine serum with 2.1 nM as the final concentration.

In this Example, the behavior of a retinal pigment epithelium upon addition of a laminin was studied.
(Materials and Methods)
*The control was used without additions (although a coating agent was not added, DMEM/F12+10% FBS+1% P/S).
*Laminin 511(Biolamina, BLA-LN511-02)
*Laminin 511-E8 fragment (Nippi. Inc., 382-02413)
(Pictures of Phase Contrast Microscope)
The culture was removed from a culture dish during culture. PBS (−) preheated to 37° C. was added to wash retinal pigment epithelial cells. This was repeated twice. After removing the PBS (−), 0.05% Trypsin was added. The mixture was incubated for 3 minutes at 37° C. (5% $CO_2$). The cells were then suspended in DMEM/F12+10% FBS+1% P/S and were centrifuged for 3 minutes at 1200 rpm to collect the cells. The cells were seeded at a ratio of 5000 cells/96-well plate onto a medium supplemented with laminin 511 or laminin 511-E8 fragments. The mixture was incubated for 24 hours at 37° C. (5% $CO_2$). The status of the cells 24 hours after seeding was captured with a phase contrast microscope.
(Effect on Cell Adhesion)
Retinal pigment epithelial cells were seeded onto a 96-well plate at a ratio of 5000 cells, and were incubated for 24 hours at 37° C. (5% $CO_2$). 24 hours after seeding, the medium was removed and PBS (−) was added in order to wash the cells. This was repeated twice. After washing, the medium and CellTiter-Glog® Luminescent Cell Viability Assay (Promega Corporation, Madison, WI) were added at a ratio of 1:1. The mixture was shaken for 2 minutes away from light and was then left standing for 10 minutes away from light. Measurements were taken thereafter. As for the timing of addition, each of laminin 511 and laminin 511-E8 fragments was added to the cell suspension immediately prior to seeding the cells, so that the concentration was 2.1 nM.
(Results)
Results are shown in FIGS. 2 and 3. FIG. 2 shows pictures of retinal pigment epithelia upon adding a laminin to a medium from a phase contrast microscope. FIG. 3 shows the effect of adding a laminin to a medium on cell adhesion of a retinal pigment epithelium. These drawings show that cell adhesion is promoted by adding a laminin 511-E8 fragment to a medium and seeding a retinal pigment epithelial cell.

Figure 4:
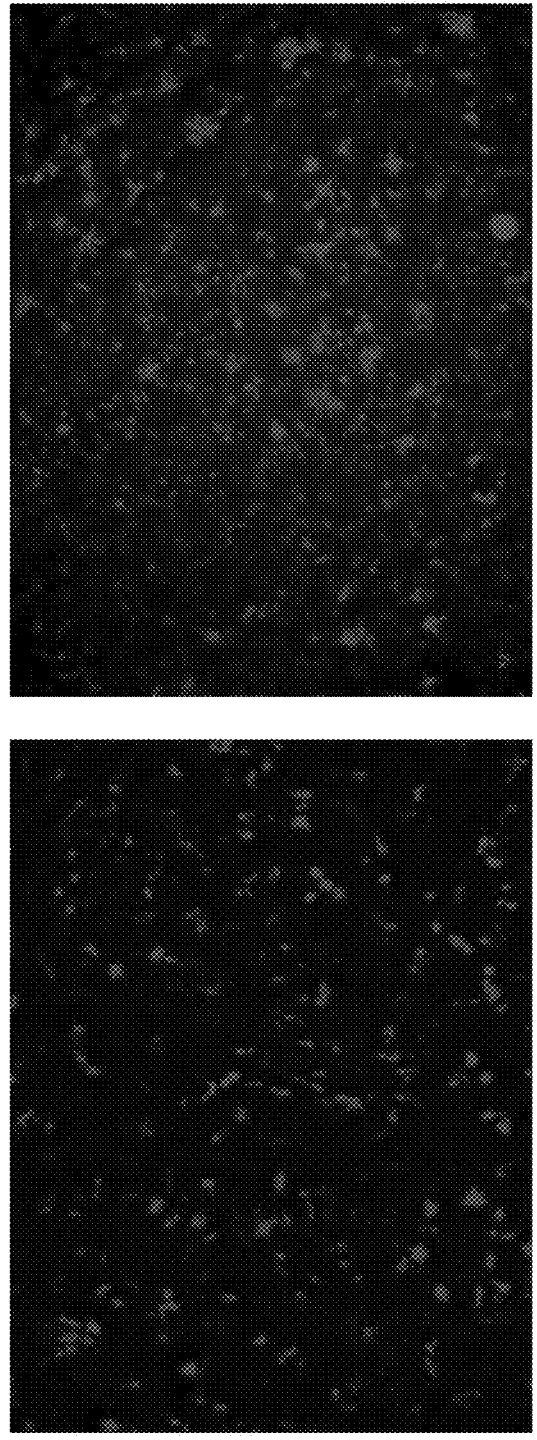
FIG. 4 shows results from tests of transplanting cultured monkey retinal pigment epithelial cells fluorescently labeled with DiI under a rabbit retina with concomitant use of a laminin 511-E8 fragment. The left side shows the result of no laminin 511-E8 fragment, and the right side shows the result of adding a laminin 511-E8 fragment. $2.0\times10^5$ cells were injected using an injection needle under a retina with 100 μl of DMEM/F12 that was adjusted so that the final concentration of laminin 511-E8 fragments was 2.1 nM. After 5 days, DiI positive cells were observed to confirm engraftment of transplanted cells onto subretinal tissue.

Example 3: Example of Application to Retinal Pigment Epithelium Transplantation A test of transplanting cultured retinal pigment epithelial cells, concomitantly with a laminin 511-E8 fragment, under a rabbit retina, was conducted to confirm that transplantation of cells together with a laminin 511-E8 fragment improves engraftment of the transplanted cells onto subretinal tissue.
(Materials, Used Reagents, Methods, etc.)
This Example used the following reagents and the like.
*Cultured monkey retinal pigment epithelial cells
Eye balls extracted from a cynomolgus monkeyeuthanized for another purpose was purchased (Nissei Bilis Co., Ltd. Otsu, Japan). The retinal pigment epithelial cells were mechanically separated and cultured with DMEM/F12, 10% FBS, 50 U/mL penicillin, and 50 ug/mL streptomycin.
*Laminin 511-E8 fragment (Nippi. Inc., 382-02413)
*Rabbit (Japanese white rabbit, Oriental Bioservice)
(Method of Confirming Engraftment)
Cultured monkey retinal pigment epithelial cells were fluorescently labeled with DiI (Vybrant DiI cell-labeling solution, Life Technologies (Carlsbad, CA)). The cultured monkey retinal pigment epithelial cells ($2.0 \times 10^5$ cells) were placed in 100 µl of DMEM adjusted so that laminin 511-E8 fragments had a final concentration of 2.1 nM. The cell preparation was injected subretinally into a rabbit using a subretinal injection needle. After 5 days, DiI positive cells were observed to confirm engraftment of the transplanted cells onto subretinal tissue with a fluorescence microscope.
(Results)
Results are shown in FIG. 4. Engraftment of more cells was observed with subretinal injection of cultured retinal pigment epithelial cells together with laminin 511-E8 fragments relative to injection without laminin 511-E8 fragments. This demonstrates that laminins promote adhesion of retinal pigment epithelial cells onto tissue by injection with cell suspension.

Example 4: Example of Application in Transplantation of Retinal Pigment Epithelium in Retinal Disease Model Next, a retinal disease model is used to perform a cultured retinal endothelium transplantation experiment.
(Retinal Disease Model)
The following model was used as the retinal disease model.
*Macular degeneration model using a genetically modified mouse (or a macular degeneration model with a mechanical injury on a retina due to retinal photocoagulation or the like in a model animal such as a monkey, rabbit, rat, or mouse can be used, or a retinitis pigmentosa model using a genetically modified mouse or the like can be used).
(Transplantation Method)
Cultured retinal pigment epithelial cells were fluorescently labeled with DiI (Vybrant DiI cell-labeling solution, Life Technologies (Carlsbad, CA)). The cultured retinal pigment epithelial cells ($2.0 \times 10^5$ cells) were placed in 100 µl of DMEM adjusted so that the laminin 511-E8 fragments had a final concentration of 2.1 nM. The cell preparation was injected subretinally into a rabbit using a subretinal injection needle.
(Histological Examination)
DiI positive cells were observed to confirm engraftment of transplanted cells onto subretinal tissue. Expression of function associated markers, such as RPE65 or $Na^+/K^+F$-ATPase, were examined.
(Measurement of Function)
Function is evaluated by measuring retinal electric potential or the like.
(Results)
It is understood from this Example that a retina is regenerated and function is restored by transplanting cells with laminins in a retinal disease model.

Example 5: Examination in Nerve: Behavior of Nerve Cell (N2a) Upon Adding Laminin to Medium In this Example, the behavior of nerve cells (N2a) upon addition of a laminin was studied. N2a is a typical nerve cell which is stable in a differentiated state.
(Materials and Methods)
*Nerve cells (N2a): see (Experimental approach: Preparation of cultured retinal pigment epithelial cell)
*The control used was a medium without additions (DMEM/F12 10% FBS+1% P/S).
*Laminin 511-E8 fragment (Nippi. Inc., 382-02413)
*Collagen (type IV) (Nitta Gelatin Inc., KP-6020)
*Fibronectin (Wako Pure Chemical Industries, 063-05591)
(Pictures from Phase Contrast Microscope)
Pictures were taken from a phase contrast microscope under the same conditions as Example 2. Pictures were taken 3 hours after the addition of laminins. The cells were seeded at 5000 cells/96-well plate. The laminin concentration used was 2.1 nM.
(Effect on Cell Adhesion)
This Example, which studied the effect on cell adhesion under the same conditions as Example 2, studied engraftment 3 hours after addition of laminins. The cells were seeded at 5000 cells/96-well plate, and the laminin concentration used was 2.1 nM. Collagen type IV and fibronectin used were coated at 20 µg/ml.
(Results)
Results are shown in FIGS. 5 and 6. FIG. 5 shows pictures of nerve cells (N2a) upon adding a laminin to a medium from a phase contrast microscope. FIG. 6 shows the effect of adding a laminin to a medium on adhesion of nerve cells (N2a.). These results demonstrate that addition of laminin 511-E8 fragments to a medium promotes cell-matrix adhesion of nervous system cells. Laminin 511-E8 fragments were demonstrated to promote cell-matrix adhesion of nervous system cells relative to the control, collagen IV, and fibronectin.

Example 6: Examination in Nerve: Behavior of Nerve Cell (SH-SY5Y) Upon Adding Laminin to Medium In this Example, the behavior of nerve cells (SH-SY5Y) upon adding a laminin was studied. SH-SY5Y is a neuroblastoma cell, which is another typical nerve cell.
(Materials and Methods)
*Nerve cells (H-SY5Y): see (Experimental approach: Preparation of cultured retinal pigment epithelial cell)
*The control used was a medium without additions (DMEM 10% FBS+1% P/S).
*Laminin 511-E8 fragment (Nippi. Inc., 382-02413)
*Collagen (type IV) (Nitta Gelatin Inc., KP-6020)
*Fibronectin (Wako Pure Chemical Industries, 063-05591)
(Pictures from Phase Contrast Microscope)
The Example was carried out under the same conditions as Examples 2 and 5. Pictures were taken 3 hours after the addition of laminins. The cells were seeded at 5000 cells/96-well plate. The laminin concentration used was 2.1 nM. Collagen type IV and fibronectin used were coated at 20 µg/ml.
(Effect on Cell Adhesion)
The Example was carried out under the same conditions as Examples 2 and 5. Engraftment was studied after 3 hours after laminin addition. The cells were seeded at 5000 cells/96-well plate. The laminin concentration used was 2.1 nM. Collagen type IV and fibronectin used were coated at 20 µg/ml.
(Results)
Results are shown in FIGS. 7 and 8. FIG. 7 shows pictures of nerve cells (SH-SYSY) upon adding a laminin to a medium from a phase contrast microscope. FIG. 8 shows the effect of adding a laminin to a medium on adhesion of nerve cells (SH-SY5Y). These results demonstrate that cell adhesion is promoted by adding laminin 511-E8 fragments to a medium and seeding nerve cells. Laminin 511-E8 fragments were demonstrated to promote cell-matrix adhesion of nervous system cells relative to the control, collagen IV, and fibronectin.

Example 7: Formulation Example: Laminin-Cell Mixture Formulation

In this Example, a therapeutic solution containing the agent of the invention is manufactured as follows, as a Formulation Example.
The following solution is prepared by a conventional method.
Laminin 411, laminin 511, laminin 521 and/or a fragment thereof (0.75 µg/cm$^2$)
Final concentration is 2.1 nM Cultured Corneal Endothelial Cells
(appropriate amount of cells prepared according to Example 1 or the like)
Suitable Guffer
appropriate amount
Total Quantity
100 mL Example 8: Formulation Example: Laminin Coating Composition In this Example, a coating solution comprising the agent of the invention is manufactured as follows, as a Formulation Example.

A coating solution is prepared, as shown below, by a conventional method.

Laminin 411, laminin 511, laminin 521 and/or a fragment thereof (0.75 μg/cm$^2$)
Final concentration is 21 nM
Suitable Buffer
appropriate amount
Total Quantity
100 mL Each component can be obtained as described in Examples 1 to 6.

As described above, the present invention has been exemplified using preferred embodiments of the present invention. However, it is understood that the scope of the present invention should be construed only by the scope of the claims. It is understood that patents, patent applications and literatures cited herein are incorporated herein by reference, as if the contents thereof are specifically described herein. The present application claims priority to Japanese Patent Application No. 2014-222948 filed on Oct. 31, 2014, the entire content of which is incorporated herein by reference.

INDUSTRIAL APPLICABILITY

The present invention allows novel ophthalmic therapy, especially novel therapy of corneal endothelial cells (especially human corneal endothelial cells). In particular, the present invention can result in near complete recovery from bullous keratopathy, such that the present invention is particularly useful in the pharmaceutical industry. The present invention is not only useful for corneal endothelial cells, but also for retinal pigment epithelial cells. Since retinal pigment epithelium transplantation has sufficient potential for clinical application, the present invention is particularly useful in manufacturing industries.

[Sequence Listing Free Text]
SEQ ID NO: 1: laminin α5 chain nucleic acid sequence (NM_005560)
SEQ ID NO: 2: laminin α5 chain amino acid sequence (NP_005551)
SEQ ID NO: 3: laminin β1 chain nucleic acid sequence (NM_002291)
SEQ ID NO: 4: laminin β1 chain amino acid sequence (NP_002282)
SEQ ID NO: 5: laminin β2 chain nucleic acid sequence (NM_002292)
SEQ ID NO: 6: laminin β2 chain amino acid sequence (NP_002283)
SEQ ID NO: 7: laminin γ1 chain nucleic acid sequence (NM_002293)
SEQ ID NO: 8: laminin γ1 chain amino acid sequence (NP_002284)
SEQ ID NO: 9: laminin α4 chain nucleic acid sequence (NM_001105206)
SEQ ID NO: 10: laminin α4 chain amino acid sequence (NP_001098676)

The invention claimed is:

1. A method for treating a disease, a disorder, or a condition of a nerve requiring cell transplantation in a subject, comprising administering (a) at least one agent selected from the group consisting of laminin 511 (α5β1γ1) and fragments thereof and (b) a nerve cell or a retinal pigment epithelial cell to the subject, wherein the disease, the disorder, or the condition of the nerve requiring cell transplantation in the subject includes retinitis pigmentosa, macular degeneration, Stargardt disease, glaucoma, or optic neuropathy.

2. The method of claim 1, wherein the nerve cell is administered to the subject.

3. The method of claim 1, wherein the agent is laminin 511-E8 fragment.

* * * * *

SEQUENCE LISTING

```
<160> NUMBER OF SEQ ID NOS: 8

<210> SEQ ID NO 1
<211> LENGTH: 11445
<212> TYPE: DNA
<213> ORGANISM: Homo sapiens

<400> SEQUENCE: 1
agacccgccg ggctcccgcc gcgcgcgctg tccctggagc tcggggacgc ggcccggagc      60
cgggaagatg gcgaagcggc tctgcgcggg gagcgcactg tgtgttcgcg gccccgggg     120 ccccgcgccg ctgctgctgg tcgggctggc gctgctgggc gcggcgcggg cgcgggagga     180
ggcgggcggc ggcttcagcc tgcacccgcc ctacttcaac ctggccgagg gcgcccgcat     240
cgccgcctcc gcgacctgcg gagaggaggc cccggcgcgc ggctccccgc gccccaccga     300 ggaccttttac tgcaagctgg taggggccc cgtggccggc ggcgacccca accagaccat     360
ccggggccag tactgtgaca tctgcacggc tgccaacagc aacaaggcac accccgcgag     420
caatgccatc gatggcacgg agcgctggtg gcagagtcca ccgctgtccc gcggcctgga     480
gtacaacgag gtcaacgtca ccctggacct gggccaggtc ttccacgtgg cctacgtcct     540
catcaagttt gccaactcac cccggccgga cctctgggtg ctggagcggt ccatggactt     600
cggccgcacc taccagccct ggcagttctt tgcctcctcc aagagggact gtctggagcg     660
gttcgggcca cagacgctgg agcgcatcac acgggacgac gcggccatct gcaccaccga     720
```

-continued

```
gtactcacgc atcgtgcccc tggagaacgg agagatcgtg gtgtccctgg tgaacggacg    780
tccgggcgcc atgaatttct cctactcgcc gctgctacgt gagttcacca aggccaccaa    840
cgtccgcctg cgcttcctgc gtaccaacac gctgctgggc catctcatgg ggaaggcgct    900
gcgggacccc acggtcaccc gccggtatta ttacagcatc aaggatatca gcatcggagg    960
ccgctgtgtc tgccacggcc acgcggatgc ctgcgatgcc aaagacccca cggacccgtt   1020
caggctgcag tgcacctgcc agcacaaacc ctgcgggggc acctgcgacc gctgctgccc   1080
cggcttcaat cagcagccgt ggaagcctgc gactgccaac agtgccaacg agtgccagtc   1140
ctgtaactgc tacggccatg ccaccgactg ttactacgac cctgaggtgg accggcgccg   1200
cgccagccag agcctggatg cacctatca gggtgggggt gtctgtatcg actgccagca   1260
ccacaccacc ggcgtcaact gtgagcgctg cctgcccggc ttctaccgct ctcccaacca   1320
ccctctcgac tcgccccacg tctgccgccg ctgcaactgc gagtccgact tcacggatgg   1380
cacctgcgag gacctgacgg tcgatgcta ctgccggccc aacttctctg gggagcggtg   1440
tgacgtgtgt gccgagggct tcacgggctt cccaagctgc tacccgacgc cctcgtcctc   1500
caatgacacc agggagcagg tgctgccagc cggccagatt gtgaattgtg actgcagcgc   1560
ggcagggacc cagggcaacg cctgccggaa ggacccaagg gtgggacgct gtctgtgcaa   1620
acccaacttc caaggcaccc attgtgagct ctgcgcgcca gggttctacg ccccggctg   1680
ccagccctgc cagtgttcca gccctggagt ggccgatgac cgctgtgacc ctgacacagg   1740
ccagtgcagg tgccgagtgg gcttcgaggg ggccacatgt gatcgctgtg ccccggcta   1800
ctttcacttc cctctctgcc agttgtgtgg ctgcagccct gcaggaacct gcccgagggg   1860
ctgcgatgag gccggccgct gcctatgcca gcctgagttt gctggacctc attgtgaccg   1920
gtgccgccct ggctaccatg gtttccccaa ctgccaagca tgcacctgcg accctcgggg   1980
agccctggac cagctctgtg gggcgggagg tttgtgccgc tgccgccccg gctacacagg   2040
cactgcctgc caggaatgca gccccggctt tcacggcttc cccagctgtg tccctgcca   2100
ctgctctgct gaaggctccc tgcacgcagc ctgtgacccc ggagtgggc agtgcagctg   2160
ccggcccgt gtgacggggc tgcggtgtga cacatgtgtg cccggtgcct acaacttccc   2220
ctactgcgaa gctggctctt gccaccctgc cggtctggcc ccagtggatc ctgcccttcc   2280
tgaggcacag gttccctgta tgtgccgggc tcacgtggag gggccgagct gtgaccgctg   2340
caaacctggg ttctggggac tgagccccag caaccccgag ggctgtaccc gctgcagctg   2400
cgacctcagg ggcacactgg gtggagttgc tgagtgccag ccgggcaccg gccagtgctt   2460
ctgcaagccc cacgtgtgcg gccaggcctg gcgtcctgc aaggatggct tctttggact   2520
ggatcaggct gactattttg gctgccgcag ctgccggtgt gacattggcg gtgcactggg   2580
ccagagctgt gaaccgagga cgggcgtctg ccggtgccgc ccaacacccc agggcccac   2640
ctgcagcgag cctgcgaggg accactacct cccggacctg caccacctgc gcctggagct   2700
ggaggaggct gccacacctg agggtcacgc cgtgcgcttt ggcttcaacc cctcgagtt   2760
cgagaacttc agctggaggg gctacgcgca gatggcacct gtccagccca ggatcgtggc   2820
caggctgaac ctgacctccc ctgaccttt ctggctcgtc ttccgatacg tcaaccgggg   2880
ggccatgagt gtgagcgggc gggtctctgt gcgagaggag ggcaggtcgg ccacctgcgc   2940
caactgcaca gcacagagtc agcccgtggc cttcccaccc agcacggagc ctgccttcat   3000
caccgtgccc cagaggggct tcggagagcc ctttgtgctg aacccctggca cctgggccct   3060
gcgtgtggag gccgaagggg tgctcctgga ctacgtggtt ctgctgccta gcgcatacta   3120
```

-continued

```
cgaggcggcg ctcctgcagc tgcgggtgac tgaggcctgc acataccgtc cctctgccca    3180
gcagtctggc gacaactgcc tcctctacac acacctcccc ctggatggct ccccctcggc    3240
cgccgggctg gaggccctgt gtcgccagga caacagcctg ccccggccct gccccacgga    3300
gcagctcagc ccgtcgcacc cgccactgat cacctgcacg ggcagtgatg tggacgtcca    3360
gcttcaagtg gcagtgccac agccaggccg ctatgcccta gtggtggagt acgccaatga    3420
ggatgcccgc caggaggtgg gcgtggccgt gcacacccca cagcgggccc ccagcaggg    3480 gctgctctcc ctgcacccct gcctgtacag caccctgtgc cggggcactg cccgggatac    3540
ccaggaccac ctggctgtct tccacctgga ctcggaggcc agcgtgaggc tcacagccga    3600
acaggcacgc ttcttcctgc acggggtcac tctggtgccc attgaggagt cagcccgga    3660 gttcgtggag ccccgggtca gctgcatcag cagccacggc gcctttggcc caacagtgc    3720 cgcctgtctg ccctcgcgct tcccaaagcc gccccagccc atcatcctca gggactgcca    3780
ggtgatcccg ctgccgcccg gctcccgct gacccacgcg caggatctca ctccagccat    3840
gtccccagct ggaccccgac ctcggccccc caccgctgtg gaccctgatg cagagcccac    3900
cctgctgcgt gagccccagg ccaccgtggt cttcaccacc catgtgccca cgctgggccg    3960
ctatgccttc ctgctgcacg gctaccagcc agcccacccc accttccccg tggaagtcct    4020
catcaacgcc ggccgcgtgt ggcagggcca cgccaacgcc agcttctgtc acatggcta    4080 cggctgccgc accctggtgg tgtgtgaggg ccaggccctg ctggacgtga cccacagcga    4140
gctcactgtg accgtgcgtg tgcccaaggg ccggtggctc tggctggatt atgtactcgt    4200
ggtccctgag aacgtctaca gctttggcta cctccgggag gagcccctgg ataaatccta    4260
tgacttcatc agccactgcg cagcccaggg ctaccacatc agcccagca gctcatccct    4320 gttctgccga aacgctgctg cttccctctc cctcttctat aacaacggag cccgtccatg    4380
tggctgccac gaagtaggtg ctacaggcc cacgtgtgag cccttcgggg ccagtgtcc    4440 ctgccatgcc catgtcattg gccgtgactg ctcccgctgt gccaccggat actggggctt    4500
ccccaactgc aggccctgtg actgcggtgc ccgcctctgt gacgagctca cgggccagtg    4560
catctgcccg ccacgcacca tcccgcccga ctgcctgctg tgccagcccc agacctttgg    4620
ctgccacccc ctggtcggct gtgaggagtg taactgctca gggcccggca tccaggagct    4680
cacagaccct acctgtgaca cagacagcgg ccagtgcaag tgcagaccca acgtgactgg    4740
gcgccgctgt gatacctgct ctccgggctt ccatggctac cccgctgccg cccctgtga    4800 ctgtcacgag gcgggcactg cgcctggcgt gtgtgaccc ctcacagggc agtgctactg    4860
taaggagaac gtgcagggcc ccaaatgtga ccagtgcagc cttgggacct tctcactgga    4920
tgctgccaac cccaaaggtt gcaccgctg cttctgcttt ggggccacgg agcgctgccg    4980
gagctcgtcc tacacccgcc aggagttcgt ggatatggag ggatgggtgc tgctgagcac    5040
tgaccggcag gtggtgcccc acgagcggca gccaggacg gagatgctcc gtgcagacct    5100
gcggcacgtg cctgaggctg tgcccgaggc ttttccccgag ctgtactggc aggccccacc    5160
ctcctacctg ggggaccggg tgtcatccta cggtgggacc ctccgttatg aactgcactc    5220
agagacccag cggggagatg tctttgtccc catggagagc aggccggatg tggtgctgca    5280
gggcaaccag atgagcatca cattcctgga gccggcatac cccacgcctg ccacgttca    5340 ccgtgggcag ctgcagctgg tggaggggaa cttccgggcat acggagacgc gcaacactgt    5400
gtcccgcgag gagctcatga tggtgctggc cagcctggag cagctgcaga tccgtgccct    5460
```

```
cttctcacag atctcctcgg ctgtcttcct gcgcagggtg gcactggagg tggccagccc    5520
agcaggccag ggggccctgg ccagcaatgt ggagctgtgc ctgtgcccg ccagctaccg     5580 gggggactca tgccaggaat gtgccccgg cttctatcgg gacgtcaaag gtctcttcct    5640
gggccgatgt gtcccttgtc agtgccatgg acactcagac cgctgcctcc ctggctctgg    5700
cgtctgtgtg gactgccagc acaaccga aggggcccac tgtgagcgct gccaggctgg     5760
cttcgtgagc agcagggacg accccagcgc ccctgtgtc agctgcccct gcccctctc     5820 agtgccttcc aacaacttcg ccgagggctg tgtcctgcga ggcggccgca cccagtgcct    5880
ctgcaaacct ggttatgcag gtgcctcctg cgagcggtgt gcgcccggat tctttgggaa    5940
cccactggtg ctgggcagct cctgccagcc atgcgactgc agcggcaacg gtgaccccaa    6000
cttgctcttc agcgactgcg accccctgac gggcgcctgc cgtggctgcc tgcgccacac    6060
cactgggccc cgctgcgaga tctgtgcccc cggcttctac ggcaacgccc tgctgcccgg    6120
caactgcacc cggtgcgact gtaccccatg tgggacagag gcctgcgacc cccacagcgg    6180
gcactgcctg tgcaaggcgg gcgtgactgg gcggcgctgt gaccgctgcc aggagggaca    6240
ttttggtttc gatggctgcg ggggctgccg cccgtgtgct tgtggaccgg ccgccgaggg    6300
ctccgagtgc caccccagagc gcggacagtg ccactgccga ccaggaccga tgggaccccca    6360 gtgccgcgag tgtgccctg gctactgggg gctccctgag cagggctgca ggcgctgcca    6420
gtgccctggg ggccgctgtg accctcacac gggccgctgc aactgccccc cggggctcag    6480
cggggagcgc tgcgacacct gcagccagca gcatcaggtg cctgttccag gcgggcctgt    6540
gggccacagc atccactgtg aagtgtgtga ccactgtgtg gtcctgctcc tggatgacct    6600
ggaacgggcc ggcgccctcc tccccgccat tcacgagcaa ctgcgtggca tcaatgccag    6660
ctccatggcc tgggccgtc tgcacaggct gaacgcctcc atcgctgacc tgcagagcca    6720
gctccggagc cccctgggcc cccgccatga cggcacag cagctggagg tgctggagca    6780
gcagagcaca agcctcgggc aggacgcacg cggctaggc ggccaggccg tggggacccg    6840
agaccaggcg agccaattgc tggccggcac cgaggccaca ctgggccatg cgaagacgct    6900
gttggcggcc atccgggctg tggaccgcac cctgagcgag ctcatgtccc agacgggcca    6960
cctggggctg gccaatgcct cggctccatc aggtgagcag ctgctccgga cactggccga    7020 ggtgagcgg ctgctctggg agatgcgggc ccgggacctg ggggccccgc aggcagcagc    7080
tgaggctgag ttggctgcag cacagagatt gctggcccgg gtgcaggagc agctgagcag    7140
cctctgggag gagaaccagg cactggccac acaaacccgc gaccggctgg cccagcacga    7200
ggccggcctc atggacctgc gagaggcttt gaaccgggca gtggacgcca cacgggaggc    7260
ccaggagctc aacagccgca accaggagcg cctggaggaa gccctgcaaa ggaagcagga    7320
gctgtcccgg gacaatgcca ccctgcaggc cactctgcat gcggctaggg acaccctggc    7380
cagcgtcttc agattgctgc acagcctgga ccaggctaag gaggagctgg agcgcctcgc    7440
cgccagcctg gacgggctc ggaccccact gctgcagagg atgcagacct tctccccggc    7500
gggcagcaag ctgcgtctag tggaggccgc cgaggcccac gcacagcagc tgggccagct    7560
ggcactcaat ctgtccagca tcatcctgga cgtcaaccag gaccgcctca cccagagggc    7620
catcgaggcc tccaacgcct acagccgcat cctgcaggcc gtgcaggctg ccgaggatgc    7680
tgctggccag gccctgcagc aggcggacca cgtgggcg acggtggtgc ggcagggcct    7740 ggtgaccga gccagcagc tcctggccaa cagcactgca ctagaagagg ccatgctcca    7800
ggaacagcag aggctgggcc ttgtgtgggc tgccctccag ggtgccagga cccagctccg    7860
```

-continued

```
agatgtccgg gccaagaagg accagctgga ggcgcacatc caggcggcgc aggccatgct   7920
tgccatggac acagacgaga caagcaagaa gatcgcacat gccaaggctg tggctgctga   7980
agcccaggac accgccaccc gtgtgcagtc ccagctgcag gccatgcagg agaatgtgga   8040
gcggtggcag ggccagtacg agggcctgcg gggccaggac ctgggccagg cagtgcttga   8100
cgcaggccac tcagtgtcca ccctggagaa gacgctgccc cagctgctgg ccaagctgag   8160
catcctggag aaccgtgggg tgcacaacgc cagcctggcc ctgtccgcca gcattggccg   8220
cgtgcgagag ctcattgccc aggcccgggg ggctgccagt aaggtcaagg tgcccatgaa   8280
gttcaacggg cgctcagggg tgcagctgcg caccccacgg gatcttgccg accttgctgc   8340
ctacactgcc ctcaagttct acctgcaggg cccagagcct gagcctgggc agggtaccga   8400
ggatcgcttt gtgatgtaca tgggcagccg ccaggccact ggggactaca tgggtgtgtc   8460
tctgcgtgac aagaaggtgc actgggtgta tcagctgggt gaggcgggcc ctgcagtcct   8520
aagcatcgat gaggacattg gggagcagtt cgcagctgtc agcctggaca ggactctcca   8580
gtttggccac atgtccgtca cagtggagag acagatgatc caggaaacca agggtgacac   8640
ggtgcccct ggggcagagg ggctgctcaa cctgcggcca gacgacttcg tcttctacgt   8700
cggggggtac cccagtacct tcacgccccc tcccctgctt cgcttccccg gctaccgggg   8760
ctgcatcgag atggacacgc tgaatgagga ggtggtcagc ctctacaact tcgagaggac   8820
cttccagctg gacacggctg tggacaggcc ttgtgcccgc tccaagtcga ccggggaccc   8880
gtggctcacg gacggctcct acctggacgg caccggcttc gcccgcatca gcttcgacag   8940
tcagatcagc accaccaagc gcttcgagca ggagctgcgg ctcgtgtcct acagcggggt   9000
gctcttcttc ctgaagcagc agagccagtt cctgtgcttg gccgtgcaag aaggcagcct   9060
cgtgctgttg tatgactttg gggctggcct gaaaaaggcc gtcccactgc agcccccacc   9120
gccccctgacc tcggccagca aggcgatcca ggtgttcctg ctggggggca gccgcaagcg   9180
tgtgctggtg cgtgtggagc gggccacggt gtacagcgtg gagcaggaca atgatctgga   9240
gctggccgac gcctactacc tggggggcgt gccgcccgac cagctgcccc cgagcctgcg   9300
acggctcttc cccaccggag gctcagtccg tggctgcgtc aaaggcatca aggccctggg   9360
caagtatgtg gacctcaagc ggctgaacac gacaggcgtg agcgccggct gcaccgccga   9420
cctgctggtg gggcgcgcca tgactttcca tggccacggc ttccttcgcc tggcgctctc   9480
gaacgtggca ccgctcactg gcaacgtcta ctccggcttc ggcttccaca gcgcccagga   9540
cagtgccctg ctctactacc gggcgtcccc ggatgggcta tgccaggtgt ccctgcagca   9600
gggccgtgtg agcctacagc tcctgaggac tgaagtgaaa actcaagcgg gcttcgccga   9660
tggtgccccc cattacgtcg ccttctacag caatgccacg ggagtctggc tgtatgtcga   9720
tgaccagctc cagcagatga agccccaccg gggaccaccc cccgagctcc agccgcagcc   9780
tgaggggccc ccgaggctcc tcctgggagg cctgcctgag tctggcacca tttacaactt   9840
cagtggctgc atcagcaacg tcttcgtgca gcggctcctg ggcccacagc gcgtatttga   9900
tctgcagcag aacctgggca gcgtcaatgt gagcacgggc tgtgcacccg ccctgcaagc   9960
ccagaccccg ggcctggggc ctagaggact gcaggccacc gcccggaagg cctcccgccg  10020
cagccgtcag cccgcccggc atcctgcctg catgctgccc ccacacctca ggaccacccg  10080
agactcctac cagtttgggg gttccctgtc cagtcacctg gagtttgtgg gcatcctggc  10140
ccgacatagg aactggccca gtctctccat gcacgtcctc ccgcgaagct cccgaggcct  10200
```

```
cctcctcttc actgcccgtc tgaggcccgg cagcccctcc ctggcgctct tcctgagcaa    10260
tggccacttc gttgcacaga tggaaggcct cgggactcgg ctccgcgccc agagccgcca    10320
gcgctcccgg cctggccgct ggcacaaggt ctccgtgcgc tgggagaaga accggatcct    10380
gctggtgacg gacggggccc gggcctggag ccaggagggg ccgcaccggc agcaccaggg    10440
ggcagagcac ccccagcccc acaccctctt tgtgggcggc ctcccggcca gcagccacag    10500
ctccaaactt ccggtgaccg tcgggttcag cggctgtgtg aagagactga ggctgcacgg    10560
gaggcccctg ggggccccca cacggatggc aggggtcaca ccctgcatct tgggcccct     10620
ggaggcgggc ctgttcttcc caggcagcgg gggagttatc actttagacc tcccaggagc    10680
tacactgcct gatgtgggcc tggaactgga ggtgcggccc ctggcagtca ccggactgat    10740
cttccacttg ggccaggccc ggacgccccc ctacttgcag ttgcaggtga ccgagaagca    10800
agtcctgctg cgggcggatg acggagcagg ggagttctcc acgtcagtga cccgccctc     10860
agtgctgtgt gatggccagt ggcaccggct agcggtgatg aaaagcggga atgtgctccg    10920
gctggaggtg gacgcgcaga gcaaccacac cgtgggcccc ttgctggcgg ctgcagctgg    10980
tgccccagcc cctctgtacc tcggggggcct gcctgagccc atggccgtgc agccctggcc    11040
ccccgcctac tgcggctgca tgaggaggct ggcggtgaac cggtccccccg tcgccatgac    11100
tcgctctgtg gaggtccacg gggcagtggg ggccagtggc tgcccagccg cctaggacac    11160
agccaacccc ggccctggt caggcccctg cagctgcctc acaccgcccc ttgtgctcgc     11220
ctcataggtg tctatttgga ctctaagctc tacgggtgac agatcttgtt tctgaagatg    11280
gtttaagtta tagcttctta aacgaaagaa taaaatactg caaatgtttt ttatatttgg    11340
cccttccacc catttttaat tgtgagagat ttgtcaccaa tcatcactgg ttcctcctta    11400
aaaattaaaa agtaacttct gtgtaaccga aaaaaaaaa aaaaa                     11445
```

<210> SEQ ID NO 2
<211> LENGTH: 3695
<212> TYPE: PRT
<213> ORGANISM: Homo sapiens

<400> SEQUENCE: 2

Met Ala Lys Arg Leu Cys Ala Gly Ser Ala Leu Cys Val Arg Gly Pro
1               5                   10                  15

Arg Gly Pro Ala Pro Leu Leu Val Gly Leu Ala Leu Leu Gly Ala
            20                  25                  30

Ala Arg Ala Arg Glu Glu Ala Gly Gly Phe Ser Leu His Pro Pro
        35                  40                  45

Tyr Phe Asn Leu Ala Glu Gly Ala Arg Ile Ala Ala Ser Ala Thr Cys
    50                  55                  60

Gly Glu Glu Ala Pro Ala Arg Gly Ser Pro Arg Pro Thr Glu Asp Leu
65                  70                  75                  80

Tyr Cys Lys Leu Val Gly Gly Pro Val Ala Gly Gly Asp Pro Asn Gln
                85                  90                  95

Thr Ile Arg Gly Gln Tyr Cys Asp Ile Cys Thr Ala Ala Asn Ser Asn
            100                 105                 110

Lys Ala His Pro Ala Ser Asn Ala Ile Asp Gly Thr Glu Arg Trp Trp
        115                 120                 125

Gln Ser Pro Pro Leu Ser Arg Gly Leu Glu Tyr Asn Glu Val Asn Val
    130                 135                 140

Thr Leu Asp Leu Gly Gln Val Phe His Val Ala Tyr Val Leu Ile Lys
145                 150                 155                 160

```
Phe Ala Asn Ser Pro Arg Pro Asp Leu Trp Val Leu Glu Arg Ser Met
                165                 170                 175

Asp Phe Gly Arg Thr Tyr Gln Pro Trp Gln Phe Ala Ser Ser Lys
            180                 185                 190

Arg Asp Cys Leu Glu Arg Phe Gly Pro Gln Thr Leu Glu Arg Ile Thr
            195                 200                 205

Arg Asp Asp Ala Ala Ile Cys Thr Thr Glu Tyr Ser Arg Ile Val Pro
        210                 215                 220

Leu Glu Asn Gly Glu Ile Val Val Ser Leu Val Asn Gly Arg Pro Gly
225                 230                 235                 240

Ala Met Asn Phe Ser Tyr Ser Pro Leu Leu Arg Glu Phe Thr Lys Ala
                245                 250                 255

Thr Asn Val Arg Leu Arg Phe Leu Arg Thr Asn Thr Leu Leu Gly His
                260                 265                 270

Leu Met Gly Lys Ala Leu Arg Asp Pro Thr Val Thr Arg Arg Tyr Tyr
            275                 280                 285

Tyr Ser Ile Lys Asp Ile Ser Ile Gly Gly Arg Cys Val Cys His Gly
        290                 295                 300

His Ala Asp Ala Cys Asp Ala Lys Asp Pro Thr Asp Pro Phe Arg Leu
305                 310                 315                 320

Gln Cys Thr Cys Gln His Asn Thr Cys Gly Gly Thr Cys Asp Arg Cys
                325                 330                 335

Cys Pro Gly Phe Asn Gln Gln Pro Trp Lys Pro Ala Thr Ala Asn Ser
            340                 345                 350

Ala Asn Glu Cys Gln Ser Cys Asn Cys Tyr Gly His Ala Thr Asp Cys
            355                 360                 365

Tyr Tyr Asp Pro Glu Val Asp Arg Arg Arg Ala Ser Gln Ser Leu Asp
        370                 375                 380

Gly Thr Tyr Gln Gly Gly Val Cys Ile Asp Cys Gln His His Thr
385                 390                 395                 400

Thr Gly Val Asn Cys Glu Arg Cys Leu Pro Gly Phe Tyr Arg Ser Pro
                405                 410                 415

Asn His Pro Leu Asp Ser Pro His Val Cys Arg Arg Cys Asn Cys Glu
            420                 425                 430

Ser Asp Phe Thr Asp Gly Thr Cys Glu Asp Leu Thr Gly Arg Cys Tyr
            435                 440                 445

Cys Arg Pro Asn Phe Ser Gly Glu Arg Cys Asp Val Cys Ala Glu Gly
        450                 455                 460

Phe Thr Gly Phe Pro Ser Cys Tyr Pro Thr Pro Ser Ser Ser Asn Asp
465                 470                 475                 480

Thr Arg Glu Gln Val Leu Pro Ala Gly Gln Ile Val Asn Cys Asp Cys
                485                 490                 495

Ser Ala Ala Gly Thr Gln Gly Asn Ala Cys Arg Lys Asp Pro Arg Val
            500                 505                 510

Gly Arg Cys Leu Cys Lys Pro Asn Phe Gln Gly Thr His Cys Glu Leu
            515                 520                 525

Cys Ala Pro Gly Phe Tyr Gly Pro Gly Cys Gln Pro Cys Gln Cys Ser
        530                 535                 540

Ser Pro Gly Val Ala Asp Asp Arg Cys Asp Pro Asp Thr Gly Gln Cys
545                 550                 555                 560

Arg Cys Arg Val Gly Phe Glu Gly Ala Thr Cys Asp Arg Cys Ala Pro
                565                 570                 575
```

```
Gly Tyr Phe His Phe Pro Leu Cys Gln Leu Cys Gly Cys Ser Pro Ala
                580                 585                 590

Gly Thr Leu Pro Glu Gly Cys Asp Glu Ala Gly Arg Cys Leu Cys Gln
            595                 600                 605

Pro Glu Phe Ala Gly Pro His Cys Asp Arg Cys Arg Pro Gly Tyr His
        610                 615                 620

Gly Phe Pro Asn Cys Gln Ala Cys Thr Cys Asp Pro Arg Gly Ala Leu
625                 630                 635                 640

Asp Gln Leu Cys Gly Ala Gly Leu Cys Arg Cys Arg Pro Gly Tyr
                645                 650                 655

Thr Gly Thr Ala Cys Gln Glu Cys Ser Pro Gly Phe His Gly Phe Pro
            660                 665                 670

Ser Cys Val Pro Cys His Cys Ser Ala Glu Gly Ser Leu His Ala Ala
        675                 680                 685

Cys Asp Pro Arg Ser Gly Gln Cys Ser Cys Arg Pro Arg Val Thr Gly
690                 695                 700

Leu Arg Cys Asp Thr Cys Val Pro Gly Ala Tyr Asn Phe Pro Tyr Cys
705                 710                 715                 720

Glu Ala Gly Ser Cys His Pro Ala Gly Leu Ala Pro Val Asp Pro Ala
                725                 730                 735

Leu Pro Glu Ala Gln Val Pro Cys Met Cys Arg Ala His Val Glu Gly
            740                 745                 750

Pro Ser Cys Asp Arg Cys Lys Pro Gly Phe Trp Gly Leu Ser Pro Ser
        755                 760                 765

Asn Pro Glu Gly Cys Thr Arg Cys Ser Cys Asp Leu Arg Gly Thr Leu
770                 775                 780

Gly Gly Val Ala Glu Cys Gln Pro Gly Thr Gly Gln Cys Phe Cys Lys
785                 790                 795                 800

Pro His Val Cys Gly Gln Ala Cys Ala Ser Cys Lys Asp Gly Phe Phe
                805                 810                 815

Gly Leu Asp Gln Ala Asp Tyr Phe Gly Cys Arg Ser Cys Arg Cys Asp
            820                 825                 830

Ile Gly Gly Ala Leu Gly Gln Ser Cys Glu Pro Arg Thr Gly Val Cys
        835                 840                 845

Arg Cys Arg Pro Asn Thr Gln Gly Pro Thr Cys Ser Glu Pro Ala Arg
850                 855                 860

Asp His Tyr Leu Pro Asp Leu His His Leu Arg Leu Glu Leu Glu Glu
865                 870                 875                 880

Ala Ala Thr Pro Glu Gly His Ala Val Arg Phe Gly Phe Asn Pro Leu
                885                 890                 895

Glu Phe Glu Asn Phe Ser Trp Arg Gly Tyr Ala Gln Met Ala Pro Val
            900                 905                 910

Gln Pro Arg Ile Val Ala Arg Leu Asn Leu Thr Ser Pro Asp Leu Phe
        915                 920                 925

Trp Leu Val Phe Arg Tyr Val Asn Arg Gly Ala Met Ser Val Ser Gly
930                 935                 940

Arg Val Ser Val Arg Glu Glu Gly Arg Ser Ala Thr Cys Ala Asn Cys
945                 950                 955                 960

Thr Ala Gln Ser Gln Pro Val Ala Phe Pro Ser Thr Glu Pro Ala
                965                 970                 975

Phe Ile Thr Val Pro Gln Arg Gly Phe Gly Glu Pro Phe Val Leu Asn
            980                 985                 990

Pro Gly Thr Trp Ala Leu Arg Val  Glu Ala Glu Gly Val  Leu Leu Asp
```

-continued

```
               995                 1000                1005
Tyr  Val  Val  Leu  Leu  Pro  Ser  Ala  Tyr  Tyr  Glu  Ala  Ala  Leu  Leu
     1010                1015                1020

Gln  Leu  Arg  Val  Thr  Glu  Ala  Cys  Thr  Tyr  Arg  Pro  Ser  Ala  Gln
     1025                1030                1035

Gln  Ser  Gly  Asp  Asn  Cys  Leu  Leu  Tyr  Thr  His  Leu  Pro  Leu  Asp
     1040                1045                1050

Gly  Phe  Pro  Ser  Ala  Ala  Gly  Leu  Glu  Ala  Leu  Cys  Arg  Gln  Asp
     1055                1060                1065

Asn  Ser  Leu  Pro  Arg  Pro  Cys  Pro  Thr  Glu  Gln  Leu  Ser  Pro  Ser
     1070                1075                1080

His  Pro  Pro  Leu  Ile  Thr  Cys  Thr  Gly  Ser  Asp  Val  Asp  Val  Gln
     1085                1090                1095

Leu  Gln  Val  Ala  Val  Pro  Gln  Pro  Gly  Arg  Tyr  Ala  Leu  Val  Val
     1100                1105                1110

Glu  Tyr  Ala  Asn  Glu  Asp  Ala  Arg  Gln  Glu  Val  Gly  Val  Ala  Val
     1115                1120                1125

His  Thr  Pro  Gln  Arg  Ala  Pro  Gln  Gln  Gly  Leu  Leu  Ser  Leu  His
     1130                1135                1140

Pro  Cys  Leu  Tyr  Ser  Thr  Leu  Cys  Arg  Gly  Thr  Ala  Arg  Asp  Thr
     1145                1150                1155

Gln  Asp  His  Leu  Ala  Val  Phe  His  Leu  Asp  Ser  Glu  Ala  Ser  Val
     1160                1165                1170

Arg  Leu  Thr  Ala  Glu  Gln  Ala  Arg  Phe  Phe  Leu  His  Gly  Val  Thr
     1175                1180                1185

Leu  Val  Pro  Ile  Glu  Glu  Phe  Ser  Pro  Glu  Phe  Val  Glu  Pro  Arg
     1190                1195                1200

Val  Ser  Cys  Ile  Ser  Ser  His  Gly  Ala  Phe  Gly  Pro  Asn  Ser  Ala
     1205                1210                1215

Ala  Cys  Leu  Pro  Ser  Arg  Phe  Pro  Lys  Pro  Pro  Gln  Pro  Ile  Ile
     1220                1225                1230

Leu  Arg  Asp  Cys  Gln  Val  Ile  Pro  Leu  Pro  Pro  Gly  Leu  Pro  Leu
     1235                1240                1245

Thr  His  Ala  Gln  Asp  Leu  Thr  Pro  Ala  Met  Ser  Pro  Ala  Gly  Pro
     1250                1255                1260

Arg  Pro  Arg  Pro  Pro  Thr  Ala  Val  Asp  Pro  Asp  Ala  Glu  Pro  Thr
     1265                1270                1275

Leu  Leu  Arg  Glu  Pro  Gln  Ala  Thr  Val  Val  Phe  Thr  Thr  His  Val
     1280                1285                1290

Pro  Thr  Leu  Gly  Arg  Tyr  Ala  Phe  Leu  Leu  His  Gly  Tyr  Gln  Pro
     1295                1300                1305

Ala  His  Pro  Thr  Phe  Pro  Val  Glu  Val  Leu  Ile  Asn  Ala  Gly  Arg
     1310                1315                1320

Val  Trp  Gln  Gly  His  Ala  Asn  Ala  Ser  Phe  Cys  Pro  His  Gly  Tyr
     1325                1330                1335

Gly  Cys  Arg  Thr  Leu  Val  Val  Cys  Glu  Gly  Gln  Ala  Leu  Leu  Asp
     1340                1345                1350

Val  Thr  His  Ser  Glu  Leu  Thr  Val  Thr  Val  Arg  Val  Pro  Lys  Gly
     1355                1360                1365

Arg  Trp  Leu  Trp  Leu  Asp  Tyr  Val  Leu  Val  Val  Pro  Glu  Asn  Val
     1370                1375                1380

Tyr  Ser  Phe  Gly  Tyr  Leu  Arg  Glu  Glu  Pro  Leu  Asp  Lys  Ser  Tyr
     1385                1390                1395
```

```
Asp Phe Ile Ser His Cys Ala Ala Gln Gly Tyr His Ile Ser Pro
    1400            1405                1410

Ser Ser Ser Ser Leu Phe Cys Arg Asn Ala Ala Ala Ser Leu Ser
    1415            1420                1425

Leu Phe Tyr Asn Asn Gly Ala Arg Pro Cys Gly Cys His Glu Val
    1430            1435                1440

Gly Ala Thr Gly Pro Thr Cys Glu Pro Phe Gly Gln Cys Pro
    1445            1450                1455

Cys His Ala His Val Ile Gly Arg Asp Cys Ser Arg Cys Ala Thr
    1460            1465                1470

Gly Tyr Trp Gly Phe Pro Asn Cys Arg Pro Cys Asp Cys Gly Ala
    1475            1480                1485

Arg Leu Cys Asp Glu Leu Thr Gly Gln Cys Ile Cys Pro Pro Arg
    1490            1495                1500

Thr Ile Pro Pro Asp Cys Leu Leu Cys Gln Pro Gln Thr Phe Gly
    1505            1510                1515

Cys His Pro Leu Val Gly Cys Glu Glu Cys Asn Cys Ser Gly Pro
    1520            1525                1530

Gly Ile Gln Glu Leu Thr Asp Pro Thr Cys Asp Thr Asp Ser Gly
    1535            1540                1545

Gln Cys Lys Cys Arg Pro Asn Val Thr Gly Arg Arg Cys Asp Thr
    1550            1555                1560

Cys Ser Pro Gly Phe His Gly Tyr Pro Arg Cys Arg Pro Cys Asp
    1565            1570                1575

Cys His Glu Ala Gly Thr Ala Pro Gly Val Cys Asp Pro Leu Thr
    1580            1585                1590

Gly Gln Cys Tyr Cys Lys Glu Asn Val Gln Gly Pro Lys Cys Asp
    1595            1600                1605

Gln Cys Ser Leu Gly Thr Phe Ser Leu Asp Ala Ala Asn Pro Lys
    1610            1615                1620

Gly Cys Thr Arg Cys Phe Cys Phe Gly Ala Thr Glu Arg Cys Arg
    1625            1630                1635

Ser Ser Ser Tyr Thr Arg Gln Glu Phe Val Asp Met Glu Gly Trp
    1640            1645                1650

Val Leu Leu Ser Thr Asp Arg Gln Val Val Pro His Glu Arg Gln
    1655            1660                1665

Pro Gly Thr Glu Met Leu Arg Ala Asp Leu Arg His Val Pro Glu
    1670            1675                1680

Ala Val Pro Glu Ala Phe Pro Glu Leu Tyr Trp Gln Ala Pro Pro
    1685            1690                1695

Ser Tyr Leu Gly Asp Arg Val Ser Ser Tyr Gly Gly Thr Leu Arg
    1700            1705                1710

Tyr Glu Leu His Ser Glu Thr Gln Arg Gly Asp Val Phe Val Pro
    1715            1720                1725

Met Glu Ser Arg Pro Asp Val Val Leu Gln Gly Asn Gln Met Ser
    1730            1735                1740

Ile Thr Phe Leu Glu Pro Ala Tyr Pro Thr Pro Gly His Val His
    1745            1750                1755

Arg Gly Gln Leu Gln Leu Val Glu Gly Asn Phe Arg His Thr Glu
    1760            1765                1770

Thr Arg Asn Thr Val Ser Arg Glu Glu Leu Met Met Val Leu Ala
    1775            1780                1785
```

```
Ser Leu Glu Gln Leu Gln Ile Arg Ala Leu Phe Ser Gln Ile Ser
    1790                1795                1800

Ser Ala Val Phe Leu Arg Arg Val Ala Leu Glu Val Ala Ser Pro
    1805                1810                1815

Ala Gly Gln Gly Ala Leu Ala Ser Asn Val Glu Leu Cys Leu Cys
    1820                1825                1830

Pro Ala Ser Tyr Arg Gly Asp Ser Cys Gln Glu Cys Ala Pro Gly
    1835                1840                1845

Phe Tyr Arg Asp Val Lys Gly Leu Phe Leu Gly Arg Cys Val Pro
    1850                1855                1860

Cys Gln Cys His Gly His Ser Asp Arg Cys Leu Pro Gly Ser Gly
    1865                1870                1875

Val Cys Val Asp Cys Gln His Asn Thr Glu Gly Ala His Cys Glu
    1880                1885                1890

Arg Cys Gln Ala Gly Phe Val Ser Ser Arg Asp Asp Pro Ser Ala
    1895                1900                1905

Pro Cys Val Ser Cys Pro Cys Pro Leu Ser Val Pro Ser Asn Asn
    1910                1915                1920

Phe Ala Glu Gly Cys Val Leu Arg Gly Gly Arg Thr Gln Cys Leu
    1925                1930                1935

Cys Lys Pro Gly Tyr Ala Gly Ala Ser Cys Glu Arg Cys Ala Pro
    1940                1945                1950

Gly Phe Phe Gly Asn Pro Leu Val Leu Gly Ser Ser Cys Gln Pro
    1955                1960                1965

Cys Asp Cys Ser Gly Asn Gly Asp Pro Asn Leu Leu Phe Ser Asp
    1970                1975                1980

Cys Asp Pro Leu Thr Gly Ala Cys Arg Gly Cys Leu Arg His Thr
    1985                1990                1995

Thr Gly Pro Arg Cys Glu Ile Cys Ala Pro Gly Phe Tyr Gly Asn
    2000                2005                2010

Ala Leu Leu Pro Gly Asn Cys Thr Arg Cys Asp Cys Thr Pro Cys
    2015                2020                2025

Gly Thr Glu Ala Cys Asp Pro His Ser Gly His Cys Leu Cys Lys
    2030                2035                2040

Ala Gly Val Thr Gly Arg Arg Cys Asp Arg Cys Gln Glu Gly His
    2045                2050                2055

Phe Gly Phe Asp Gly Cys Gly Gly Cys Arg Pro Cys Ala Cys Gly
    2060                2065                2070

Pro Ala Ala Glu Gly Ser Glu Cys His Pro Gln Ser Gly Gln Cys
    2075                2080                2085

His Cys Arg Pro Gly Thr Met Gly Pro Gln Cys Arg Glu Cys Ala
    2090                2095                2100

Pro Gly Tyr Trp Gly Leu Pro Glu Gln Gly Cys Arg Arg Cys Gln
    2105                2110                2115

Cys Pro Gly Gly Arg Cys Asp Pro His Thr Gly Arg Cys Asn Cys
    2120                2125                2130

Pro Pro Gly Leu Ser Gly Glu Arg Cys Asp Thr Cys Ser Gln Gln
    2135                2140                2145

His Gln Val Pro Val Pro Gly Gly Pro Val Gly His Ser Ile His
    2150                2155                2160

Cys Glu Val Cys Asp His Cys Val Val Leu Leu Leu Asp Asp Leu
    2165                2170                2175

Glu Arg Ala Gly Ala Leu Leu Pro Ala Ile His Glu Gln Leu Arg
```

```
            2180                2185                2190
Gly Ile Asn Ala Ser Ser Met Ala Trp Ala Arg Leu His Arg Leu
            2195                2200                2205
Asn Ala Ser Ile Ala Asp Leu Gln Ser Gln Leu Arg Ser Pro Leu
            2210                2215                2220
Gly Pro Arg His Glu Thr Ala Gln Gln Leu Glu Val Leu Glu Gln
            2225                2230                2235
Gln Ser Thr Ser Leu Gly Gln Asp Ala Arg Arg Leu Gly Gly Gln
            2240                2245                2250
Ala Val Gly Thr Arg Asp Gln Ala Ser Gln Leu Leu Ala Gly Thr
            2255                2260                2265
Glu Ala Thr Leu Gly His Ala Lys Thr Leu Leu Ala Ala Ile Arg
            2270                2275                2280
Ala Val Asp Arg Thr Leu Ser Glu Leu Met Ser Gln Thr Gly His
            2285                2290                2295
Leu Gly Leu Ala Asn Ala Ser Ala Pro Ser Gly Glu Gln Leu Leu
            2300                2305                2310
Arg Thr Leu Ala Glu Val Glu Arg Leu Leu Trp Glu Met Arg Ala
            2315                2320                2325
Arg Asp Leu Gly Ala Pro Gln Ala Ala Glu Ala Glu Leu Ala
            2330                2335                2340
Ala Ala Gln Arg Leu Leu Ala Arg Val Gln Glu Gln Leu Ser Ser
            2345                2350                2355
Leu Trp Glu Glu Asn Gln Ala Leu Ala Thr Gln Thr Arg Asp Arg
            2360                2365                2370
Leu Ala Gln His Glu Ala Gly Leu Met Asp Leu Arg Glu Ala Leu
            2375                2380                2385
Asn Arg Ala Val Asp Ala Thr Arg Glu Ala Gln Glu Leu Asn Ser
            2390                2395                2400
Arg Asn Gln Glu Arg Leu Glu Glu Ala Leu Gln Arg Lys Gln Glu
            2405                2410                2415
Leu Ser Arg Asp Asn Ala Thr Leu Gln Ala Thr Leu His Ala Ala
            2420                2425                2430
Arg Asp Thr Leu Ala Ser Val Phe Arg Leu Leu His Ser Leu Asp
            2435                2440                2445
Gln Ala Lys Glu Glu Leu Glu Arg Leu Ala Ala Ser Leu Asp Gly
            2450                2455                2460
Ala Arg Thr Pro Leu Leu Gln Arg Met Gln Thr Phe Ser Pro Ala
            2465                2470                2475
Gly Ser Lys Leu Arg Leu Val Glu Ala Ala Glu Ala His Ala Gln
            2480                2485                2490
Gln Leu Gly Gln Leu Ala Leu Asn Leu Ser Ser Ile Ile Leu Asp
            2495                2500                2505
Val Asn Gln Asp Arg Leu Thr Gln Arg Ala Ile Glu Ala Ser Asn
            2510                2515                2520
Ala Tyr Ser Arg Ile Leu Gln Ala Val Gln Ala Ala Glu Asp Ala
            2525                2530                2535
Ala Gly Gln Ala Leu Gln Gln Ala Asp His Thr Trp Ala Thr Val
            2540                2545                2550
Val Arg Gln Gly Leu Val Asp Arg Ala Gln Gln Leu Leu Ala Asn
            2555                2560                2565
Ser Thr Ala Leu Glu Glu Ala Met Leu Gln Glu Gln Gln Arg Leu
            2570                2575                2580
```

-continued

```
Gly Leu Val Trp Ala Ala Leu Gln Gly Ala Arg Thr Gln Leu Arg
2585                2590                2595

Asp Val Arg Ala Lys Lys Asp Gln Leu Glu Ala His Ile Gln Ala
2600                2605                2610

Ala Gln Ala Met Leu Ala Met Asp Thr Asp Glu Thr Ser Lys Lys
2615                2620                2625

Ile Ala His Ala Lys Ala Val Ala Ala Glu Ala Gln Asp Thr Ala
2630                2635                2640

Thr Arg Val Gln Ser Gln Leu Gln Ala Met Gln Glu Asn Val Glu
2645                2650                2655

Arg Trp Gln Gly Gln Tyr Glu Gly Leu Arg Gly Gln Asp Leu Gly
2660                2665                2670

Gln Ala Val Leu Asp Ala Gly His Ser Val Ser Thr Leu Glu Lys
2675                2680                2685

Thr Leu Pro Gln Leu Leu Ala Lys Leu Ser Ile Leu Glu Asn Arg
2690                2695                2700

Gly Val His Asn Ala Ser Leu Ala Leu Ser Ala Ser Ile Gly Arg
2705                2710                2715

Val Arg Glu Leu Ile Ala Gln Ala Arg Gly Ala Ala Ser Lys Val
2720                2725                2730

Lys Val Pro Met Lys Phe Asn Gly Arg Ser Gly Val Gln Leu Arg
2735                2740                2745

Thr Pro Arg Asp Leu Ala Asp Leu Ala Ala Tyr Thr Ala Leu Lys
2750                2755                2760

Phe Tyr Leu Gln Gly Pro Glu Pro Glu Pro Gly Gln Gly Thr Glu
2765                2770                2775

Asp Arg Phe Val Met Tyr Met Gly Ser Arg Gln Ala Thr Gly Asp
2780                2785                2790

Tyr Met Gly Val Ser Leu Arg Asp Lys Lys Val His Trp Val Tyr
2795                2800                2805

Gln Leu Gly Glu Ala Gly Pro Ala Val Leu Ser Ile Asp Glu Asp
2810                2815                2820

Ile Gly Glu Gln Phe Ala Ala Val Ser Leu Asp Arg Thr Leu Gln
2825                2830                2835

Phe Gly His Met Ser Val Thr Val Glu Arg Gln Met Ile Gln Glu
2840                2845                2850

Thr Lys Gly Asp Thr Val Ala Pro Gly Ala Glu Gly Leu Leu Asn
2855                2860                2865

Leu Arg Pro Asp Asp Phe Val Phe Tyr Val Gly Gly Tyr Pro Ser
2870                2875                2880

Thr Phe Thr Pro Pro Pro Leu Leu Arg Phe Pro Gly Tyr Arg Gly
2885                2890                2895

Cys Ile Glu Met Asp Thr Leu Asn Glu Glu Val Val Ser Leu Tyr
2900                2905                2910

Asn Phe Glu Arg Thr Phe Gln Leu Asp Thr Ala Val Asp Arg Pro
2915                2920                2925

Cys Ala Arg Ser Lys Ser Thr Gly Asp Pro Trp Leu Thr Asp Gly
2930                2935                2940

Ser Tyr Leu Asp Gly Thr Gly Phe Ala Arg Ile Ser Phe Asp Ser
2945                2950                2955

Gln Ile Ser Thr Thr Lys Arg Phe Glu Gln Glu Leu Arg Leu Val
2960                2965                2970
```

-continued

```
Ser Tyr Ser Gly Val Leu Phe Phe Leu Lys Gln Gln Ser Gln Phe
    2975            2980                2985
Leu Cys Leu Ala Val Gln Glu Gly Ser Leu Val Leu Leu Tyr Asp
    2990            2995                3000
Phe Gly Ala Gly Leu Lys Lys Ala Val Pro Leu Gln Pro Pro Pro
    3005            3010                3015
Pro Leu Thr Ser Ala Ser Lys Ala Ile Gln Val Phe Leu Leu Gly
    3020            3025                3030
Gly Ser Arg Lys Arg Val Leu Val Arg Val Glu Arg Ala Thr Val
    3035            3040                3045
Tyr Ser Val Glu Gln Asp Asn Asp Leu Glu Leu Ala Asp Ala Tyr
    3050            3055                3060
Tyr Leu Gly Gly Val Pro Pro Asp Gln Leu Pro Pro Ser Leu Arg
    3065            3070                3075
Arg Leu Phe Pro Thr Gly Gly Ser Val Arg Gly Cys Val Lys Gly
    3080            3085                3090
Ile Lys Ala Leu Gly Lys Tyr Val Asp Leu Lys Arg Leu Asn Thr
    3095            3100                3105
Thr Gly Val Ser Ala Gly Cys Thr Ala Asp Leu Leu Val Gly Arg
    3110            3115                3120
Ala Met Thr Phe His Gly His Gly Phe Leu Arg Leu Ala Leu Ser
    3125            3130                3135
Asn Val Ala Pro Leu Thr Gly Asn Val Tyr Ser Gly Phe Gly Phe
    3140            3145                3150
His Ser Ala Gln Asp Ser Ala Leu Leu Tyr Tyr Arg Ala Ser Pro
    3155            3160                3165
Asp Gly Leu Cys Gln Val Ser Leu Gln Gln Gly Arg Val Ser Leu
    3170            3175                3180
Gln Leu Leu Arg Thr Glu Val Lys Thr Gln Ala Gly Phe Ala Asp
    3185            3190                3195
Gly Ala Pro His Tyr Val Ala Phe Tyr Ser Asn Ala Thr Gly Val
    3200            3205                3210
Trp Leu Tyr Val Asp Asp Gln Leu Gln Gln Met Lys Pro His Arg
    3215            3220                3225
Gly Pro Pro Pro Glu Leu Gln Pro Gln Pro Glu Gly Pro Pro Arg
    3230            3235                3240
Leu Leu Leu Gly Gly Leu Pro Glu Ser Gly Thr Ile Tyr Asn Phe
    3245            3250                3255
Ser Gly Cys Ile Ser Asn Val Phe Val Gln Arg Leu Leu Gly Pro
    3260            3265                3270
Gln Arg Val Phe Asp Leu Gln Asn Leu Gly Ser Val Asn Val
    3275            3280                3285
Ser Thr Gly Cys Ala Pro Ala Leu Gln Ala Gln Thr Pro Gly Leu
    3290            3295                3300
Gly Pro Arg Gly Leu Gln Ala Thr Ala Arg Lys Ala Ser Arg Arg
    3305            3310                3315
Ser Arg Gln Pro Ala Arg His Pro Ala Cys Met Leu Pro Pro His
    3320            3325                3330
Leu Arg Thr Thr Arg Asp Ser Tyr Gln Phe Gly Gly Ser Leu Ser
    3335            3340                3345
Ser His Leu Glu Phe Val Gly Ile Leu Ala Arg His Arg Asn Trp
    3350            3355                3360
Pro Ser Leu Ser Met His Val Leu Pro Arg Ser Ser Arg Gly Leu
```

```
Leu Leu Phe Thr Ala Arg Leu Arg Pro Gly Ser Pro Ser Leu Ala
    3380                3385                3390

Leu Phe Leu Ser Asn Gly His Phe Val Ala Gln Met Glu Gly Leu
    3395                3400                3405

Gly Thr Arg Leu Arg Ala Gln Ser Arg Gln Arg Ser Arg Pro Gly
    3410                3415                3420

Arg Trp His Lys Val Ser Val Arg Trp Glu Lys Asn Arg Ile Leu
    3425                3430                3435

Leu Val Thr Asp Gly Ala Arg Ala Trp Ser Gln Glu Gly Pro His
    3440                3445                3450

Arg Gln His Gln Gly Ala Glu His Pro Gln Pro His Thr Leu Phe
    3455                3460                3465

Val Gly Gly Leu Pro Ala Ser Ser His Ser Ser Lys Leu Pro Val
    3470                3475                3480

Thr Val Gly Phe Ser Gly Cys Val Lys Arg Leu Arg Leu His Gly
    3485                3490                3495

Arg Pro Leu Gly Ala Pro Thr Arg Met Ala Gly Val Thr Pro Cys
    3500                3505                3510

Ile Leu Gly Pro Leu Glu Ala Gly Leu Phe Phe Pro Gly Ser Gly
    3515                3520                3525

Gly Val Ile Thr Leu Asp Leu Pro Gly Ala Thr Leu Pro Asp Val
    3530                3535                3540

Gly Leu Glu Leu Glu Val Arg Pro Leu Ala Val Thr Gly Leu Ile
    3545                3550                3555

Phe His Leu Gly Gln Ala Arg Thr Pro Pro Tyr Leu Gln Leu Gln
    3560                3565                3570

Val Thr Glu Lys Gln Val Leu Leu Arg Ala Asp Asp Gly Ala Gly
    3575                3580                3585

Glu Phe Ser Thr Ser Val Thr Arg Pro Ser Val Leu Cys Asp Gly
    3590                3595                3600

Gln Trp His Arg Leu Ala Val Met Lys Ser Gly Asn Val Leu Arg
    3605                3610                3615

Leu Glu Val Asp Ala Gln Ser Asn His Thr Val Gly Pro Leu Leu
    3620                3625                3630

Ala Ala Ala Ala Gly Ala Pro Ala Pro Leu Tyr Leu Gly Gly Leu
    3635                3640                3645

Pro Glu Pro Met Ala Val Gln Pro Trp Pro Ala Tyr Cys Gly
    3650                3655                3660

Cys Met Arg Arg Leu Ala Val Asn Arg Ser Pro Val Ala Met Thr
    3665                3670                3675

Arg Ser Val Glu Val His Gly Ala Val Gly Ala Ser Gly Cys Pro
    3680                3685                3690

Ala Ala
    3695

<210> SEQ ID NO 3
<211> LENGTH: 5866
<212> TYPE: DNA
<213> ORGANISM: Homo sapiens

<400> SEQUENCE: 3
gggacctgga agcgccccag ccccgcagcg atcgcagatt cggctttcaa acaaaagagg      60
cgccccgggg ggtgggaccg ggacctcacc cggtcctcgc agagttgcgg ccgcccgccc     120
```

```
cttcagcccc ggctctccgt atgcgcatga gcagaggcgc ctccctctgt tcctcccaag      180
gctaaacttt ctaattccct tctttgggct cggggggctcc cggagcaggg cgagagctcg    240
cgtcgccgga aaggaagacg ggaagaaagg gcaggcggct cggcgggcgt cttctccact    300
cctctgccgc gtccccgtgg ctgcagggag ccggcatggg gcttctccag ttgctagctt    360
tcagtttctt agccctgtgc agagcccgag tgcgcgctca ggaacccgag ttcagctacg    420
gctgcgcaga aggcagctgc tatcccgcca cgggcgacct tctcatcggc cgagcacaga    480
agctttcggt gacctcgacg tgcgggctgc acaagcccga accctactgt atcgtcagcc    540
acttgcagga ggacaaaaaa tgcttcatat gcaattccca agatccttat catgagaccc    600
tgaatcctga cagccatctc attgaaaatg tggtcactac atttgctcca aaccgcctta    660
agatttggtg gcaatctgaa aatggtgtgg aaaatgtaac tatccaactg gatttggaag    720
cagaattcca ttttactcat ctcataatga ctttcaagac attccgtcca gctgctatgc    780
tgatagaacg atcgtccgac tttgggaaaa cctggggtgt gtatagatac ttcgcctatg    840
actgtgaggc ctcgtttcca ggcatttcaa ctggccccat gaaaaaagtc gatgacataa    900
tttgtgattc tcgatattct gacattgaac cctcaactga aggagaggtg atatttcgtg    960
ctttagatcc tgctttcaaa atagaagatc cttatagccc aaggatacag aatttattaa   1020
aaattaccaa cttgagaatc aagtttgtga aactgcatac tttgggagat aaccttctgg   1080
attccaggat ggaaatcaga gaaagtatt attatgcagt ttatgatatg gtggttcgag    1140
gaaattgctt ctgctatggt catgccagcg aatgtgcccc tgtggatgga ttcaatgaag    1200
aagtggaagg aatggttcac ggacactgca tgtgcaggca taacaccaag ggcttaaaact   1260 gtgaactctg catggatttc taccatgatt taccttggag acctgctgaa ggccgaaaca    1320
gcaacgcctg taaaaaatgt aactgcaatg aacattccat ctcttgtcac tttgacatgg   1380
ctgtttacct ggccacgggg aacgtcagcg gaggcgtgtg tgatgactgt cagcacacaa    1440
ccatggggcg caactgtgag cagtgcaagc cgttttacta ccagcaccca gagagggaca    1500
tccgagatcc taatttctgt gaacgatgta cgtgtgaccc agctggctct caaaatgagg   1560
gaatttgtga cagctatact gattttttcta ctggtctcat tgctggccag tgtcggtgta    1620
aattaaatgt ggaaggagaa cattgtgatg tttgcaaaga aggcttctat gatttaagca    1680
gtgaagatcc atttggttgt aaatcttgtg cttgcaatcc tctgggaaca attcctggag    1740
ggaatccttg tgattccgag acaggtcact gctactgcaa gcgtctggtg acaggacagc    1800
attgtgacca gtgcctgcca gagcactggg gcttaagcaa tgatttggat ggatgtcgac   1860
catgtgactg tgaccttggg ggagccttaa acaacagttg ctttgcggag tcaggccagt    1920
gctcatgccg gcctcacatg attggacgtc agtgcaacga agtggaacct ggttactact    1980
ttgccaccct ggatcactac ctctatgaag cggaggaagc caacttgggg cctggggtta    2040
gcatagtgga gcggcaatat atccaggacc ggattccctc ctggactgga gccggcttcg   2100
tccgagtgcc tgaagggggct tatttggagt ttttcattga caacatacca tattccatgg    2160
agtacgacat cctaattcgc tacgagccac agctacccga ccactgggaa aaagctgtca    2220
tcacagtgca gcgacctgga aggattccaa ccagcagccg atgtggtaat accatccccg   2280
atgatgacaa ccaggtggtg tcattatcac caggctcaag atatgtcgtc cttcctcggc    2340
cggtgtgctt tgagaaggga acaaactaca cggtgaggtt ggagctgcct cagtacacct   2400
cctctgatag cgacgtggag agcccctaca cgctgatcga ttctcttgtt ctcatgccat    2460
```

```
actgtaaatc actggacatc ttcaccgtgg gaggttcagg agatggggtg gtcaccaaca    2520
gtgcctggga aacctttcag agataccgat gtctagagaa cagcagaagc gttgtgaaaa    2580
caccgatgac agatgtttgc agaaacatca tctttagcat ttctgccctg ttacaccaga    2640
caggcctggc ttgtgaatgc gaccctcagg gttcgttaag ttccgtgtgt gatcccaacg    2700
gaggccagtg ccagtgccgg cccaacgtgg ttggaagaac ctgcaacaga tgtgcacctg    2760
gaacttttgg ctttggcccc agtggatgca aaccttgtga gtgccatctg caaggatctg    2820
tcaatgcctt ctgcaatccc gtcactggcc agtgccactg tttccaggga gtgtatgctc    2880
ggcagtgtga tcggtgctta cctgggcact ggggctttcc aagttgccag ccctgccagt    2940
gcaatggcca cgccgatgac tgcgacccag tgactgggga gtgcttgaac tgccaggact    3000
acaccatggg tcataactgt gaaaggtgct tggctggtta ctatggcgac cccatcattg    3060
ggtcaggaga tcactgccgc ccttgccctt gcccagatgg tcccgacagt ggacgccagt    3120
ttgccaggag ctgctaccaa gatcctgtta ctttacagct tgcctgtgtt tgtgatcctg    3180
gatacattgg ttccagatgt gacgactgtg cctcaggata ctttggcaat ccatcagaag    3240 ttgggggggtc gtgtcagcct tgccagtgtc acaacaacat tgacacgaca gacccagaag    3300
cctgtgacaa ggagactggg aggtgtctca agtgcctgta ccacacggaa ggggaacact    3360
gtcagttctg ccggttttga tactatggtg atgccctcca gcaggactgt cgaaagtgtg    3420
tctgtaatta cctgggcacc gtgcaagagc actgtaacgg ctctgactgc cagtgcgaca    3480
aagccactgg tcagtgcttg tgtcttccta atgtgatcgg gcagaactgt gaccgctgtg    3540
cgcccaatac ctggcagctg ccagtggca ctggctgtga cccatgcaac tgcaatgctg    3600
ctcattcctt cgggccatct tgcaatgagt tcacggggca gtgccagtgc atgcctgggt    3660
ttggaggccg cacctgcagc gagtgccagg aactcttctg gggagacccc gacgtggagt    3720
gccgagcctg tgactgtgac cccaggggca ttgagacgcc acagtgtgac cagtccacgg    3780
gccagtgtgt ctgcgttgag ggtgttgagg gtccacgctg tgacaagtgc acgcgagggt    3840
actcgggggt cttccctgac tgcacaccct gccaccagtg cttgctctc tgggatgtga    3900 tcattgccga gctgaccaac aggacacaca gattcctgga gaaagccaag gccttgaaga    3960
tcagtggtgt gatcgggcct taccgtgaga ctgtggactc ggtggagagg aaagtcagcg    4020
agataaaaga catcctggcg cagagccccg cagcagagcc actgaaaaac attgggaatc    4080
tctttgagga agcagagaaa ctgattaaag atgttacaga aatgatggct caagtagaag    4140
tgaaattatc tgacacaact tcccaaagca acagcacagc caaagaactg gattctctac    4200
agacagaagc cgaaagccta gacaacactg tgaaagaact tgctgaacaa ctggaattta    4260
tcaaaaactc agatattcgg ggtgccttgg atagcattac caagtatttc cagatgtctc    4320
ttgaggcaga ggagagggtg aatgcctcca ccacagaacc caacagcact gtggagcagt    4380
cagccctcat gagagacaga gtagaagacg tgatgatgga gcgagaatcc cagttcaagg    4440
aaaaacaaga ggagcaggct cgcctccttg atgaactggc aggcaagcta caaagcctag    4500
acctttcagc cgctgccgaa atgacctgtg gaacaccccc aggggcctcc tgttccgaga    4560
ctgaatgtgg cggccaaac tgcagaactg acgaaggaga gaggaagtgt ggggggcctg    4620
gctgtggtgg tctggttact gttgcacaca acgcctggca gaaagccatg gacttggacc    4680
aagatgtcct gagtgccctg gctgaagtgg aacagctctc caagatggtc tctgaagcaa    4740
aactgagggc agatgaggca aaacaaagtg ctgaagacat tctgttgaag acaaatgcta    4800
ccaaagaaaa aatggacaag agcaatgagg agctgagaaa tctaatcaag caaatcagaa    4860
```

-continued

```
actttttgac ccaggatagt gctgatttgg acagcattga agcagttgct aatgaagtat    4920
tgaaaatgga gatgcctagc accccacagc agttacagaa cttgacagaa gatatacgtg    4980
aacgagttga agcctttct caagtagagg ttattcttca gcatagtgct gctgacattg    5040
ccagagctga gatgttgtta gaagaagcta aaagagcaag caaaagtgca acagatgtta    5100
aagtcactgc agatatggta aaggaagctc tggaagaagc agaaaaggcc caggtcgcag    5160
cagagaaggc aattaaacaa gcagatgaag acattcaagg aacccagaac ctgttaactt    5220
cgattgagtc tgaaacagca gcttctgagg aaaccttgtt caacgcgtcc cagcgcatca    5280
gcgagttaga gaggaatgtg gaagaactta agcggaaagc tgcccaaaac tccggggagg    5340
cagaatatat tgaaaagta gtatatactg tgaagcaaag tgcagaagat gttaagaaga    5400
ctttagatgg tgaacttgat gaaaagtata aaaagtaga aaatttaatt gccaaaaaaa    5460
ctgaagagtc agctgatgcc agaaggaaag ccgaaatgct acaaaatgaa gcaaaaactc    5520
ttttagctca agcaaatagc aagctgcaac tgctcaaaga tttagaaaga aaatatgaag    5580
acaatcaaag atacttagaa gataaagctc aagaattagc aagactggaa ggagaagtcc    5640
gttcactcct aaaggatata agccagaaag ttgctgtgta tagcacatgc ttgtaacaga    5700
ggagaataaa aaatggctga ggtgaacaag gtaaaacaac tacattttaa aaactgactt    5760
aatgctcttc aaaataaaac atcacctatt taatgttttt aatcacattt tgtatggagt    5820
taaataaagt acagtgcttt tgtataaaaa aaaaaaaaa aaaaaa                    5866
```

<210> SEQ ID NO 4
<211> LENGTH: 1786
<212> TYPE: PRT
<213> ORGANISM: Homo sapiens

<400> SEQUENCE: 4

```
Met Gly Leu Leu Gln Leu Leu Ala Phe Ser Phe Leu Ala Leu Cys Arg
1               5                   10                  15

Ala Arg Val Arg Ala Gln Glu Pro Glu Phe Ser Tyr Gly Cys Ala Glu
            20                  25                  30

Gly Ser Cys Tyr Pro Ala Thr Gly Asp Leu Leu Ile Gly Arg Ala Gln
        35                  40                  45

Lys Leu Ser Val Thr Ser Thr Cys Gly Leu His Lys Pro Glu Pro Tyr
    50                  55                  60

Cys Ile Val Ser His Leu Gln Glu Asp Lys Lys Cys Phe Ile Cys Asn
65                  70                  75                  80

Ser Gln Asp Pro Tyr His Glu Thr Leu Asn Pro Asp Ser His Leu Ile
                85                  90                  95

Glu Asn Val Val Thr Thr Phe Ala Pro Asn Arg Leu Lys Ile Trp Trp
            100                 105                 110

Gln Ser Glu Asn Gly Val Glu Asn Val Thr Ile Gln Leu Asp Leu Glu
        115                 120                 125

Ala Glu Phe His Phe Thr His Leu Ile Met Thr Phe Lys Thr Phe Arg
    130                 135                 140

Pro Ala Ala Met Leu Ile Glu Arg Ser Ser Asp Phe Gly Lys Thr Trp
145                 150                 155                 160

Gly Val Tyr Arg Tyr Phe Ala Tyr Asp Cys Glu Ala Ser Phe Pro Gly
                165                 170                 175

Ile Ser Thr Gly Pro Met Lys Lys Val Asp Asp Ile Ile Cys Asp Ser
            180                 185                 190
```

```
Arg Tyr Ser Asp Ile Glu Pro Ser Thr Glu Gly Glu Val Ile Phe Arg
            195                 200                 205
Ala Leu Asp Pro Ala Phe Lys Ile Glu Asp Pro Tyr Ser Pro Arg Ile
        210                 215                 220
Gln Asn Leu Leu Lys Ile Thr Asn Leu Arg Ile Lys Phe Val Lys Leu
225                 230                 235                 240
His Thr Leu Gly Asp Asn Leu Leu Asp Ser Arg Met Glu Ile Arg Glu
                245                 250                 255
Lys Tyr Tyr Tyr Ala Val Tyr Asp Met Val Val Arg Gly Asn Cys Phe
            260                 265                 270
Cys Tyr Gly His Ala Ser Glu Cys Ala Pro Val Asp Gly Phe Asn Glu
        275                 280                 285
Glu Val Glu Gly Met Val His Gly His Cys Met Cys Arg His Asn Thr
    290                 295                 300
Lys Gly Leu Asn Cys Glu Leu Cys Met Asp Phe Tyr His Asp Leu Pro
305                 310                 315                 320
Trp Arg Pro Ala Glu Gly Arg Asn Ser Asn Ala Cys Lys Lys Cys Asn
                325                 330                 335
Cys Asn Glu His Ser Ile Ser Cys His Phe Asp Met Ala Val Tyr Leu
            340                 345                 350
Ala Thr Gly Asn Val Ser Gly Gly Val Cys Asp Asp Cys Gln His Asn
        355                 360                 365
Thr Met Gly Arg Asn Cys Glu Gln Cys Lys Pro Phe Tyr Tyr Gln His
    370                 375                 380
Pro Glu Arg Asp Ile Arg Asp Pro Asn Phe Cys Glu Arg Cys Thr Cys
385                 390                 395                 400
Asp Pro Ala Gly Ser Gln Asn Glu Gly Ile Cys Asp Ser Tyr Thr Asp
                405                 410                 415
Phe Ser Thr Gly Leu Ile Ala Gly Gln Cys Arg Cys Lys Leu Asn Val
            420                 425                 430
Glu Gly Glu His Cys Asp Val Cys Lys Glu Gly Phe Tyr Asp Leu Ser
        435                 440                 445
Ser Glu Asp Pro Phe Gly Cys Lys Ser Cys Ala Cys Asn Pro Leu Gly
    450                 455                 460
Thr Ile Pro Gly Gly Asn Pro Cys Asp Ser Glu Thr Gly His Cys Tyr
465                 470                 475                 480
Cys Lys Arg Leu Val Thr Gly Gln His Cys Asp Gln Cys Leu Pro Glu
                485                 490                 495
His Trp Gly Leu Ser Asn Asp Leu Asp Gly Cys Arg Pro Cys Asp Cys
            500                 505                 510
Asp Leu Gly Gly Ala Leu Asn Asn Ser Cys Phe Ala Glu Ser Gly Gln
        515                 520                 525
Cys Ser Cys Arg Pro His Met Ile Gly Arg Gln Cys Asn Glu Val Glu
    530                 535                 540
Pro Gly Tyr Tyr Phe Ala Thr Leu Asp His Tyr Leu Tyr Glu Ala Glu
545                 550                 555                 560
Glu Ala Asn Leu Gly Pro Gly Val Ser Ile Val Glu Arg Gln Tyr Ile
                565                 570                 575
Gln Asp Arg Ile Pro Ser Trp Thr Gly Ala Gly Phe Val Arg Val Pro
            580                 585                 590
Glu Gly Ala Tyr Leu Glu Phe Phe Ile Asp Asn Ile Pro Tyr Ser Met
        595                 600                 605
Glu Tyr Asp Ile Leu Ile Arg Tyr Glu Pro Gln Leu Pro Asp His Trp
```

-continued

```
            610                 615                 620
Glu Lys Ala Val Ile Thr Val Gln Arg Pro Gly Arg Ile Pro Thr Ser
625                 630                 635                 640

Ser Arg Cys Gly Asn Thr Ile Pro Asp Asp Asn Gln Val Val Ser
                645                 650                 655

Leu Ser Pro Gly Ser Arg Tyr Val Val Leu Pro Arg Pro Val Cys Phe
                660                 665                 670

Glu Lys Gly Thr Asn Tyr Thr Val Arg Leu Glu Leu Pro Gln Tyr Thr
                675                 680                 685

Ser Ser Asp Ser Asp Val Glu Ser Pro Tyr Thr Leu Ile Asp Ser Leu
                690                 695                 700

Val Leu Met Pro Tyr Cys Lys Ser Leu Asp Ile Phe Thr Val Gly Gly
705                 710                 715                 720

Ser Gly Asp Gly Val Val Thr Asn Ser Ala Trp Glu Thr Phe Gln Arg
                725                 730                 735

Tyr Arg Cys Leu Glu Asn Ser Arg Ser Val Val Lys Thr Pro Met Thr
                740                 745                 750

Asp Val Cys Arg Asn Ile Ile Phe Ser Ile Ser Ala Leu Leu His Gln
                755                 760                 765

Thr Gly Leu Ala Cys Glu Cys Asp Pro Gln Gly Ser Leu Ser Ser Val
                770                 775                 780

Cys Asp Pro Asn Gly Gly Gln Cys Gln Cys Arg Pro Asn Val Val Gly
785                 790                 795                 800

Arg Thr Cys Asn Arg Cys Ala Pro Gly Thr Phe Gly Phe Gly Pro Ser
                805                 810                 815

Gly Cys Lys Pro Cys Glu Cys His Leu Gln Gly Ser Val Asn Ala Phe
                820                 825                 830

Cys Asn Pro Val Thr Gly Gln Cys His Cys Phe Gln Gly Val Tyr Ala
                835                 840                 845

Arg Gln Cys Asp Arg Cys Leu Pro Gly His Trp Gly Phe Pro Ser Cys
                850                 855                 860

Gln Pro Cys Gln Cys Asn Gly His Ala Asp Asp Cys Asp Pro Val Thr
865                 870                 875                 880

Gly Glu Cys Leu Asn Cys Gln Asp Tyr Thr Met Gly His Asn Cys Glu
                885                 890                 895

Arg Cys Leu Ala Gly Tyr Tyr Gly Asp Pro Ile Ile Gly Ser Gly Asp
                900                 905                 910

His Cys Arg Pro Cys Pro Cys Pro Asp Gly Pro Asp Ser Gly Arg Gln
                915                 920                 925

Phe Ala Arg Ser Cys Tyr Gln Asp Pro Val Thr Leu Gln Leu Ala Cys
930                 935                 940

Val Cys Asp Pro Gly Tyr Ile Gly Ser Arg Cys Asp Asp Cys Ala Ser
945                 950                 955                 960

Gly Tyr Phe Gly Asn Pro Ser Glu Val Gly Gly Ser Cys Gln Pro Cys
                965                 970                 975

Gln Cys His Asn Asn Ile Asp Thr Thr Asp Pro Glu Ala Cys Asp Lys
                980                 985                 990

Glu Thr Gly Arg Cys Leu Lys Cys  Leu Tyr His Thr Glu  Gly Glu His
                995                1000                1005

Cys Gln  Phe Cys Arg Phe Gly  Tyr Tyr Gly Asp Ala  Leu Gln Gln
    1010                1015                1020

Asp Cys  Arg Lys Cys Val Cys  Asn Tyr Leu Gly Thr  Val Gln Glu
    1025                1030                1035
```

His Cys Asn Gly Ser Asp Cys Gln Cys Asp Lys Ala Thr Gly Gln
1040             1045                 1050

Cys Leu Cys Leu Pro Asn Val Ile Gly Gln Asn Cys Asp Arg Cys
1055             1060                 1065

Ala Pro Asn Thr Trp Gln Leu Ala Ser Gly Thr Gly Cys Asp Pro
1070             1075                 1080

Cys Asn Cys Asn Ala Ala His Ser Phe Gly Pro Ser Cys Asn Glu
1085             1090                 1095

Phe Thr Gly Gln Cys Gln Cys Met Pro Gly Phe Gly Gly Arg Thr
1100             1105                 1110

Cys Ser Glu Cys Gln Glu Leu Phe Trp Gly Asp Pro Asp Val Glu
1115             1120                 1125

Cys Arg Ala Cys Asp Cys Asp Pro Arg Gly Ile Glu Thr Pro Gln
1130             1135                 1140

Cys Asp Gln Ser Thr Gly Gln Cys Val Cys Val Glu Gly Val Glu
1145             1150                 1155

Gly Pro Arg Cys Asp Lys Cys Thr Arg Gly Tyr Ser Gly Val Phe
1160             1165                 1170

Pro Asp Cys Thr Pro Cys His Gln Cys Phe Ala Leu Trp Asp Val
1175             1180                 1185

Ile Ile Ala Glu Leu Thr Asn Arg Thr His Arg Phe Leu Glu Lys
1190             1195                 1200

Ala Lys Ala Leu Lys Ile Ser Gly Val Ile Gly Pro Tyr Arg Glu
1205             1210                 1215

Thr Val Asp Ser Val Glu Arg Lys Val Ser Glu Ile Lys Asp Ile
1220             1225                 1230

Leu Ala Gln Ser Pro Ala Ala Glu Pro Leu Lys Asn Ile Gly Asn
1235             1240                 1245

Leu Phe Glu Glu Ala Glu Lys Leu Ile Lys Asp Val Thr Glu Met
1250             1255                 1260

Met Ala Gln Val Glu Val Lys Leu Ser Asp Thr Thr Ser Gln Ser
1265             1270                 1275

Asn Ser Thr Ala Lys Glu Leu Asp Ser Leu Gln Thr Glu Ala Glu
1280             1285                 1290

Ser Leu Asp Asn Thr Val Lys Glu Leu Ala Glu Gln Leu Glu Phe
1295             1300                 1305

Ile Lys Asn Ser Asp Ile Arg Gly Ala Leu Asp Ser Ile Thr Lys
1310             1315                 1320

Tyr Phe Gln Met Ser Leu Glu Ala Glu Glu Arg Val Asn Ala Ser
1325             1330                 1335

Thr Thr Glu Pro Asn Ser Thr Val Glu Gln Ser Ala Leu Met Arg
1340             1345                 1350

Asp Arg Val Glu Asp Val Met Met Glu Arg Glu Ser Gln Phe Lys
1355             1360                 1365

Glu Lys Gln Glu Glu Gln Ala Arg Leu Leu Asp Glu Leu Ala Gly
1370             1375                 1380

Lys Leu Gln Ser Leu Asp Leu Ser Ala Ala Ala Glu Met Thr Cys
1385             1390                 1395

Gly Thr Pro Pro Gly Ala Ser Cys Ser Glu Thr Glu Cys Gly Gly
1400             1405                 1410

Pro Asn Cys Arg Thr Asp Glu Gly Glu Arg Lys Cys Gly Gly Pro
1415             1420                 1425

| | | | | | | | | | | |
|---|---|---|---|---|---|---|---|---|---|---|
| Gly | Cys | Gly | Gly | Leu | Val | Thr | Val | Ala | His | Asn | Ala | Trp | Gln | Lys |
| | 1430 | | | | 1435 | | | | 1440 | |

Ala Met Asp Leu Asp Gln Asp Val Leu Ser Ala Leu Ala Glu Val
    1445                1450                1455

Glu Gln Leu Ser Lys Met Val Ser Glu Ala Lys Leu Arg Ala Asp
    1460                1465                1470

Glu Ala Lys Gln Ser Ala Glu Asp Ile Leu Leu Lys Thr Asn Ala
    1475                1480                1485

Thr Lys Glu Lys Met Asp Lys Ser Asn Glu Glu Leu Arg Asn Leu
    1490                1495                1500

Ile Lys Gln Ile Arg Asn Phe Leu Thr Gln Asp Ser Ala Asp Leu
    1505                1510                1515

Asp Ser Ile Glu Ala Val Ala Asn Glu Val Leu Lys Met Glu Met
    1520                1525                1530

Pro Ser Thr Pro Gln Gln Leu Gln Asn Leu Thr Glu Asp Ile Arg
    1535                1540                1545

Glu Arg Val Glu Ser Leu Ser Gln Val Glu Val Ile Leu Gln His
    1550                1555                1560

Ser Ala Ala Asp Ile Ala Arg Ala Glu Met Leu Leu Glu Glu Ala
    1565                1570                1575

Lys Arg Ala Ser Lys Ser Ala Thr Asp Val Lys Val Thr Ala Asp
    1580                1585                1590

Met Val Lys Glu Ala Leu Glu Glu Ala Glu Lys Ala Gln Val Ala
    1595                1600                1605

Ala Glu Lys Ala Ile Lys Gln Ala Asp Glu Asp Ile Gln Gly Thr
    1610                1615                1620

Gln Asn Leu Leu Thr Ser Ile Glu Ser Glu Thr Ala Ala Ser Glu
    1625                1630                1635

Glu Thr Leu Phe Asn Ala Ser Gln Arg Ile Ser Glu Leu Glu Arg
    1640                1645                1650

Asn Val Glu Glu Leu Lys Arg Lys Ala Ala Gln Asn Ser Gly Glu
    1655                1660                1665

Ala Glu Tyr Ile Glu Lys Val Val Tyr Thr Val Lys Gln Ser Ala
    1670                1675                1680

Glu Asp Val Lys Lys Thr Leu Asp Gly Glu Leu Asp Glu Lys Tyr
    1685                1690                1695

Lys Lys Val Glu Asn Leu Ile Ala Lys Lys Thr Glu Glu Ser Ala
    1700                1705                1710

Asp Ala Arg Arg Lys Ala Glu Met Leu Gln Asn Glu Ala Lys Thr
    1715                1720                1725

Leu Leu Ala Gln Ala Asn Ser Lys Leu Gln Leu Leu Lys Asp Leu
    1730                1735                1740

Glu Arg Lys Tyr Glu Asp Asn Gln Arg Tyr Leu Glu Asp Lys Ala
    1745                1750                1755

Gln Glu Leu Ala Arg Leu Glu Gly Glu Val Arg Ser Leu Leu Lys
    1760                1765                1770

Asp Ile Ser Gln Lys Val Ala Val Tyr Ser Thr Cys Leu
    1775                1780                1785

<210> SEQ ID NO 5
<211> LENGTH: 5817
<212> TYPE: DNA
<213> ORGANISM: Homo sapiens

<400> SEQUENCE: 5

```
gaaggcagtt tccggaggga aggggtaggg ttggggtggg ggcgctctcc gcccggtgtt      60
gcgctccttc ccagaatccg ctccggcctt tccttcctgc cgcgattccc aactttgctc     120
aaagtcgctg gactctaagc tgtcggaggg accgctggac agacctggga actgacagag     180
ggcctggagg gaaacaggcc aaagaccac aggcagagtt gacacggaac cccaaagcaa      240
ggaggagggc tcgggcccga gaccgttcac ctcccttat ccctgttccc ctcttcagga      300
tggagctgac ctcaagggaa agagggaggg gacagcctct gccctgggaa cttcgactgg     360
gcctactgct aagcgtgctg gctgccacac tggcacaggc ccctgccccg gatgtgcctg     420
gctgttccag gggaagctgc taccccgcca cgggcgacct gctggtgggc cgagctgaca     480
gactgactgc ctcatccact tgtggcctga atggccccca gccctactgc atcgtcagtc     540
acctgcagga cgaaaagaag tgcttccttt gtgactcccg cgcccccttc tctgctagag     600
acaacccaca cagccatcgc atccagaatg tagtcaccag ctttgcacca cagcggcggg     660
cagcctggtg gcagtcagag aatggtatcc ctgcggtcac catccagctg acctggagg      720 ctgagtttca tttcacacac ctcattatga ccttcaagac atttcgccct gctgccatgc     780
tggtggaacg ctcagcagac tttggccgca cctggcatgt gtaccgatat ttctcctatg     840
actgtggggc tgacttccca ggagtcccac tagcacccc acggcactgg gatgatgtag      900
tctgtgagtc ccgctactca gagattgagc catccactga aggcgaggtc atctatcgtg     960
tgctggaccc tgccatccct atcccagacc cctacagctc acggattcag aacctgttga    1020
agatcaccaa cctacgggtg aacctgactc gtctacacac gttgggagac aacctactcg    1080
acccacggag ggagatccga gagaagtact actatgccct ctatgagctg gttgtacgtg    1140
gcaactgctt ctgctacgga cacgcctcag agtgtgcacc cgccccaggg gcaccagccc    1200
atgctgaggg catggtgcac ggagcttgca tctgcaaaca caacacacgt ggcctcaact    1260
gcgagcagtg tcaggatttc tatcgtgacc tgccctggcg tccggctgag acggccata     1320 gtcatgcctg taggaagtgt gagtgccatg ggcacaccca cagctgccac ttcgacatgg    1380
ccgtatacct ggcatctggc aatgtgagtg gaggtgtgtg tgatggatgt cagcataaca    1440
cagctgggcg ccactgtgag ctctgtcggc ccttcttcta ccgtgaccca accaaggacc    1500
tgcgggatcc ggctgtgtgc cgctcctgtg attgtgaccc catgggttct caagacggtg    1560
gtcgctgtga ttcccatgat gaccctgcac tgggactggt ctccgccag tgtcgctgca    1620 aagaacatgt ggtgggcact cgctgccagc aatgccgtga tggcttcttt gggctcagca    1680
tcagtgaccc tctgggctgc cggcgatgtc aatgtaatgc acggggcaca gtgcctggga    1740
gcactccttg tgaccccaac agtggatcct gttactgcaa acgtctagtg actggacgtg    1800
gatgtgaccc ctgcctgcct ggccactggg gcctgagcca cgacctgctc ggctgccgcc    1860
cctgtgactg cgacgtgggt ggtgctttgg atccccagtg tgatgagggc acaggtcaat    1920
gccactgccg ccagcacatg gttgggcgac gctgtgagca ggtgcaacct ggctacttcc    1980
ggcccttcct ggaccaccta atttgggagg ctgaggacac ccgagggcag gtgctcgatg    2040
tggtggagcg cctggtgacc cccgggaaa ctccatcctg gactggctca ggcttcgtgc     2100
ggctacagga aggtcagacc ctggagttcc tggtggcctc tgtgccgaag ctatggact    2160 atgacctgct gctgcgctta gagccccagg tccctgagca atgggcagag ttggaactga    2220
ttgtgcagcg tccagggcct gtgcctgccc acagcctgtg tgggcatttg gtgcccaagg    2280
atgatcgcat ccaagggact ctgcaaccac atgccaggta cttgatattt cctaatcctg    2340
```

| | |
|---|---|
| tctgccttga gcctggtatc tcctacaagc tgcatctgaa gctggtacgg acaggggaa | 2400 |
| gtgcccagcc tgagactccc tactctggac ctggcctgct cattgactcg ctggtgctgc | 2460 |
| tgccccgtgt cctggtgcta gagatgttta gtgggggtga tgctgctgcc ctggagcgcc | 2520 |
| aggccacctt tgaacgctac caatgccatg aggagggtct ggtgcccagc aagacttctc | 2580 |
| cctctgaggc ctgcgcaccc ctcctcatca gcctgtccac cctcatctac aatggtgccc | 2640 |
| tgccatgtca gtgcaaccct caaggttcac tgagttctga gtgcaaccct catggtggtc | 2700 |
| agtgcctgtg caagcctgga gtggttgggc gccgctgtga cctctgtgcc cctggctact | 2760 |
| atggctttgg ccccacaggc tgtcaagcct gccagtgcag ccacgagggg gcactcagca | 2820 |
| gtctctgtga aaagaccagt gggcaatgtc tctgtcgaac tggtgccttt gggcttcgct | 2880 |
| gtgaccgctg ccagcgtggc cagtggggat ccctagctg ccggccatgt gtctgcaatg | 2940 |
| ggcatgcaga tgagtgcaac acccacacag gcgcttgcct gggctgccgt gatcacacag | 3000 |
| ggggtgagca ctgtgaaagg tgcattgctg gtttccacgg ggaccacgg ctgccatatg | 3060 |
| ggggccagtg ccggccctgt ccctgtcctg aaggccctgg gagccaacgg cactttgcta | 3120 |
| cttcttgcca ccaggatgaa tattcccagc agattgtgtg ccactgccgg gcaggctata | 3180 |
| cggggctgcg atgtgaagct tgtgcccctg gcactttgg ggaccatca aggccaggtg | 3240 |
| gccggtgcca actgtgtgag tgcagtggga cattgaccc aatggatcct gatgcctgtg | 3300 |
| acccccacac ggggcaatgc ctgcgctgtt tacaccacac agagggtcca cactgtgccc | 3360 |
| actgcaagcc tggcttccat gggcaggctg cccgacagag ctgtcaccgc tgcacatgca | 3420 |
| acctgctggg cacaaatccg cagcagtgcc catctcctga ccagtgccac tgtgatccaa | 3480 |
| gcagtgggca gtgcccatgc ctccccaatg tccagggccc tagctgtgac cgctgtgccc | 3540 |
| ccaacttctg gaacctcacc agtggccatg gttgccagcc ttgtgcctgc cacccaagcc | 3600 |
| gggccagagg ccccacctgc aacgagttca gggcagtg ccactgccgt gccggctttg | 3660 |
| gagggcggac ttgttctgag tgccaagagc tccactgggg agaccctggg ttgcagtgcc | 3720 |
| atgcctgtga ttgtgactct cgtggaatag atacacctca gtgtcaccgc ttcacaggtc | 3780 |
| actgcagctg ccgcccaggg gtgtctggtg tgcgctgtga ccagtgtgcc cgtggcttct | 3840 |
| caggaatctt tcctgcctgc catccctgcc atgcatgctt cggggattgg gaccgagtgg | 3900 |
| tgcaggactt ggcagcccgt acacagcgcc tagagcagcg ggcgcaggag ttgcaacaga | 3960 |
| cgggtgtgct gggtgccttt gagagcagct tctggcacat gcaggagaag ctgggcattg | 4020 |
| tgcagggcat cgtaggtgcc cgcaacacct cagccgcctc cactgtgcag cttgtggagg | 4080 |
| ccacagagga gctgcggcgt gaaattgggg aggccactga gcacctgact cagctcgagg | 4140 |
| cagacctgac agatgtgcaa gatgagaact tcaatgccaa ccatgcacta agtggtctgg | 4200 |
| agcgagatag gcttgcactt aatctcacac tgcggcagct cgaccagcat cttgacttgc | 4260 |
| tcaaacattc aaacttcctg ggtgcctatg acagcatccg gcatgcccat agccagtctg | 4320 |
| cagaggcaga acgtcgtgcc aatacctcag ccctggcagt acctagccct gtgagcaact | 4380 |
| cggcaagtgc tcggcatcgg acagaggcac tgatggatgc tcagaaggag gacttcaaca | 4440 |
| gcaaacacat ggccaaccag cgggcacttg gcaagctctc tgcccatacc cacaccctga | 4500 |
| gcctgacaga cataaatgag ctggtgtgtg gggcaccagg ggatgcaccc tgtgctacaa | 4560 |
| gcccttgtgg gggtgccggc tgtcgagatg aggatgggca gccgcgctgt ggggcctca | 4620 |
| gctgcaatgg ggcagcggct acagcagacc tagcactggg ccgggcccgg cacacacagg | 4680 |
| cagagctgca gcgggcactg gcagaaggtg gtagcatcct cagcagagtg gctgagactc | 4740 |

-continued

```
gtcggcaggc aagcgaggca cagcagcggg cccaggcagc cctggacaag gctaatgctt    4800
ccaggggaca ggtggaacag gccaaccagg aacttcaaga acttatccag agtgtgaagg    4860
acttcctcaa ccaggagggg gctgatcctg atagcattga aatggtggcc acacgggtgc    4920
tagagctctc catcccagct tcagctgagc agatccagca cctggcgggt gcgattgcag    4980
agcgagtccg gagcctggca gatgtggatg cgatcctggc acgtactgta ggagatgtgc    5040
gtcgtgccga gcagctactg caggatgcac ggcgggcaag gagctgggct gaggatgaga    5100
aacagaaggc agagacagta caggcagcac tggaggaggc ccagcgggca cagggtattg    5160
cccagggtgc catccggggg gcagtggctg acacacggga cacagagcag accctgtacc    5220
aggtacagga gaggatggca ggtgcagagc gggcactgag ctctgcaggt gaaagggctc    5280
ggcagttgga tgctctcctg gaggctctga aattgaaacg gcaggaaat agtctggcag    5340
cctctacagc agaagaaacg gcaggcagtg cccagggtcg tgcccaggag gctgagcagc    5400
tgctacgcgg tcctctgggt gatcagtacc agacggtgaa ggccctagct gagcgcaagg    5460
cccaaggtgt gctggctgca caggcaaggg cagaacaact gcgggatgag gctcgggacc    5520
tgttgcaagc cgctcaggac aagctgcagc ggctacagga attggaaggc acctatgagg    5580
aaaatgagcg ggcactggag agtaaggcag cccagttgga cgggttggag gccaggatgc    5640
gcagcgtgct tcaagccatc aacttgcagg tgcagatcta caacacctgc cagtgacccc    5700
tgcccaaggc ctaccccagt cctagcact gccccacatg catgtctgcc tatgcactga    5760
agagctcttg gcccggcagg gcccccaata aaccagtgtg aaccccaaa aaaaaaa       5817
```

```
<210> SEQ ID NO 6
<211> LENGTH: 1798
<212> TYPE: PRT
<213> ORGANISM: Homo sapiens

<400> SEQUENCE: 6

Met Glu Leu Thr Ser Arg Glu Arg Gly Arg Gly Gln Pro Leu Pro Trp
1               5                   10                  15

Glu Leu Arg Leu Gly Leu Leu Leu Ser Val Leu Ala Ala Thr Leu Ala
            20                  25                  30

Gln Ala Pro Ala Pro Asp Val Pro Gly Cys Ser Arg Gly Ser Cys Tyr
        35                  40                  45

Pro Ala Thr Gly Asp Leu Leu Val Gly Arg Ala Asp Arg Leu Thr Ala
    50                  55                  60

Ser Ser Thr Cys Gly Leu Asn Gly Pro Gln Pro Tyr Cys Ile Val Ser
65                  70                  75                  80

His Leu Gln Asp Glu Lys Lys Cys Phe Leu Cys Asp Ser Arg Arg Pro
                85                  90                  95

Phe Ser Ala Arg Asp Asn Pro His Ser His Arg Ile Gln Asn Val Val
            100                 105                 110

Thr Ser Phe Ala Pro Gln Arg Arg Ala Ala Trp Trp Gln Ser Glu Asn
        115                 120                 125

Gly Ile Pro Ala Val Thr Ile Gln Leu Asp Leu Glu Ala Glu Phe His
    130                 135                 140

Phe Thr His Leu Ile Met Thr Phe Lys Thr Phe Arg Pro Ala Ala Met
145                 150                 155                 160

Leu Val Glu Arg Ser Ala Asp Phe Gly Arg Thr Trp His Val Tyr Arg
                165                 170                 175

Tyr Phe Ser Tyr Asp Cys Gly Ala Asp Phe Pro Gly Val Pro Leu Ala
```

```
                180             185                 190
Pro Pro Arg His Trp Asp Asp Val Val Cys Glu Ser Arg Tyr Ser Glu
            195                 200             205
Ile Glu Pro Ser Thr Glu Gly Glu Val Ile Tyr Arg Val Leu Asp Pro
            210                 215                 220
Ala Ile Pro Ile Pro Asp Pro Tyr Ser Ser Arg Ile Gln Asn Leu Leu
225                 230                 235                 240
Lys Ile Thr Asn Leu Arg Val Asn Leu Thr Arg Leu His Thr Leu Gly
                245                 250                 255
Asp Asn Leu Leu Asp Pro Arg Arg Glu Ile Arg Glu Lys Tyr Tyr Tyr
            260                 265                 270
Ala Leu Tyr Glu Leu Val Val Arg Gly Asn Cys Phe Cys Tyr Gly His
            275                 280                 285
Ala Ser Glu Cys Ala Pro Ala Pro Gly Ala Pro Ala His Ala Glu Gly
            290                 295                 300
Met Val His Gly Ala Cys Ile Cys Lys His Asn Thr Arg Gly Leu Asn
305                 310                 315                 320
Cys Glu Gln Cys Gln Asp Phe Tyr Arg Asp Leu Pro Trp Arg Pro Ala
                325                 330                 335
Glu Asp Gly His Ser His Ala Cys Arg Lys Cys Glu Cys His Gly His
            340                 345                 350
Thr His Ser Cys His Phe Asp Met Ala Val Tyr Leu Ala Ser Gly Asn
            355                 360                 365
Val Ser Gly Gly Val Cys Asp Gly Cys Gln His Asn Thr Ala Gly Arg
            370                 375                 380
His Cys Glu Leu Cys Arg Pro Phe Phe Tyr Arg Asp Pro Thr Lys Asp
385                 390                 395                 400
Leu Arg Asp Pro Ala Val Cys Arg Ser Cys Asp Cys Asp Pro Met Gly
                405                 410                 415
Ser Gln Asp Gly Gly Arg Cys Asp Ser His Asp Asp Pro Ala Leu Gly
            420                 425                 430
Leu Val Ser Gly Gln Cys Arg Cys Lys Glu His Val Val Gly Thr Arg
            435                 440                 445
Cys Gln Gln Cys Arg Asp Gly Phe Phe Gly Leu Ser Ile Ser Asp Arg
            450                 455                 460
Leu Gly Cys Arg Arg Cys Gln Cys Asn Ala Arg Gly Thr Val Pro Gly
465                 470                 475                 480
Ser Thr Pro Cys Asp Pro Asn Ser Gly Ser Cys Tyr Cys Lys Arg Leu
                485                 490                 495
Val Thr Gly Arg Gly Cys Asp Arg Cys Leu Pro Gly His Trp Gly Leu
            500                 505                 510
Ser His Asp Leu Leu Gly Cys Arg Pro Cys Asp Cys Val Gly Gly
            515                 520                 525
Ala Leu Asp Pro Gln Cys Asp Glu Gly Thr Gly Gln Cys His Cys Arg
            530                 535                 540
Gln His Met Val Gly Arg Arg Cys Glu Gln Val Gln Pro Gly Tyr Phe
545                 550                 555                 560
Arg Pro Phe Leu Asp His Leu Ile Trp Glu Ala Glu Thr Arg Gly
                565                 570                 575
Gln Val Leu Asp Val Val Glu Arg Leu Val Thr Pro Gly Glu Thr Pro
            580                 585                 590
Ser Trp Thr Gly Ser Gly Phe Val Arg Leu Gln Glu Gly Gln Thr Leu
            595                 600                 605
```

```
Glu Phe Leu Val Ala Ser Val Pro Lys Ala Met Asp Tyr Asp Leu Leu
    610                 615                 620

Leu Arg Leu Glu Pro Gln Val Pro Glu Gln Trp Ala Glu Leu Glu Leu
625                 630                 635                 640

Ile Val Gln Arg Pro Gly Pro Val Pro Ala His Ser Leu Cys Gly His
                645                 650                 655

Leu Val Pro Lys Asp Asp Arg Ile Gln Gly Thr Leu Gln Pro His Ala
                660                 665                 670

Arg Tyr Leu Ile Phe Pro Asn Pro Val Cys Leu Glu Pro Gly Ile Ser
                675                 680                 685

Tyr Lys Leu His Leu Lys Leu Val Arg Thr Gly Gly Ser Ala Gln Pro
    690                 695                 700

Glu Thr Pro Tyr Ser Gly Pro Gly Leu Leu Ile Asp Ser Leu Val Leu
705                 710                 715                 720

Leu Pro Arg Val Leu Val Leu Glu Met Phe Ser Gly Gly Asp Ala Ala
                725                 730                 735

Ala Leu Glu Arg Gln Ala Thr Phe Glu Arg Tyr Gln Cys His Glu Glu
                740                 745                 750

Gly Leu Val Pro Ser Lys Thr Ser Pro Ser Glu Ala Cys Ala Pro Leu
    755                 760                 765

Leu Ile Ser Leu Ser Thr Leu Ile Tyr Asn Gly Ala Leu Pro Cys Gln
770                 775                 780

Cys Asn Pro Gln Gly Ser Leu Ser Ser Glu Cys Asn Pro His Gly Gly
785                 790                 795                 800

Gln Cys Leu Cys Lys Pro Gly Val Val Gly Arg Arg Cys Asp Leu Cys
                805                 810                 815

Ala Pro Gly Tyr Tyr Gly Phe Gly Pro Thr Gly Cys Gln Ala Cys Gln
                820                 825                 830

Cys Ser His Glu Gly Ala Leu Ser Ser Leu Cys Glu Lys Thr Ser Gly
    835                 840                 845

Gln Cys Leu Cys Arg Thr Gly Ala Phe Gly Leu Arg Cys Asp Arg Cys
850                 855                 860

Gln Arg Gly Gln Trp Gly Phe Pro Ser Cys Arg Pro Cys Val Cys Asn
865                 870                 875                 880

Gly His Ala Asp Glu Cys Asn Thr His Thr Gly Ala Cys Leu Gly Cys
                885                 890                 895

Arg Asp His Thr Gly Gly Glu His Cys Glu Arg Cys Ile Ala Gly Phe
                900                 905                 910

His Gly Asp Pro Arg Leu Pro Tyr Gly Gly Gln Cys Arg Pro Cys Pro
    915                 920                 925

Cys Pro Glu Gly Pro Gly Ser Gln Arg His Phe Ala Thr Ser Cys His
930                 935                 940

Gln Asp Glu Tyr Ser Gln Gln Ile Val Cys His Cys Arg Ala Gly Tyr
945                 950                 955                 960

Thr Gly Leu Arg Cys Glu Ala Cys Ala Pro Gly His Phe Gly Asp Pro
                965                 970                 975

Ser Arg Pro Gly Gly Arg Cys Gln Leu Cys Glu Cys Ser Gly Asn Ile
                980                 985                 990

Asp Pro Met Asp Pro Asp Ala Cys  Asp Pro His Thr Gly  Gln Cys Leu
    995                 1000                1005

Arg Cys Leu His His Thr Glu  Gly Pro His Cys Ala  His Cys Lys
    1010                1015                1020
```

```
Pro Gly Phe His Gly Gln Ala  Ala Arg Gln Ser Cys  His Arg Cys
    1025                1030                1035

Thr Cys Asn Leu Leu Gly Thr  Asn Pro Gln Gln Cys  Pro Ser Pro
    1040                1045                1050

Asp Gln Cys His Cys Asp Pro  Ser Ser Gly Gln Cys  Pro Cys Leu
    1055                1060                1065

Pro Asn Val Gln Gly Pro Ser  Cys Asp Arg Cys Ala  Pro Asn Phe
    1070                1075                1080

Trp Asn Leu Thr Ser Gly His  Gly Cys Gln Pro Cys  Ala Cys His
    1085                1090                1095

Pro Ser Arg Ala Arg Gly Pro  Thr Cys Asn Glu Phe  Thr Gly Gln
    1100                1105                1110

Cys His Cys Arg Ala Gly Phe  Gly Gly Arg Thr Cys  Ser Glu Cys
    1115                1120                1125

Gln Glu Leu His Trp Gly Asp  Pro Gly Leu Gln Cys  His Ala Cys
    1130                1135                1140

Asp Cys Asp Ser Arg Gly Ile  Asp Thr Pro Gln Cys  His Arg Phe
    1145                1150                1155

Thr Gly His Cys Ser Cys Arg  Pro Gly Val Ser Gly  Val Arg Cys
    1160                1165                1170

Asp Gln Cys Ala Arg Gly Phe  Ser Gly Ile Phe Pro  Ala Cys His
    1175                1180                1185

Pro Cys His Ala Cys Phe Gly  Asp Trp Asp Arg Val  Val Gln Asp
    1190                1195                1200

Leu Ala Ala Arg Thr Gln Arg  Leu Glu Gln Arg Ala  Gln Glu Leu
    1205                1210                1215

Gln Gln Thr Gly Val Leu Gly  Ala Phe Glu Ser Ser  Phe Trp His
    1220                1225                1230

Met Gln Glu Lys Leu Gly Ile  Val Gln Gly Ile Val  Gly Ala Arg
    1235                1240                1245

Asn Thr Ser Ala Ala Ser Thr  Ala Gln Leu Val Glu  Ala Thr Glu
    1250                1255                1260

Glu Leu Arg Arg Glu Ile Gly  Glu Ala Thr Glu His  Leu Thr Gln
    1265                1270                1275

Leu Glu Ala Asp Leu Thr Asp  Val Gln Asp Glu Asn  Phe Asn Ala
    1280                1285                1290

Asn His Ala Leu Ser Gly Leu  Glu Arg Asp Arg Leu  Ala Leu Asn
    1295                1300                1305

Leu Thr Leu Arg Gln Leu Asp  Gln His Leu Asp Leu  Leu Lys His
    1310                1315                1320

Ser Asn Phe Leu Gly Ala Tyr  Asp Ser Ile Arg His  Ala His Ser
    1325                1330                1335

Gln Ser Ala Glu Ala Glu Arg  Arg Ala Asn Thr Ser  Ala Leu Ala
    1340                1345                1350

Val Pro Ser Pro Val Ser Asn  Ser Ala Ser Ala Arg  His Arg Thr
    1355                1360                1365

Glu Ala Leu Met Asp Ala Gln  Lys Glu Asp Phe Asn  Ser Lys His
    1370                1375                1380

Met Ala Asn Gln Arg Ala Leu  Gly Lys Leu Ser Ala  His Thr His
    1385                1390                1395

Thr Leu Ser Leu Thr Asp Ile  Asn Glu Leu Val Cys  Gly Ala Pro
    1400                1405                1410

Gly Asp Ala Pro Cys Ala Thr  Ser Pro Cys Gly Gly  Ala Gly Cys
```

1415                1420                1425

Arg Asp Glu Asp Gly Gln Pro Arg Cys Gly Gly Leu Ser Cys Asn
        1430                1435                1440

Gly Ala Ala Ala Thr Ala Asp Leu Ala Leu Gly Arg Ala Arg His
        1445                1450                1455

Thr Gln Ala Glu Leu Gln Arg Ala Leu Ala Glu Gly Gly Ser Ile
        1460                1465                1470

Leu Ser Arg Val Ala Glu Thr Arg Arg Gln Ala Ser Glu Ala Gln
        1475                1480                1485

Gln Arg Ala Gln Ala Ala Leu Asp Lys Ala Asn Ala Ser Arg Gly
        1490                1495                1500

Gln Val Glu Gln Ala Asn Gln Glu Leu Gln Glu Leu Ile Gln Ser
        1505                1510                1515

Val Lys Asp Phe Leu Asn Gln Glu Gly Ala Asp Pro Asp Ser Ile
        1520                1525                1530

Glu Met Val Ala Thr Arg Val Leu Glu Leu Ser Ile Pro Ala Ser
        1535                1540                1545

Ala Glu Gln Ile Gln His Leu Ala Gly Ala Ile Ala Glu Arg Val
        1550                1555                1560

Arg Ser Leu Ala Asp Val Asp Ala Ile Leu Ala Arg Thr Val Gly
        1565                1570                1575

Asp Val Arg Arg Ala Glu Gln Leu Leu Gln Asp Ala Arg Arg Ala
        1580                1585                1590

Arg Ser Trp Ala Glu Asp Glu Lys Gln Lys Ala Glu Thr Val Gln
        1595                1600                1605

Ala Ala Leu Glu Glu Ala Gln Arg Ala Gln Gly Ile Ala Gln Gly
        1610                1615                1620

Ala Ile Arg Gly Ala Val Ala Asp Thr Arg Asp Thr Glu Gln Thr
        1625                1630                1635

Leu Tyr Gln Val Gln Glu Arg Met Ala Gly Ala Glu Arg Ala Leu
        1640                1645                1650

Ser Ser Ala Gly Glu Arg Ala Arg Gln Leu Asp Ala Leu Leu Glu
        1655                1660                1665

Ala Leu Lys Leu Lys Arg Ala Gly Asn Ser Leu Ala Ala Ser Thr
        1670                1675                1680

Ala Glu Glu Thr Ala Gly Ser Ala Gln Gly Arg Ala Gln Glu Ala
        1685                1690                1695

Glu Gln Leu Leu Arg Gly Pro Leu Gly Asp Gln Tyr Gln Thr Val
        1700                1705                1710

Lys Ala Leu Ala Glu Arg Lys Ala Gln Gly Val Leu Ala Ala Gln
        1715                1720                1725

Ala Arg Ala Glu Gln Leu Arg Asp Glu Ala Arg Asp Leu Leu Gln
        1730                1735                1740

Ala Ala Gln Asp Lys Leu Gln Arg Leu Gln Glu Leu Glu Gly Thr
        1745                1750                1755

Tyr Glu Glu Asn Glu Arg Ala Leu Glu Ser Lys Ala Ala Gln Leu
        1760                1765                1770

Asp Gly Leu Glu Ala Arg Met Arg Ser Val Leu Gln Ala Ile Asn
        1775                1780                1785

Leu Gln Val Gln Ile Tyr Asn Thr Cys Gln
        1790                1795

<210> SEQ ID NO 7

<211> LENGTH: 7889
<212> TYPE: DNA
<213> ORGANISM: Homo sapiens

<400> SEQUENCE: 7

| | | | | | |
|---|---|---|---|---|---|
| gtgcaggctg | ctcccggggt | aggtgaggga | agcgcggagg | cggcgcgcgg | gggcagtggt | 60 |
| cggcgagcag | cgcggtcctc | gctagggcg | cccacccgtc | agtctctccg | gcgcgagccg | 120 |
| ccgccaccgc | ccgcgccgga | gtcaggcccc | tgggccccca | ggctcaagca | gcgaagcggc | 180 |
| ctccggggga | cgccgctagg | cgagaggaac | gcgccggtgc | ccttgccttc | gccgtgaccc | 240 |
| agcgtgcggg | cggcgggatg | agagggagcc | atcgggccgc | gccggccctg | cggcccggg | 300 |
| ggcggctctg | gcccgtgctg | gccgtgctgg | cggcggccgc | cgcggcgggc | tgtgcccagg | 360 |
| cagccatgga | cgagtgcacg | gacgagggcg | ggcggccgca | cgcgctgcatg | cccgagttcg | 420 |
| tcaacgccgc | cttcaacgtg | actgtggtgg | ccaccaacac | gtgtgggact | ccgcccgagg | 480 |
| aatactgtgt | gcagaccggg | gtgaccgggg | tcaccaagtc | ctgtcacctg | tgcgacgccg | 540 |
| ggcagcccca | cctgcagcac | ggggcagcct | tcctgaccga | ctacaacaac | caggccgaca | 600 |
| ccacctggtg | gcaaagccag | accatgctgg | ccggggtgca | gtaccccagc | tccatcaacc | 660 |
| tcacgctgca | cctgggaaaa | gcttttgaca | tcacctatgt | gcgtctcaag | ttccacacca | 720 |
| gccgccgga | gagctttgcc | atttacaagc | gcacacggga | agacgggccc | tggattcctt | 780 |
| accagtacta | cagtggttcc | tgtgagaaca | cctactccaa | ggcaaaccgc | ggcttcatca | 840 |
| ggacaggagg | ggacgagcag | caggccttgt | gtactgatga | attcagtgac | atttctcccc | 900 |
| tcactggggg | caacgtggcc | ttttctaccc | tggaaggaag | gcccagcgcc | tataactttg | 960 |
| acaatagccc | tgtgctgcag | gaatgggtaa | ctgccactga | catcagagta | actcttaatc | 1020 |
| gcctgaacac | ttttggagat | gaagtgttta | acgatcccaa | agttctcaag | tcctattatt | 1080 |
| atgccatctc | tgattttgct | gtaggtggca | gatgtaaatg | taatggacac | gcaagcgagt | 1140 |
| gtatgaagaa | cgaatttgat | aagctggtgt | gtaattgcaa | acataacaca | tatgagtag | 1200 |
| actgtgaaaa | gtgtcttcct | ttcttcaatg | accggccgtg | gaggagggca | actgcggaaa | 1260 |
| gtgccagtga | atgcctgccc | tgtgattgca | atggtcgatc | ccaggaatgc | acttcgacc | 1320 |
| ctgaactcta | tcgttccact | ggccatgggg | gccactgtac | caactgccag | ataacacag | 1380 |
| atggcgccca | ctgtgagagg | tgccgagaga | acttcttccg | ccttggcaac | aatgaagcct | 1440 |
| gctcttcatg | ccactgtagt | cctgtgggct | ctctaagcac | acagtgtgat | agttacggca | 1500 |
| gatgcagctg | taagccagga | gtgatggggg | acaaatgtga | ccgttgccag | cctggattcc | 1560 |
| attctctcac | tgaagcagga | tgcaggccat | gctcttgtga | tccctctggc | agcatagatg | 1620 |
| aatgtaatat | tgaaacagga | agatgtgttt | gcaaagacaa | tgtcgaaggc | ttcaattgtg | 1680 |
| aaagatgcaa | acctggatt | tttaatctgg | aatcatctaa | tcctcggggt | tgcacaccct | 1740 |
| gcttctgctt | tgggcattct | tctgtctgta | caaacgctgt | tggctacagt | gtttattcta | 1800 |
| tctcctctac | ctttcagatt | gatgaggatg | ggtggcgtgc | ggaacagaga | gatggctctg | 1860 |
| aagcatctct | cgagtggtcc | tctgagaggc | aagatatcgc | cgtgatctca | gacagctact | 1920 |
| ttcctcggta | cttcattgct | cctgcaaagt | tcttgggcaa | gcaggtgttg | agttatggtc | 1980 |
| agaacctctc | cttctcctt | cgagtggaca | ggcgagatac | tcgcctctct | gcagaagacc | 2040 |
| ttgtgcttga | gggagctggc | ttaagagtat | ctgtacccct | tgatcgctcag | ggcaattcct | 2100 |
| atccaagtga | gaccactgtg | aagtatgtct | tcaggctcca | tgaagcaaca | gattacccctt | 2160 |
| ggaggcctgc | tcttacccct | tttgaattc | agaagctcct | aaacaacttg | acctctatca | 2220 |

| | |
|---|---|
| agatacgtgg gacatacagt gagagaagtg ctggatattt ggatgatgtc accctggcaa | 2280 |
| gtgctcgtcc tgggcctgga gtccctgcaa cttgggtgga gtcctgcacc tgtcctgtgg | 2340 |
| gatatggagg gcagttttgt gagatgtgcc tctcaggtta cagaagagaa actcctaatc | 2400 |
| ttggaccata cagtccatgt gtgctttgcg cctgcaatgg acacagcgag acctgtgatc | 2460 |
| ctgagacagg tgtttgtaac tgcagagaca atacggctgg cccgcactgt gagaagtgca | 2520 |
| gtgatgggta ctatggagat tcaactgcag gcacctcctc cgattgccaa ccctgtccgt | 2580 |
| gtcctggagg ttcaagttgt gctgttgttc ccaagacaaa ggaggtggtg tgcaccaact | 2640 |
| gtcctactgg caccactggt aagagatgtg agctctgtga tgatggctac tttggagacc | 2700 |
| ccctgggtag aaacggccct gtgagacttt gccgcctgtg ccagtgcagt gacaacatcg | 2760 |
| atcccaatgc agttggaaat tgcaatcgct tgacgggaga atgcctgaag tgcatctata | 2820 |
| acactgctgg cttctattgt gaccggtgca agacggatt ttttggaaat cccctggctc | 2880 |
| ccaatccagc agacaaatgc aaagcctgca attgcaatct gtatgggacc atgaagcagc | 2940 |
| agagcagctg taaccccgtg acggggcagt gtgaatgttt gcctcacgtg actggccagg | 3000 |
| actgtggtgc ttgtgaccct ggattctaca atctgcagag tgggcaaggc tgtgagaggt | 3060 |
| gtgactgcca tgccttgggc tccaccaatg ggcagtgtga catccgcacc ggccagtgtg | 3120 |
| agtgccagcc cggcatcact ggtcagcact gtgagcgctg tgaggtcaac cactttgggt | 3180 |
| ttggacctga aggctgcaaa ccctgtgact gtcatcctga gggatctctt tcacttcagt | 3240 |
| gcaaagatga tggtcgctgt gaatgcagag aaggctttgt gggaaatcgc tgtgaccagt | 3300 |
| gtgaagaaaa ctatttctac aatcggtctt ggcctggctg ccaggaatgt ccagcttgtt | 3360 |
| accggctggt aaaggataag gttgctgatc atagagtgaa gctccaggaa ttagagagtc | 3420 |
| tcatagcaaa ccttggaact ggggatgaga tggtgacaga tcaagccttc gaggatagac | 3480 |
| taaaggaagc agagagggaa gttatggacc tccttcgtga ggcccaggat gtcaaagatg | 3540 |
| ttgaccagaa tttgatggat cgcctacaga gagtgaataa cactctgtcc agccaaatta | 3600 |
| gccgtttaca gaatatccgg aataccattg aagagactgg aaacttggct gaacaagcgc | 3660 |
| gtgcccatgt agagaacaca gagcggttga ttgaaatcgc atccagagaa cttgagaaag | 3720 |
| caaaagtcgc tgctgccaat gtgtcagtca ctcagccaga atctacaggg gacccaaaca | 3780 |
| acatgactct tttggcagaa gaggctcgaa agcttgctga acgtcataaa caggaagctg | 3840 |
| atgacattgt tcgagtggca aagacagcca atgatacgtc aactgaggca tacaacctgc | 3900 |
| ttctgaggac actggcagga gaaaatcaaa cagcatttga gattgaagag cttaatagga | 3960 |
| agtatgaaca agcgaagaac atctcacagg atctggaaaa acaagctgcc cgagtacatg | 4020 |
| aggaggccaa aagggccggt gacaaagctg tggagatcta tgccagcgtg gctcagctga | 4080 |
| gcccttttgga ctctgagaca ctggagaatg aagcaaataa cataaagatg gaagctgaga | 4140 |
| atctggaaca actgattgac cagaaattaa aagattatga ggacctcaga gaagatatga | 4200 |
| gagggaagga acttgaagtc aagaaccttc tggagaaagg caagactgaa cagcagaccg | 4260 |
| cagaccaact cctagcccga gctgatgctg ccaaggccct cgctgaagaa gctgcaaaga | 4320 |
| agggacggga taccttacaa gaagctaatg acattctcaa caacctgaaa gattttgata | 4380 |
| ggcgtgtgaa cgataacaag acggccgcag aggaggcact aaggaagatt cctgccatca | 4440 |
| accagaccat cactgaagcc aatgaaaaga ccagagaagc ccagcaggcc ctgggcagtg | 4500 |
| ctgcggcgga tgccacagag gccaagaaca aggcccatga ggcggagagg atcgcgagcg | 4560 |

```
ctgtccaaaa gaatgccacc agcaccaagg cagaagctga aagaactttt gcagaagtta    4620
cagatctgga taatgaggtg aacaatatgt tgaagcaact gcaggaagca gaaaaagagc    4680
taaagagaaa acaagatgac gctgaccagg acatgatgat ggcagggatg gcttcacagg    4740
ctgctcaaga agccgagatc aatgccagaa aagccaaaaa ctctgttact agcctcctca    4800
gcattattaa tgacctcttg gagcagctgg ggcagctgga tacagtggac ctgaataagc    4860
taaacgagat tgaaggcacc ctaaacaaag ccaaagatga aatgaaggtc agcgatcttg    4920
ataggaaagt gtctgacctg gagaatgaag ccaagaagca ggaggctgcc atcatggact    4980
ataaccgaga tatcgaggag atcatgaagg acattcgcaa tctggaggac atcaggaaga    5040
ccttaccatc tggctgcttc aacaccccgt ccattgaaaa gccctagtgt ctttagggct    5100
ggaaggcagc atccctctga caggggggca gttgtgaggc cacagagtgc cttgacacaa    5160
agattacatt tttcagaccc ccactcctct gctgctgtcc atgactgtcc ttttgaacca    5220
ggaaaagtca cagagtttaa agagaagcaa attaaacatc ctgaatcggg aacaaagggt    5280
tttatctaat aaagtgtctc ttccattcac gttgctacct tacccacact ttcccttctg    5340
atttgcgtga ggacgtggca tcctacgtta ctgtacagtg gcataagcac atcgtgtgag    5400
cccatgtatg ctggggtaga gcaagtagcc ctcccctgtc tcatcgatac cagcagaacc    5460
tcctcagtct cagtactctt gtttctatga aggaaaagtt tggctactaa cagtagcatt    5520
gtgatggcca gtatatccag tccatggata agaaaatgc atctgcatct cctacccctc    5580
ttccttctaa gcaaaaggaa ataaacatcc tgtgccaaag gtattggtca tttagaatgt    5640
cggtagccat ccatcagtgc ttttagttat tatgagtgta ggacactgag ccatccgtgg    5700
gtcaggatgc aattatttat aaaagtctcc aggtgaacat ggctgaagat ttttctagta    5760
tattaataat tgactaggaa gatgaacttt ttttcagatc tttgggcagc tgataattta    5820
aatctggatg ggcagcttgc actcaccaat agaccaaaag acatcttttg atattcttat    5880
aaatggaact tacacagaag aaataggat atgataacca ctaaaatttt gttttcaaaa    5940
tcaaactaat tcttacagct ttttattag ttagtcttgg aactagtgtt aagtatctgg    6000
cagagaacag ttaatcccta aggtcttgac aaaacagaag aaaaacaagc ctcctcgtcc    6060
tagtcttttc tagcaaaggg ataaaactta gatggcagct tgtactgtca gaatcccgtg    6120
tatccatttg ttcttctgtt ggagagatga gacatttgac ccttagctcc agttttcttc    6180
tgatgtttcc atcttccaga atccctcaaa aaacattgtt tgccaaatcc tggtggcaaa    6240
tacttgcact cagtatttca cacagctgcc aacgctatcg agttcctgca ctttgtgatt    6300
taaatccact ctaaaccttc cctctaagtg tagagggaag acccttacgt ggagtttcct    6360
agtgggcttc tcaacttttg atcctcagct ctgtggtttt aagaccacag tgtgacagtt    6420
ccctgccaca caccccttc ctcctaccaa cccacctttg agattcatat atagccttta    6480
acactatgca actttgtact ttgcgtagca ggggcgggt gggggaaag aaactattat    6540
ctgacacact ggtgctatta attatttcaa atttatattt ttgtgtgaat gttttgtgtt    6600
ttgtttatca tgattataga ataaggaatt tatgtaaata tacttagtcc tatttctaga    6660
atgcactct gttcactttg ctcaattttt cctcttcact ggcacaatgt atctgaatac    6720
ctccttccct cccttctaga attctttgga ttgtactcca agaattgtg ccttgtgttt    6780
gcagcatctc cattctctaa aattaatata attgctttcc tccacaccca gccactgtaa    6840
agaggtaact tgggtcctct tccattgcag tcctgatgat cctaacctgc agcacggtgg    6900
ttttacaatg ttccagagca ggaacgccag gttgacaagc tatggtagga ttaggaaagt    6960
```

-continued

```
ttgctgaaga ggatctttga cgccacagtg ggactagcca ggaatgaggg agaaatgccc      7020
tttctggcaa ttgttggagc tggataggta agttttataa gggagtacat ttgactgag       7080 cacttagggc atcaggaaca gtgctactta ctgatgggta gactgggaga ggtggtgtaa      7140
cttagttctt gatgatccca cttcctgttt ccatctgctt gggataltacc agagtttacc     7200 acaagtgttt tgacgatata ctcctgagct ttcactctgc tgcttctccc aggcctcttc      7260
tactatggca ggagatgtgg cgtgctgttg caaagtttc acgtcattgt ttcctggcta       7320
gttcatttca ttaagtggct acatcctaac atatgcattt ggtcaaggtt gcagaagagg      7380
actgaagatt gactgccaag ctagtttggg tgaagttcac tccagcaagt ctcaggccac      7440 aatgggggtgg tttggtttgg tttccttta actttctttt tgttatttgc ttttctcctc      7500
cacctgtgtg gtatatttt taagcagaat tttattttt aaaataaaag gttctttaca        7560
agatgatacc ttaattacac tcccgcaaca cagccattat tttattgtct agctccagtt      7620
atctgtattt tatgtaatgt aattgacagg atggctgctg cagaatgctg gttgacacag      7680
ggattattat actgctattt ttccctgaat ttttttcctt tgaattccaa ctgtggacct      7740
tttatatgtg ccttcacttt agctgtttgc cttaatctct acagccttgc tctccggggt      7800
ggttaataaa atgcaacact tggcattttt atgtttaag aaaaacagta ttttatttat       7860
aataaaatct gaatatttgt aacccttta                                         7889
```

<210> SEQ ID NO 8
<211> LENGTH: 1609
<212> TYPE: PRT
<213> ORGANISM: Homo sapiens

<400> SEQUENCE: 8

```
Met Arg Gly Ser His Arg Ala Ala Pro Ala Leu Arg Pro Arg Gly Arg
1               5                  10                  15

Leu Trp Pro Val Leu Ala Val Leu Ala Ala Ala Ala Ala Gly Cys
            20                  25                  30

Ala Gln Ala Ala Met Asp Glu Cys Thr Asp Glu Gly Gly Arg Pro Gln
        35                  40                  45

Arg Cys Met Pro Glu Phe Val Asn Ala Ala Phe Asn Val Thr Val Val
    50                  55                  60

Ala Thr Asn Thr Cys Gly Thr Pro Pro Glu Glu Tyr Cys Val Gln Thr
65                  70                  75                  80

Gly Val Thr Gly Val Thr Lys Ser Cys His Leu Cys Asp Ala Gly Gln
                85                  90                  95

Pro His Leu Gln His Gly Ala Ala Phe Leu Thr Asp Tyr Asn Asn Gln
            100                 105                 110

Ala Asp Thr Thr Trp Trp Gln Ser Gln Thr Met Leu Ala Gly Val Gln
        115                 120                 125

Tyr Pro Ser Ser Ile Asn Leu Thr Leu His Leu Gly Lys Ala Phe Asp
    130                 135                 140

Ile Thr Tyr Val Arg Leu Lys Phe His Thr Ser Arg Pro Glu Ser Phe
145                 150                 155                 160

Ala Ile Tyr Lys Arg Thr Arg Glu Asp Gly Pro Trp Ile Pro Tyr Gln
                165                 170                 175

Tyr Tyr Ser Gly Ser Cys Glu Asn Thr Tyr Ser Lys Ala Asn Arg Gly
            180                 185                 190

Phe Ile Arg Thr Gly Gly Asp Glu Gln Gln Ala Leu Cys Thr Asp Glu
        195                 200                 205
```

-continued

Phe Ser Asp Ile Ser Pro Leu Thr Gly Gly Asn Val Ala Phe Ser Thr
        210                 215                 220

Leu Glu Gly Arg Pro Ser Ala Tyr Asn Phe Asp Asn Ser Pro Val Leu
225                 230                 235                 240

Gln Glu Trp Val Thr Ala Thr Asp Ile Arg Val Thr Leu Asn Arg Leu
                245                 250                 255

Asn Thr Phe Gly Asp Glu Val Phe Asn Asp Pro Lys Val Leu Lys Ser
                260                 265                 270

Tyr Tyr Tyr Ala Ile Ser Asp Phe Ala Val Gly Gly Arg Cys Lys Cys
            275                 280                 285

Asn Gly His Ala Ser Glu Cys Met Lys Asn Glu Phe Asp Lys Leu Val
        290                 295                 300

Cys Asn Cys Lys His Asn Thr Tyr Gly Val Asp Cys Glu Lys Cys Leu
305                 310                 315                 320

Pro Phe Phe Asn Asp Arg Pro Trp Arg Arg Ala Thr Ala Glu Ser Ala
                325                 330                 335

Ser Glu Cys Leu Pro Cys Asp Cys Asn Gly Arg Ser Gln Glu Cys Tyr
                340                 345                 350

Phe Asp Pro Glu Leu Tyr Arg Ser Thr Gly His Gly His Cys Thr
            355                 360                 365

Asn Cys Gln Asp Asn Thr Asp Gly Ala His Cys Glu Arg Cys Arg Glu
370                 375                 380

Asn Phe Phe Arg Leu Gly Asn Asn Glu Ala Cys Ser Ser Cys His Cys
385                 390                 395                 400

Ser Pro Val Gly Ser Leu Ser Thr Gln Cys Asp Ser Tyr Gly Arg Cys
                405                 410                 415

Ser Cys Lys Pro Gly Val Met Gly Asp Lys Cys Asp Arg Cys Gln Pro
                420                 425                 430

Gly Phe His Ser Leu Thr Glu Ala Gly Cys Arg Pro Cys Ser Cys Asp
            435                 440                 445

Pro Ser Gly Ser Ile Asp Glu Cys Asn Ile Glu Thr Gly Arg Cys Val
        450                 455                 460

Cys Lys Asp Asn Val Glu Gly Phe Asn Cys Glu Arg Cys Lys Pro Gly
465                 470                 475                 480

Phe Phe Asn Leu Glu Ser Ser Asn Pro Arg Gly Cys Thr Pro Cys Phe
                485                 490                 495

Cys Phe Gly His Ser Ser Val Cys Thr Asn Ala Val Gly Tyr Ser Val
            500                 505                 510

Tyr Ser Ile Ser Ser Thr Phe Gln Ile Asp Glu Asp Gly Trp Arg Ala
        515                 520                 525

Glu Gln Arg Asp Gly Ser Glu Ala Ser Leu Glu Trp Ser Ser Glu Arg
530                 535                 540

Gln Asp Ile Ala Val Ile Ser Asp Ser Tyr Phe Pro Arg Tyr Phe Ile
545                 550                 555                 560

Ala Pro Ala Lys Phe Leu Gly Lys Gln Val Leu Ser Tyr Gly Gln Asn
                565                 570                 575

Leu Ser Phe Ser Phe Arg Val Asp Arg Arg Asp Thr Arg Leu Ser Ala
                580                 585                 590

Glu Asp Leu Val Leu Glu Gly Ala Gly Leu Arg Val Ser Val Pro Leu
            595                 600                 605

Ile Ala Gln Gly Asn Ser Tyr Pro Ser Glu Thr Thr Val Lys Tyr Val
610                 615                 620

-continued

Phe Arg Leu His Glu Ala Thr Asp Tyr Pro Trp Arg Pro Ala Leu Thr
625                 630                 635                 640

Pro Phe Glu Phe Gln Lys Leu Leu Asn Asn Leu Thr Ser Ile Lys Ile
        645                 650                 655

Arg Gly Thr Tyr Ser Glu Arg Ser Ala Gly Tyr Leu Asp Asp Val Thr
            660                 665                 670

Leu Ala Ser Ala Arg Pro Gly Pro Gly Val Pro Ala Thr Trp Val Glu
        675                 680                 685

Ser Cys Thr Cys Pro Val Tyr Gly Gly Gln Phe Cys Glu Met Cys
690                 695                 700

Leu Ser Gly Tyr Arg Arg Glu Thr Pro Asn Leu Gly Pro Tyr Ser Pro
705                 710                 715                 720

Cys Val Leu Cys Ala Cys Asn Gly His Ser Glu Thr Cys Asp Pro Glu
            725                 730                 735

Thr Gly Val Cys Asn Cys Arg Asp Asn Thr Ala Gly Pro His Cys Glu
            740                 745                 750

Lys Cys Ser Asp Gly Tyr Tyr Gly Asp Ser Thr Ala Gly Thr Ser Ser
        755                 760                 765

Asp Cys Gln Pro Cys Pro Cys Pro Gly Gly Ser Ser Cys Ala Val Val
770                 775                 780

Pro Lys Thr Lys Glu Val Val Cys Thr Asn Cys Pro Thr Gly Thr Thr
785                 790                 795                 800

Gly Lys Arg Cys Glu Leu Cys Asp Asp Gly Tyr Phe Gly Asp Pro Leu
            805                 810                 815

Gly Arg Asn Gly Pro Val Arg Leu Cys Arg Leu Cys Gln Cys Ser Asp
        820                 825                 830

Asn Ile Asp Pro Asn Ala Val Gly Asn Cys Asn Arg Leu Thr Gly Glu
        835                 840                 845

Cys Leu Lys Cys Ile Tyr Asn Thr Ala Gly Phe Tyr Cys Asp Arg Cys
850                 855                 860

Lys Asp Gly Phe Phe Gly Asn Pro Leu Ala Pro Asn Pro Ala Asp Lys
865                 870                 875                 880

Cys Lys Ala Cys Asn Cys Asn Leu Tyr Gly Thr Met Lys Gln Gln Ser
            885                 890                 895

Ser Cys Asn Pro Val Thr Gly Gln Cys Glu Cys Leu Pro His Val Thr
            900                 905                 910

Gly Gln Asp Cys Gly Ala Cys Asp Pro Gly Phe Tyr Asn Leu Gln Ser
        915                 920                 925

Gly Gln Gly Cys Glu Arg Cys Asp Cys His Ala Leu Gly Ser Thr Asn
930                 935                 940

Gly Gln Cys Asp Ile Arg Thr Gly Gln Cys Glu Cys Gln Pro Gly Ile
945                 950                 955                 960

Thr Gly Gln His Cys Glu Arg Cys Glu Val Asn His Phe Gly Phe Gly
            965                 970                 975

Pro Glu Gly Cys Lys Pro Cys Asp Cys His Pro Glu Gly Ser Leu Ser
        980                 985                 990

Leu Gln Cys Lys Asp Asp Gly Arg Cys Glu Cys Arg Glu Gly Phe Val
        995                 1000                1005

Gly Asn Arg Cys Asp Gln Cys Glu Glu Asn Tyr Phe Tyr Asn Arg
        1010                1015                1020

Ser Trp Pro Gly Cys Gln Glu Cys Pro Ala Cys Tyr Arg Leu Val
        1025                1030                1035

Lys Asp Lys Val Ala Asp His Arg Val Lys Leu Gln Glu Leu Glu

-continued

```
                1040                1045                1050
Ser Leu Ile Ala Asn Leu Gly Thr Gly Asp Glu Met Val Thr Asp
                1055                1060                1065
Gln Ala Phe Glu Asp Arg Leu Lys Glu Ala Glu Arg Glu Val Met
                1070                1075                1080
Asp Leu Leu Arg Glu Ala Gln Asp Val Lys Asp Val Asp Gln Asn
                1085                1090                1095
Leu Met Asp Arg Leu Gln Arg Val Asn Asn Thr Leu Ser Ser Gln
                1100                1105                1110
Ile Ser Arg Leu Gln Asn Ile Arg Asn Thr Ile Glu Glu Thr Gly
                1115                1120                1125
Asn Leu Ala Glu Gln Ala Arg Ala His Val Glu Asn Thr Glu Arg
                1130                1135                1140
Leu Ile Glu Ile Ala Ser Arg Glu Leu Glu Lys Ala Lys Val Ala
                1145                1150                1155
Ala Ala Asn Val Ser Val Thr Gln Pro Glu Ser Thr Gly Asp Pro
                1160                1165                1170
Asn Asn Met Thr Leu Leu Ala Glu Glu Ala Arg Lys Leu Ala Glu
                1175                1180                1185
Arg His Lys Gln Glu Ala Asp Asp Ile Val Arg Val Ala Lys Thr
                1190                1195                1200
Ala Asn Asp Thr Ser Thr Glu Ala Tyr Asn Leu Leu Leu Arg Thr
                1205                1210                1215
Leu Ala Gly Glu Asn Gln Thr Ala Phe Glu Ile Glu Glu Leu Asn
                1220                1225                1230
Arg Lys Tyr Glu Gln Ala Lys Asn Ile Ser Gln Asp Leu Glu Lys
                1235                1240                1245
Gln Ala Ala Arg Val His Glu Ala Lys Arg Ala Gly Asp Lys
                1250                1255                1260
Ala Val Glu Ile Tyr Ala Ser Val Ala Gln Leu Ser Pro Leu Asp
                1265                1270                1275
Ser Glu Thr Leu Glu Asn Glu Ala Asn Asn Ile Lys Met Glu Ala
                1280                1285                1290
Glu Asn Leu Glu Gln Leu Ile Asp Gln Lys Leu Lys Asp Tyr Glu
                1295                1300                1305
Asp Leu Arg Glu Asp Met Arg Gly Lys Glu Leu Glu Val Lys Asn
                1310                1315                1320
Leu Leu Glu Lys Gly Lys Thr Glu Gln Gln Thr Ala Asp Gln Leu
                1325                1330                1335
Leu Ala Arg Ala Asp Ala Ala Lys Ala Leu Ala Glu Glu Ala Ala
                1340                1345                1350
Lys Lys Gly Arg Asp Thr Leu Gln Glu Ala Asn Asp Ile Leu Asn
                1355                1360                1365
Asn Leu Lys Asp Phe Asp Arg Arg Val Asn Asp Asn Lys Thr Ala
                1370                1375                1380
Ala Glu Glu Ala Leu Arg Lys Ile Pro Ala Ile Asn Gln Thr Ile
                1385                1390                1395
Thr Glu Ala Asn Glu Lys Thr Arg Glu Ala Gln Gln Ala Leu Gly
                1400                1405                1410
Ser Ala Ala Ala Asp Ala Thr Glu Ala Lys Asn Lys Ala His Glu
                1415                1420                1425
Ala Glu Arg Ile Ala Ser Ala Val Gln Lys Asn Ala Thr Ser Thr
                1430                1435                1440
```

-continued

```
Lys Ala Glu Ala Glu Arg Thr Phe Ala Glu Val Thr Asp Leu Asp
1445                1450                1455

Asn Glu Val Asn Asn Met Leu Lys Gln Leu Gln Glu Ala Glu Lys
1460                1465                1470

Glu Leu Lys Arg Lys Gln Asp Asp Ala Asp Gln Asp Met Met Met
1475                1480                1485

Ala Gly Met Ala Ser Gln Ala Ala Gln Glu Ala Glu Ile Asn Ala
1490                1495                1500

Arg Lys Ala Lys Asn Ser Val Thr Ser Leu Leu Ser Ile Ile Asn
1505                1510                1515

Asp Leu Leu Glu Gln Leu Gly Gln Leu Asp Thr Val Asp Leu Asn
1520                1525                1530

Lys Leu Asn Glu Ile Glu Gly Thr Leu Asn Lys Ala Lys Asp Glu
1535                1540                1545

Met Lys Val Ser Asp Leu Asp Arg Lys Val Ser Asp Leu Glu Asn
1550                1555                1560

Glu Ala Lys Lys Gln Glu Ala Ala Ile Met Asp Tyr Asn Arg Asp
1565                1570                1575

Ile Glu Glu Ile Met Lys Asp Ile Arg Asn Leu Glu Asp Ile Arg
1580                1585                1590

Lys Thr Leu Pro Ser Gly Cys Phe Asn Thr Pro Ser Ile Glu Lys
1595                1600                1605

Pro
```